United States Patent
Ma et al.

(10) Patent No.: US 10,355,227 B2
(45) Date of Patent: *Jul. 16, 2019

(54) METAL COMPLEX FOR PHOSPHORESCENT OLED

(71) Applicant: Universal Display Corporation, Ewing, NJ (US)

(72) Inventors: Bin Ma, Plainsboro, NJ (US); Edward Barron, Hamilton, NJ (US); Alan Deangelis, Pennington, NJ (US); Walter Yeager, Yardley, PA (US); Zeinab Elshenawy, Holland, PA (US); Harvey Wendt, Medford Lakes, NJ (US); Ting-Chih Wang, Lawrenceville, NJ (US); Kwang-Ohk Cheon, Holland, PA (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 696 days.

This patent is subject to a terminal disclaimer.

(21) Appl. No.: 14/450,865

(22) Filed: Aug. 4, 2014

(65) Prior Publication Data
US 2015/0171349 A1    Jun. 18, 2015

Related U.S. Application Data

(60) Provisional application No. 61/916,552, filed on Dec. 16, 2013.

(51) Int. Cl.
| H01L 51/00 | (2006.01) |
| C07F 15/00 | (2006.01) |
| H01L 51/50 | (2006.01) |

(52) U.S. Cl.
CPC ...... *H01L 51/0085* (2013.01); *C07F 15/0033* (2013.01); *H01L 51/0054* (2013.01);
(Continued)

(58) Field of Classification Search
CPC .................................................. H01L 51/0085
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhigiang et al., "Bright-Blue Electroluminescence From a Silyl-Substituted ter-(phenylene-vinylene) derivative," Appl. Phys. Lett., 74(6): 865-867 (1999).

(Continued)

*Primary Examiner* — Brian E McDowell
(74) *Attorney, Agent, or Firm* — Duane Morris LLP

(57) ABSTRACT

The present disclosure relates to novel iridium complexes that can be used in organic light emitting devices (OLEDs). The present disclosure also relates to devices and formulations that incorporate the iridium complexes. The iridium complex can be a compound having the formula $(L_A)_m Ir (L_B)_{3-m}$ (I);

wherein $L_A$ is

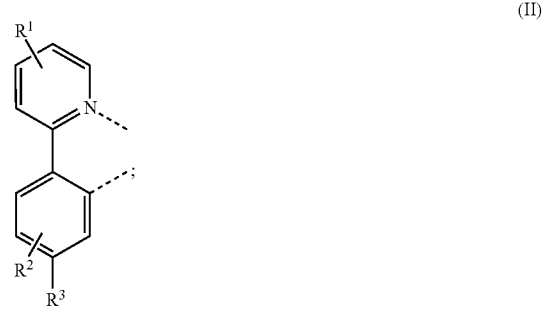

and
wherein $L_B$ can be one of:

(Continued)

-continued

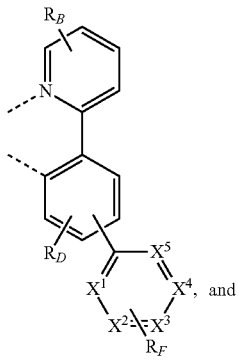

(IV)

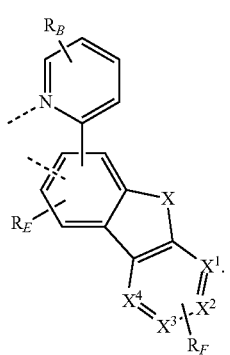

(V)

24 Claims, 5 Drawing Sheets

(52) U.S. Cl.
CPC ...... *H01L 51/0074* (2013.01); *H01L 51/0081* (2013.01); *H01L 51/5016* (2013.01); *H01L 51/5088* (2013.01)

(56) References Cited

U.S. PATENT DOCUMENTS

| | | | |
|---|---|---|---|
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1 | 2/2004 | Ma et al. | |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 9,028,980 B2 | 5/2015 | Abe et al. | |
| 9,184,397 B2 | 11/2015 | Kottas et al. | |
| 9,269,911 B2 | 2/2016 | Horiuchi et al. | |
| 9,630,893 B2 | 4/2017 | Xia et al. | |
| 9,634,264 B2 * | 4/2017 | Beers | H01L 51/0085 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0151042 A1 | 8/2003 | Marks et al. | |
| 2003/0152802 A1 | 8/2003 | Tsuboyama et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2014/0054564 A1 | 2/2014 | Kim et al. | |

FOREIGN PATENT DOCUMENTS

| | | | |
|---|---|---|---|
| EP | 2034538 | | 3/2009 |
| JP | 200511610 | | 1/2005 |
| JP | 2007123392 | | 5/2007 |
| JP | 2007254297 | | 10/2007 |
| JP | 2008074939 | | 4/2008 |
| JP | 2011249754 | | 12/2011 |
| JP | 2012502046 | | 1/2012 |
| JP | 2013028604 | | 2/2013 |
| JP | 2013128082 | | 6/2013 |
| JP | 2013539206 | | 10/2013 |
| KR | 10-2012-0032054 | | 4/2012 |
| KR | 2012032054 | * | 4/2012 |
| KR | 10-2012-0122813 | | 11/2012 |
| KR | 2012122813 | * | 11/2012 |
| WO | 2001039234 | | 5/2001 |
| WO | 2002002714 | | 1/2002 |
| WO | 200215645 | | 2/2002 |
| WO | 2003040257 | | 5/2003 |
| WO | 2003060956 | | 7/2003 |
| WO | 2004093207 | | 10/2004 |
| WO | 2004107822 | | 12/2004 |
| WO | 2005014551 | | 2/2005 |

(56) References Cited

FOREIGN PATENT DOCUMENTS

| | | |
|---|---|---|
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008044723 | 4/2008 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2014038867 | 3/2014 |

OTHER PUBLICATIONS

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)indium(III)Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylbory1)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NCN-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

(56) References Cited

OTHER PUBLICATIONS

Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Notice of Reasons for Rejection dated Mar. 27, 2018 for corresponding Japanese Patent Application No. 2014-252682.

\* cited by examiner

Formula I-A

Formula I-B

Formula I-C

METAL COMPLEX FOR PHOSPHORESCENT OLED

This application is a non-provisional of U.S. Provisional Application No. 61/916,552, filed Dec. 16, 2013. The disclosure of which is incorporated by reference in its entirety.

The claimed invention was made by, on behalf of, and/or in connection with one or more of the following parties to a joint university corporation research agreement: Regents of the University of Michigan, Princeton University. The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel iridium complexes that can be used in organic light emitting devices (OLEDs). The present invention relates to the iridium complexes, devices comprising the iridium complexes, and formulations comprising the iridium complexes.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices, organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

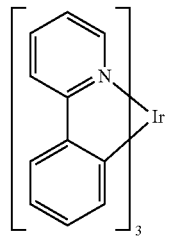

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

BRIEF SUMMARY OF THE INVENTION

A new class of heteroleptic Ir(III) complexes are provided.

The present invention provides compounds of formula I:

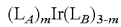

(I).

In the compound of formula I, $L_A$ is

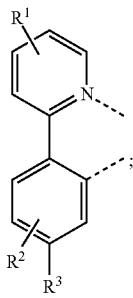

(II)

$L_B$ is selected from the group consisting of:

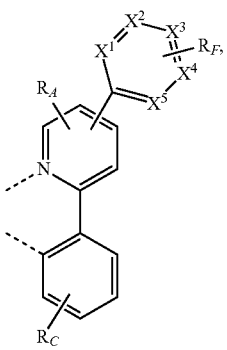

(III)

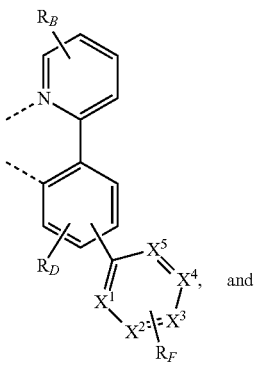

(IV)

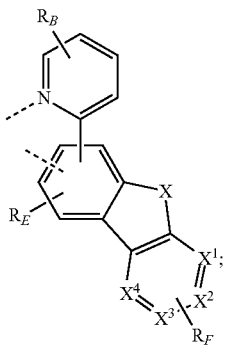

(V)

$R_E$ represents mono or di-substitution, or no substitution; $R^2$, $R_A$, and $R_D$ are each independently mono, di, or tri-substitution, or no substitution; $R^1$, $R_B$, $R_C$, and $R_F$ are each independently mono, di, tri, or tetra-substitution, or no substitution; $X^1$, $X^2$, $X^3$, $X^4$, and $X^5$ are each independently carbon or nitrogen; X is selected from the group consisting of O, S, and Se; $R^1$, $R^2$, $R_A$, $R_B$, $R_C$, $R_D$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrite, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, m is 2.
In some embodiments, X is O.
In some embodiments, $R^3$ is an alkyl having at least 2 carbons.
In some embodiments, $R^3$ is an alkyl having at least 3 carbons.
In some embodiments, $R^3$ is a cycloalkyl.
In some embodiments, $R^3$ is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, and cyclohexyl, wherein each is optionally partially or fully deuterated.
In some embodiments, $R^1$ is selected from the group consisting of hydrogen, deuterium, alkyl, cycloalkyl, and combinations thereof.
In some embodiments, $R^2$ represents no substitution.
In some embodiments, $R_F$ is selected from the group consisting of hydrogen, deuterium, alkyl, cycloalkyl, halogen, and combinations thereof. In some embodiments, $R_F$ is fluorine.

In some embodiments, $R_C$, $R_D$, and $R_E$ each represent no substitution.
In some embodiments, $L_B$ is selected from the group consisting of:
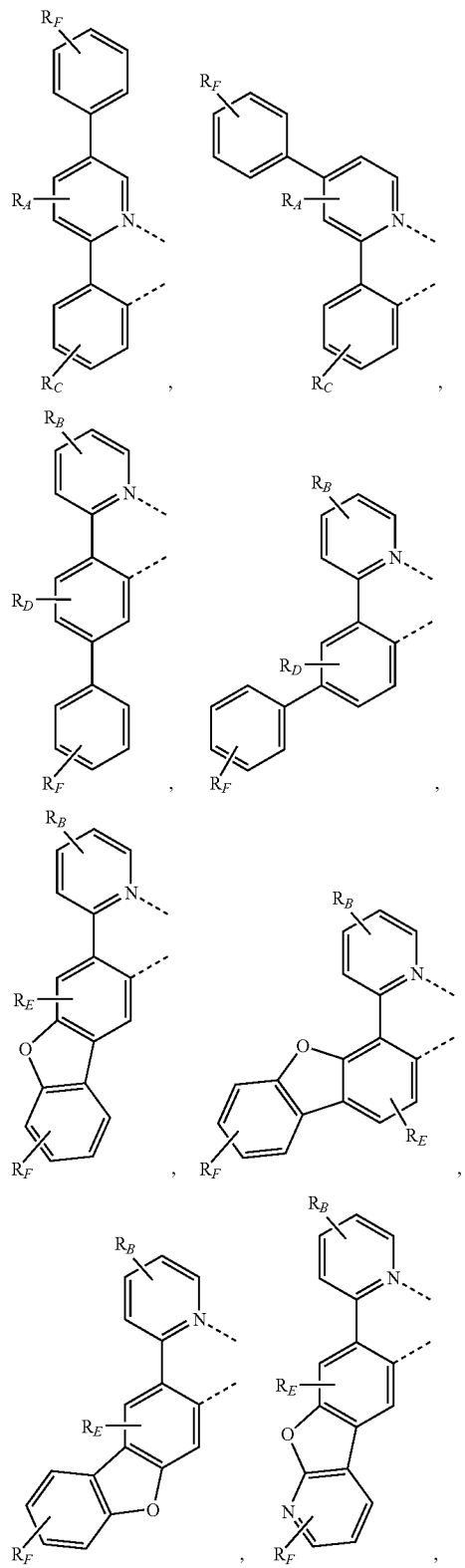
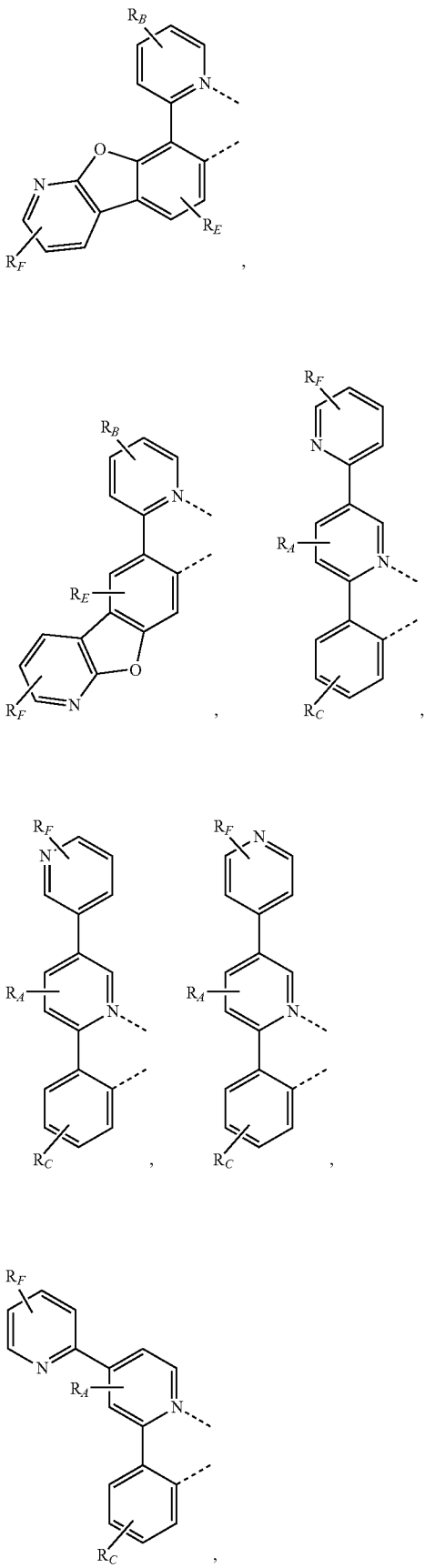

-continued

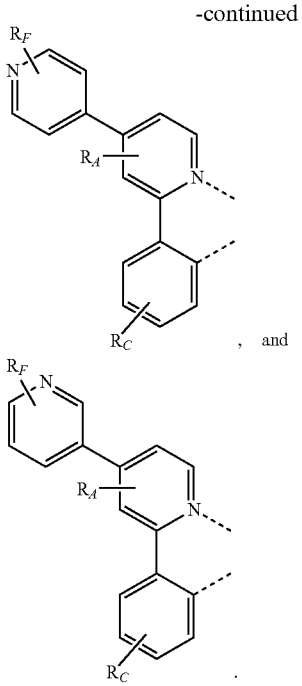

In some embodiments, $L_B$ is:

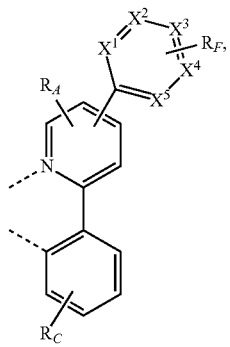

wherein $R_G$ represents mono, di, tri, or tetra-substitution, or no substitution; and wherein $R_G$ is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments wherein $L_B$ is formula VI, $R_B$ and $R_E$ represent no substitution; and $R_F$ and $R_G$ are each independently selected from the group consisting of hydrogen, deuterium, alkyl, cycloalkyl, halogen, and combinations thereof. In some embodiments wherein $L_B$ is formula VI, $R_G$ is fluorine.

In some embodiments, $L_A$ is selected from the group consisting of $L_{A1}$ to $L_{A86}$.

In some embodiments, $L_B$ is selected from the group consisting of $L_{B1}$ to $L_{B259}$.

In some embodiments, the compound of formula I is selected from the group consisting of Compound I-1 to Compound I-15.

In some embodiments, a first device is provided. The first device comprises an anode, a cathode, and an organic layer, disposed between the anode and the cathode, comprising a compound having the formula:

$$(L_A)_m Ir(L_B)_{3-m} \qquad (I).$$

In the compound of formula I, $L_A$ is

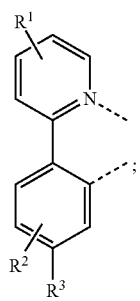

$L_B$ is selected from the group consisting of:

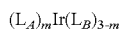

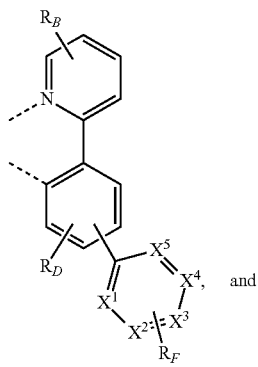

-continued

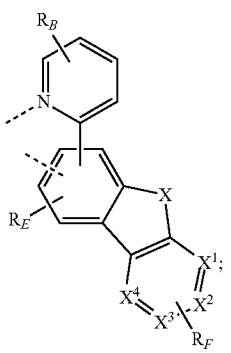

(V)

$R_E$ represents mono or di-substitution, or no substitution; $R^2$, $R_A$, and $R_D$ are each independently mono, di, or tri-substitution, or no substitution; $R^1$, $R_B$, $R_C$, and $R_F$ are each independently mono, di, tri, or tetra-substitution, or no substitution; $X^1$, $X^2$, $X^3$, $X^4$, and $X^5$ are each independently carbon or nitrogen; X is selected from the group consisting of O, S, and Se; $R^1$, $R^2$, $R_A$, $R_B$, $R_C$, $R_D$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, the first device is a consumer product.

In some embodiments, the first device is an organic light-emitting device.

In some embodiments, the first device comprises a lighting panel.

In some embodiments, the organic layer of the first device is an emissive layer and the compound is an emissive dopant. In some embodiments, the organic layer of the first device is an emissive layer and the compound is a non-emissive dopant.

In some embodiments, the organic layer of the first device further comprises a host.

In some embodiments, the host of the first device comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$—$Ar_2$, $C_nH_{2n}$—$Ar_1$, or no substitution; wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the host of the first device comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

In some embodiments, the host is selected from the group consisting of:

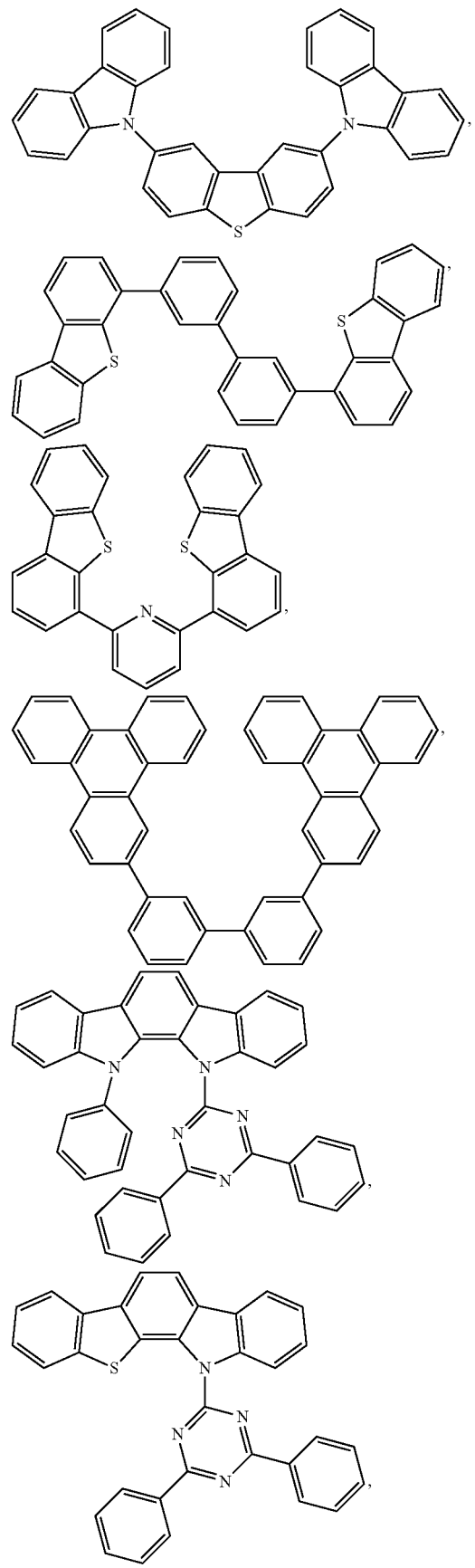

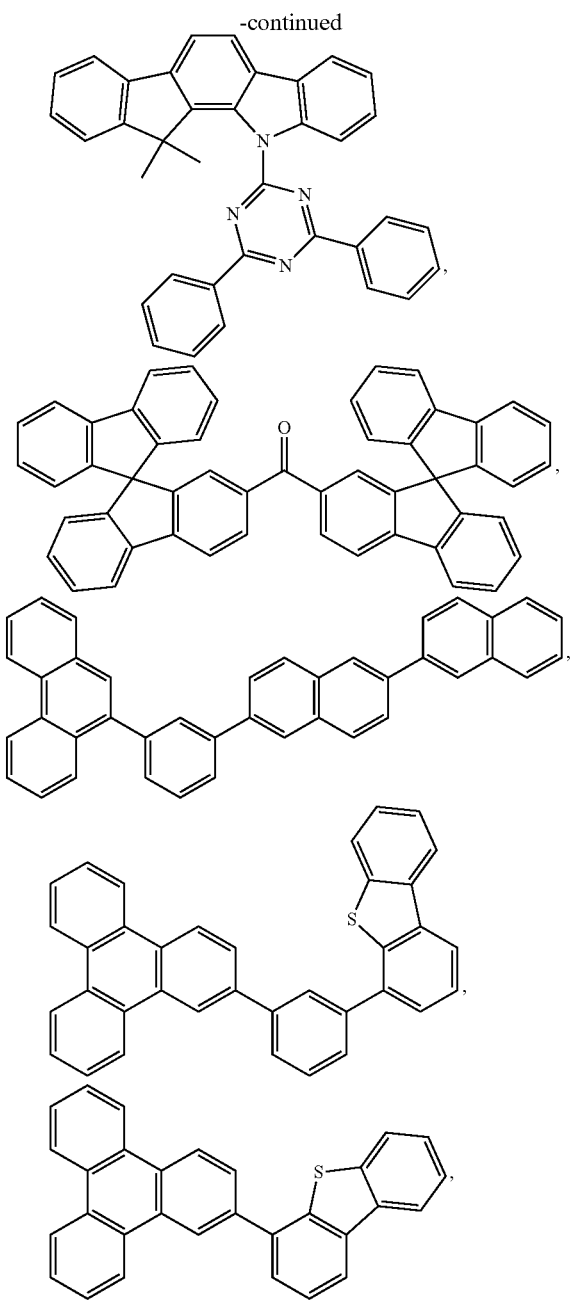

and combinations thereof.

In some embodiments, the host of the first device comprises a metal complex.

In some embodiments, a formulation comprising a compound of formula I is provided.

BRIEF DESCRIPTION OF THE DRAWINGS

The accompanying drawings, which are incorporated herein and form a part of the specification, illustrate embodiments of the present invention and, together with the description, further serve to explain the principles of the invention and to enable a person skilled in the pertinent art to make and use the invention.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
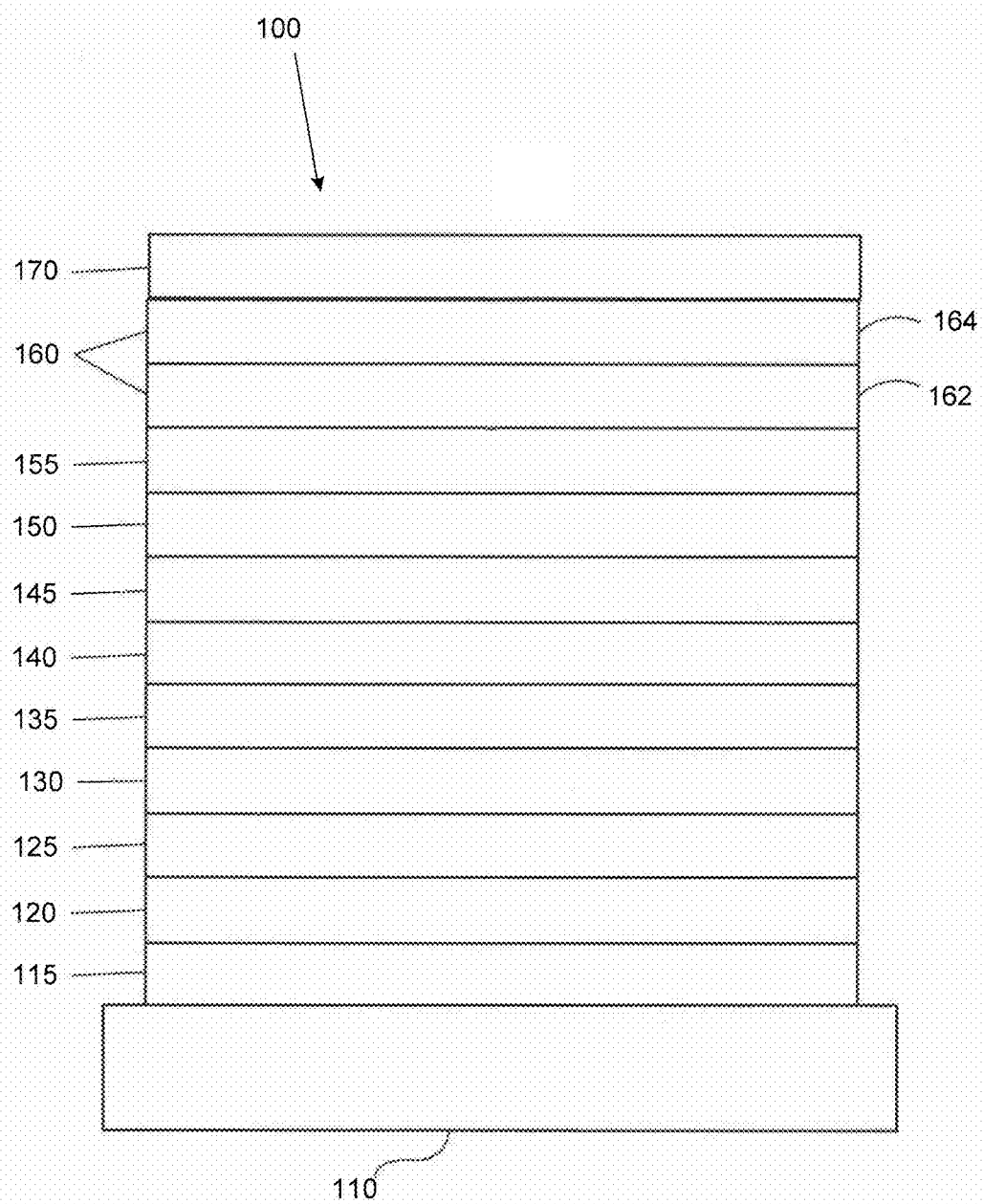
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
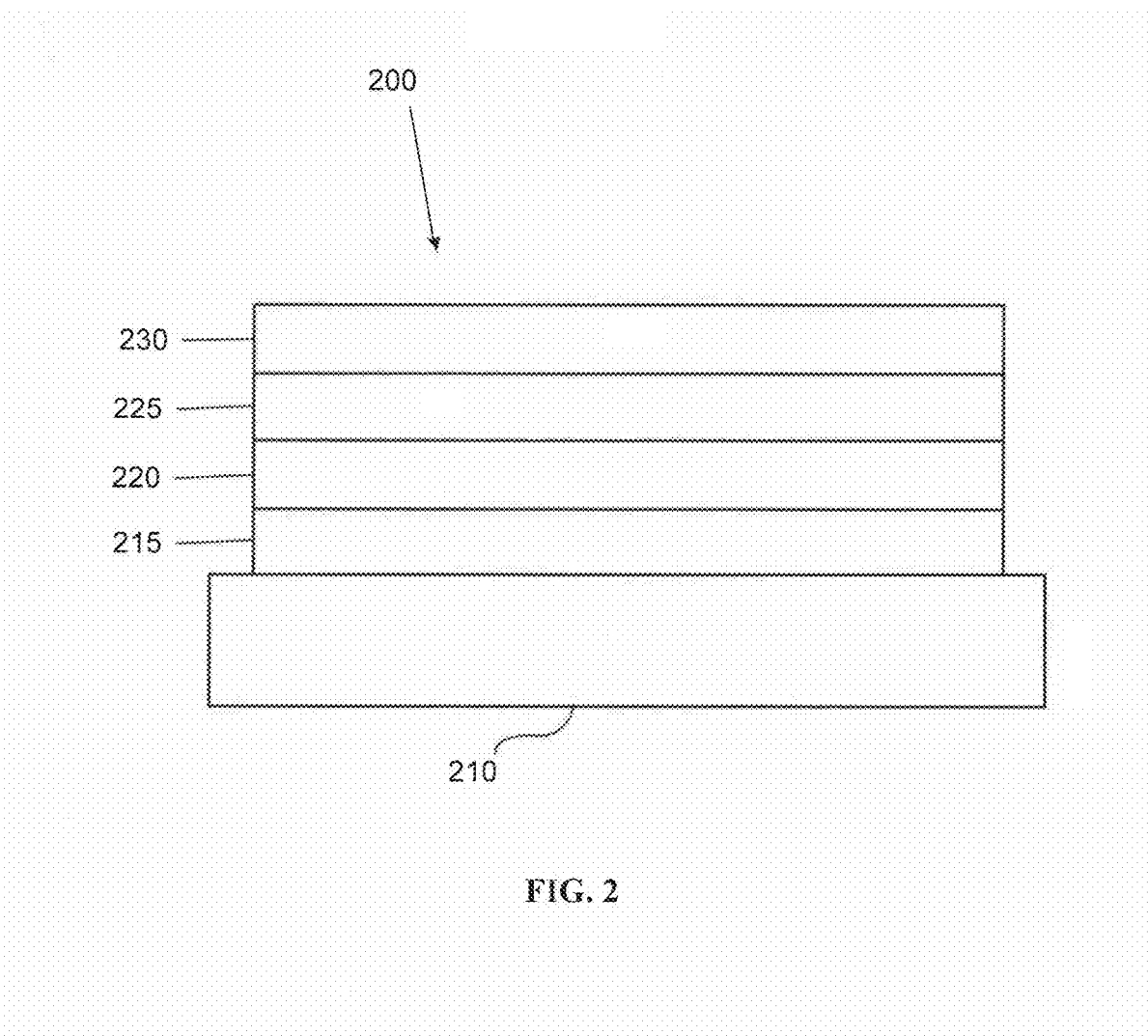
FIG. 2 shows an inverted organic light emitting device that does not have a separate electron transport layer.
Figure 3:
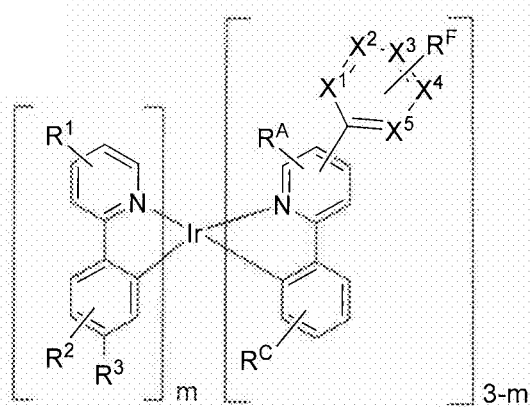
FIG. 3 shows a compound of Formula I-A.
Figure 4:
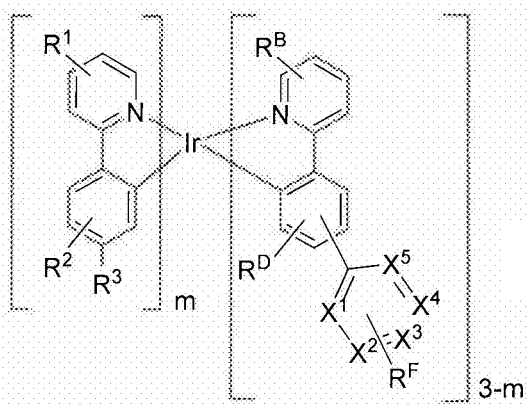
FIG. 4 shows a compound of Formula I-B.
Figure 5:
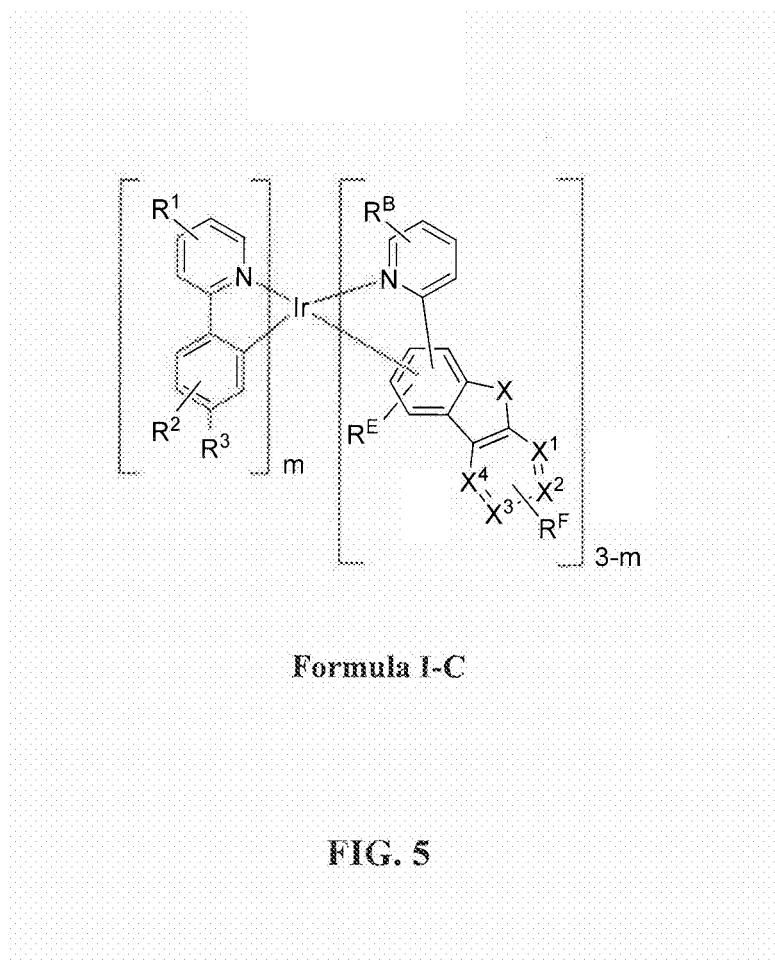
FIG. 5 shows a compound of Formula I-C.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In some embodiments, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material, in one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degrees C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein contemplates an alkyl group that has as a substituent an aromatic group. Additionally, the aralkyl group may be optionally substituted.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

As used herein, the term "substituted" indicates that a substituent other than hydrogen is bonded to the relevant carbon or nitrogen atom. Thus, where $R^1$ is mono-substituted, then one $R^1$ must be other than hydrogen. Similarly, where $R^1$ is di-substituted, then two of $R^1$ must be other than hydrogen. Similarly, where $R^1$ "represents no substitution," $R^1$ is hydrogen for all available positions.

Compounds are provided comprising a heteroleptic Ir(III) complex having extended conjugation. Heteroleptic iridium complexes are of great interest because their photophysical, thermal, and electronic properties can be tuned according to the ligands that are attached to the metal center. One advantage to using heteroleptic iridium complexes is that they offer improved device lifetime and a lower sublimation temperature, therefore offering improved manufacturing, as compared to homoleptic Ir(III) complexes. For example, a heteroleptic complex containing 2-phenylpyridine and 2-(biphenyl-3-yl)pyridine, has shown an improved lifetime compared to a related homoleptic complex. Further, the sublimation temperature of the heteroleptic complex is almost 70° C. lower than the homoleptic complex. See, U.S. Pat. No. 8,119,255. Heteroleptic complexes which demonstrate improved stability and low sublimation temperatures, such as those disclosed herein, are highly desirable for use in OLEDs. In particular, the heteroleptic Ir(III) complexes may be especially desirable for use in white organic light emitting devices (WOLEDs).

Iridium complexes containing alkyl substituted 2-phenylpyridine ligands have been used as emitters in phosphorescent OLEDs. Alkyl substitution at the 4-position on the phenyl ring of the 2-phenylpyridine ligand normally reduces the device efficiency. For example, devices with tris(2-(5-methyl-phenyl)pyridine)iridium(III) showed much lower external quantum efficiency (EQE) compared to tris(2-phenylpyridine)iridium(III). In the same device structure using 4,4'-di(9H-carbazol-9-yl)-1,1'-biphenyl (CBP) as host with 12% emitter doping concentration, a device with tris(2-(5-methyl-phenyl)pyridine)iridium(III) showed an EQE of 6.6%, whereas the device with tris(2-phenylpyridine)iridium(III) showed an EQE of 9.0%. Therefore, introduction of alkyl substitution at this position is not considered desirable. In the present invention, it was discovered that 4-alkyl substitution on the phenyl ring of the phenylpyridine ligand can improved device EQE in heteroleptic complexes.

In some embodiments, a compound having the formula:

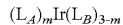  (I);

is provided. In the compound of formula I, $L_A$ is

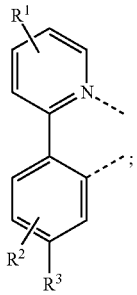 (II)

$L_B$ is selected from the group consisting of:

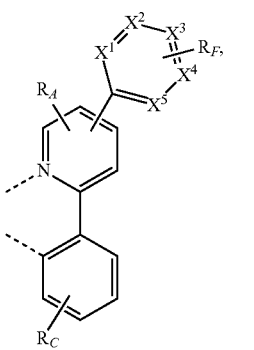 (III)

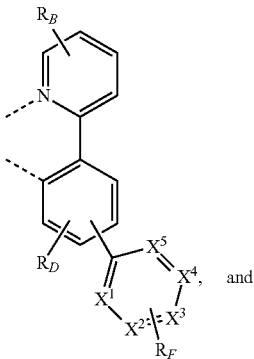 and (IV)

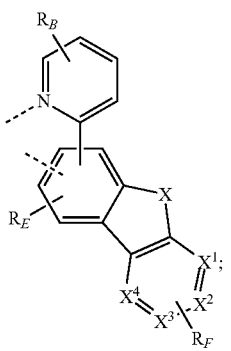 (V)

$R_E$ represents mono or di-substitution, or no substitution; $R^2$, $R_A$, and $R_D$ are each independently mono, di, or tri-substitution, or no substitution; $R^1$, $R_B$, $R_C$, and $R_F$ are each independently mono, di, tri, or tetra-substitution, or no substitution; $X^1$, $X^2$, $X^3$, $X^4$, and $X^5$ are each independently carbon or nitrogen; X is selected from the group consisting of O, S, and Se; $R^1$, $R^2$, $R_A$, $R_B$, $R_C$, $R_D$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, $L_B$ is selected from the group consisting of:

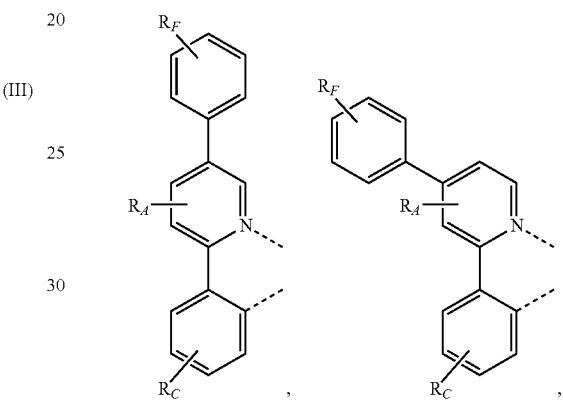

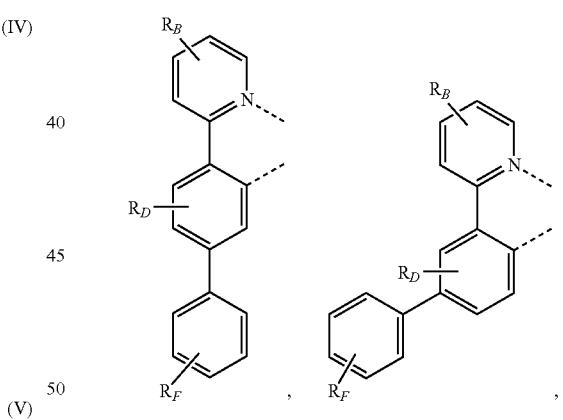

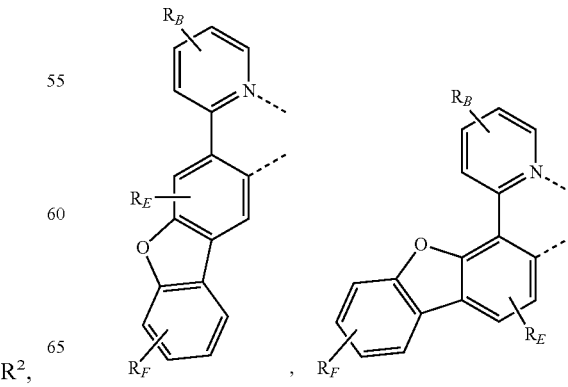

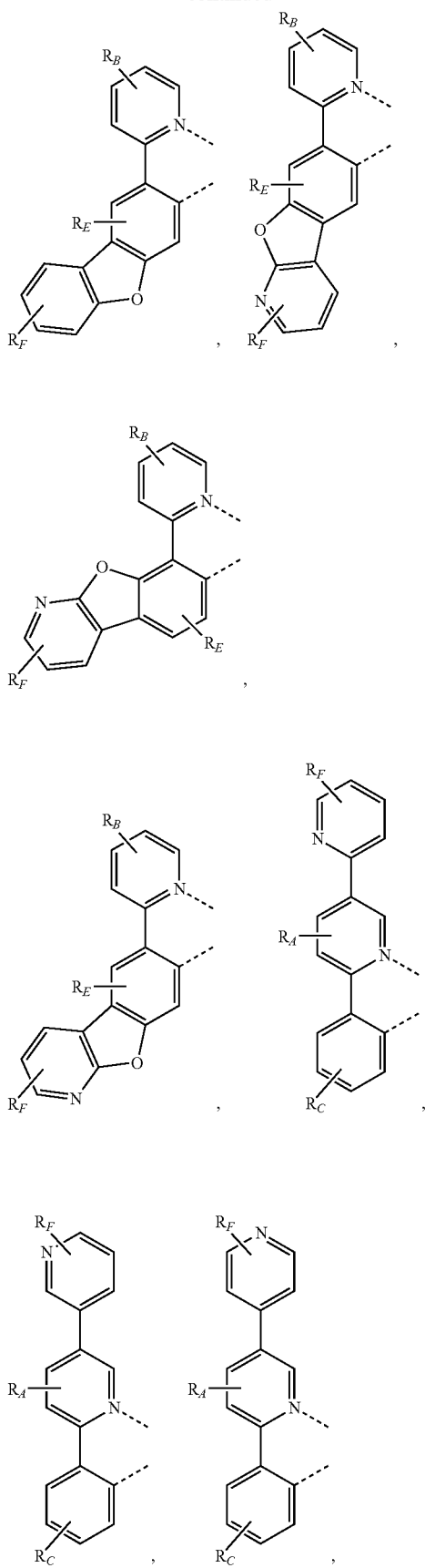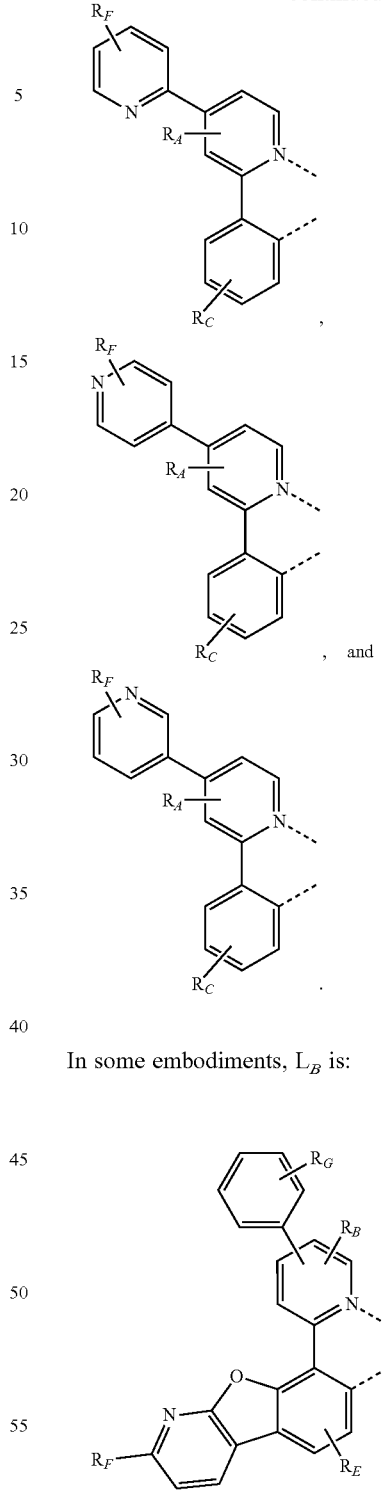

In some embodiments, $L_B$ is:

(VI)

wherein $R_G$ represents mono, di, tri, or tetra-substitution, or no substitution; and wherein $R_G$ is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments where $L_B$ is formula (VI), $R_B$ and $R_E$ represent no substitution; and $R_F$ and $R_G$ are each independently selected from the group consisting of hydrogen, deuterium, alkyl, cycloalkyl, halogen, and combinations thereof. In some embodiments where $L_B$ is formula (VI), $R_G$ is fluorine.

In some embodiments, $L_A$ is selected from the group consisting of $L_{A1}$ to $L_{A86}$ listed below:

$L_{A1}$
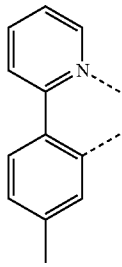

$L_{A2}$
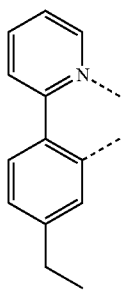

$L_{A3}$
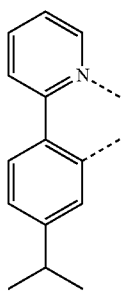

$L_{A4}$
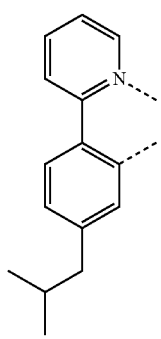

-continued $L_{A5}$
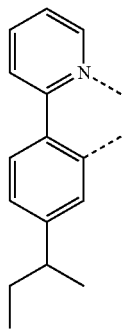

$L_{A6}$
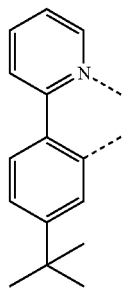

$L_{A7}$
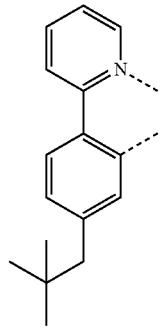

$L_{A8}$
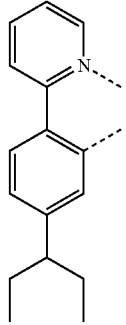

$L_{A9}$
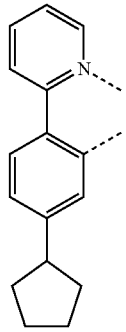

L_A10 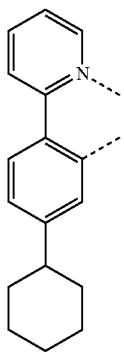 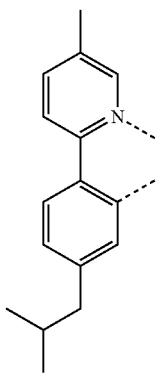
L_A11 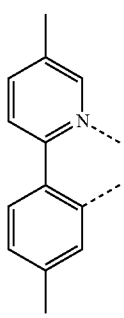 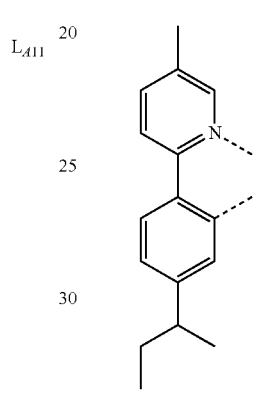
L_A12 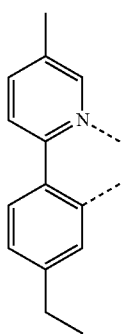 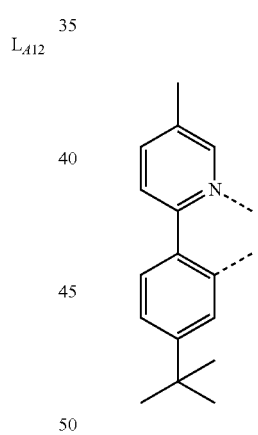
L_A13 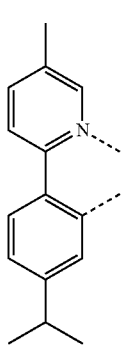 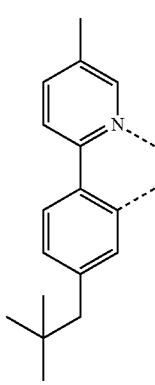
L_A14
L_A15
L_A16
L_A17

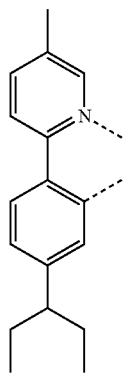
L_{A18}
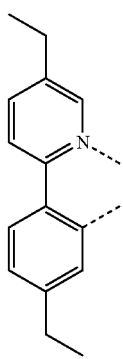
L_{A19}
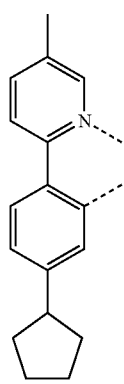
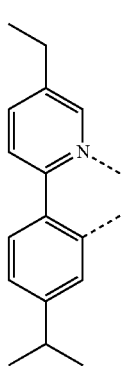
L_{A22}
L_{A23}
L_{A20}
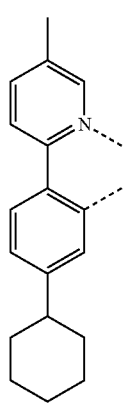
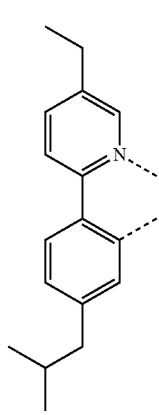
L_{A24}
L_{A21}
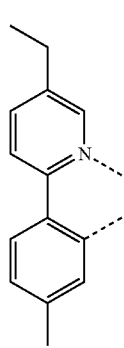
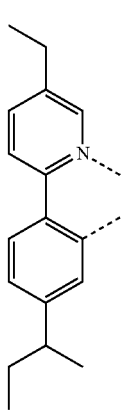
L_{A25}

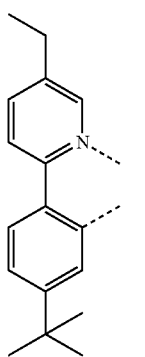
L_{A26}
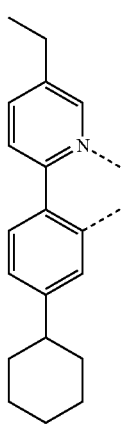
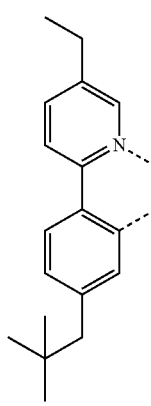
L_{A27}
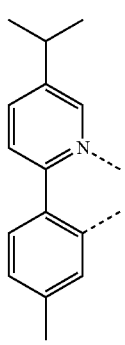
L_{A28}
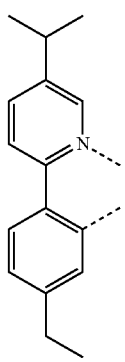
L_{A29}
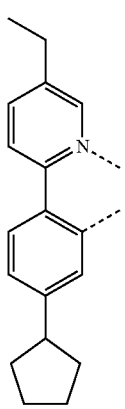
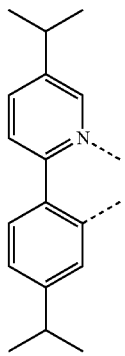
L_{A30}
L_{A31}
L_{A32}
L_{A33}

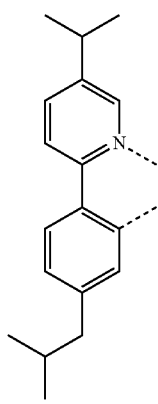
L<sub>A34</sub>
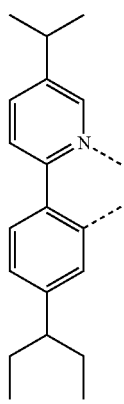
L<sub>A38</sub>
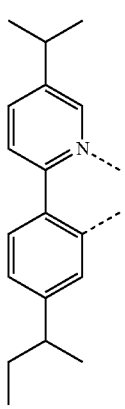
L<sub>A35</sub>
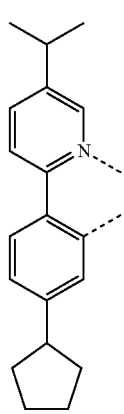
L<sub>A39</sub>
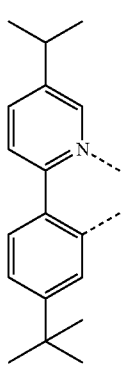
L<sub>A36</sub>
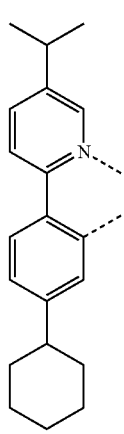
L<sub>A40</sub>
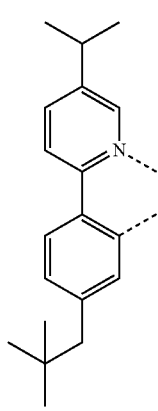
L<sub>A37</sub>
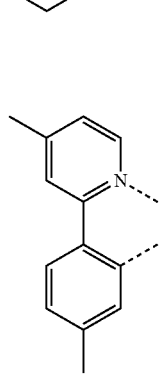
L<sub>A41</sub>

-continued
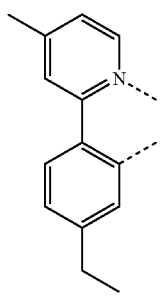
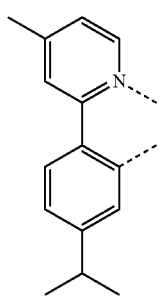
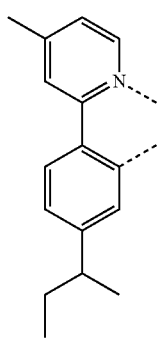
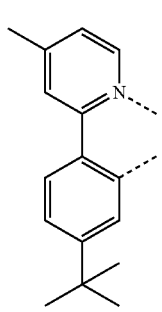
-continued
$L_{A42}$
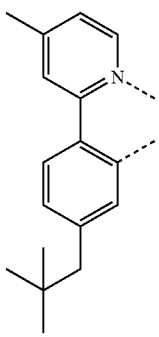
$L_{A43}$
$L_{A44}$
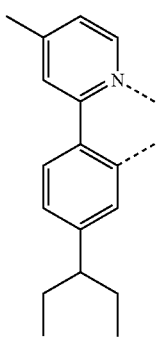
$L_{A45}$
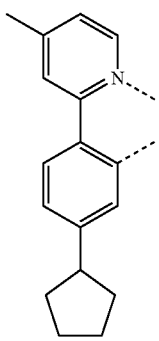
$L_{A46}$
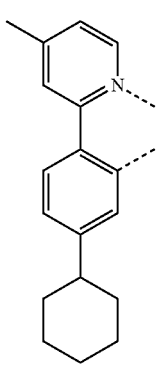
$L_{A47}$
$L_{A48}$
$L_{A49}$
$L_{A50}$

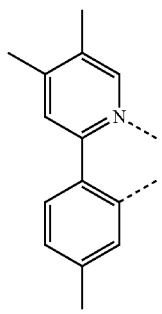
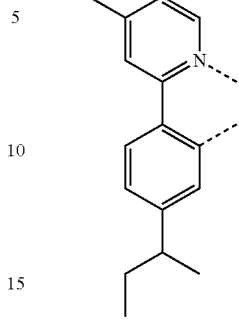
L<sub>A51</sub>
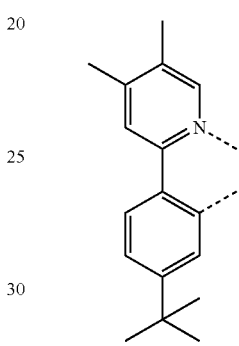
L<sub>A52</sub>
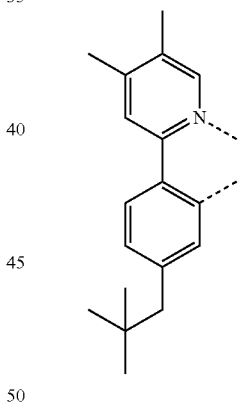
L<sub>A53</sub>
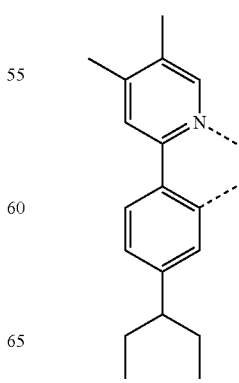
L<sub>A54</sub>
L<sub>A55</sub>
L<sub>A56</sub>
L<sub>A57</sub>
L<sub>A58</sub>

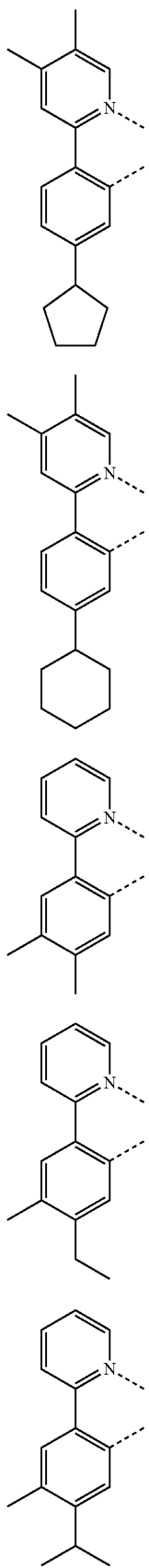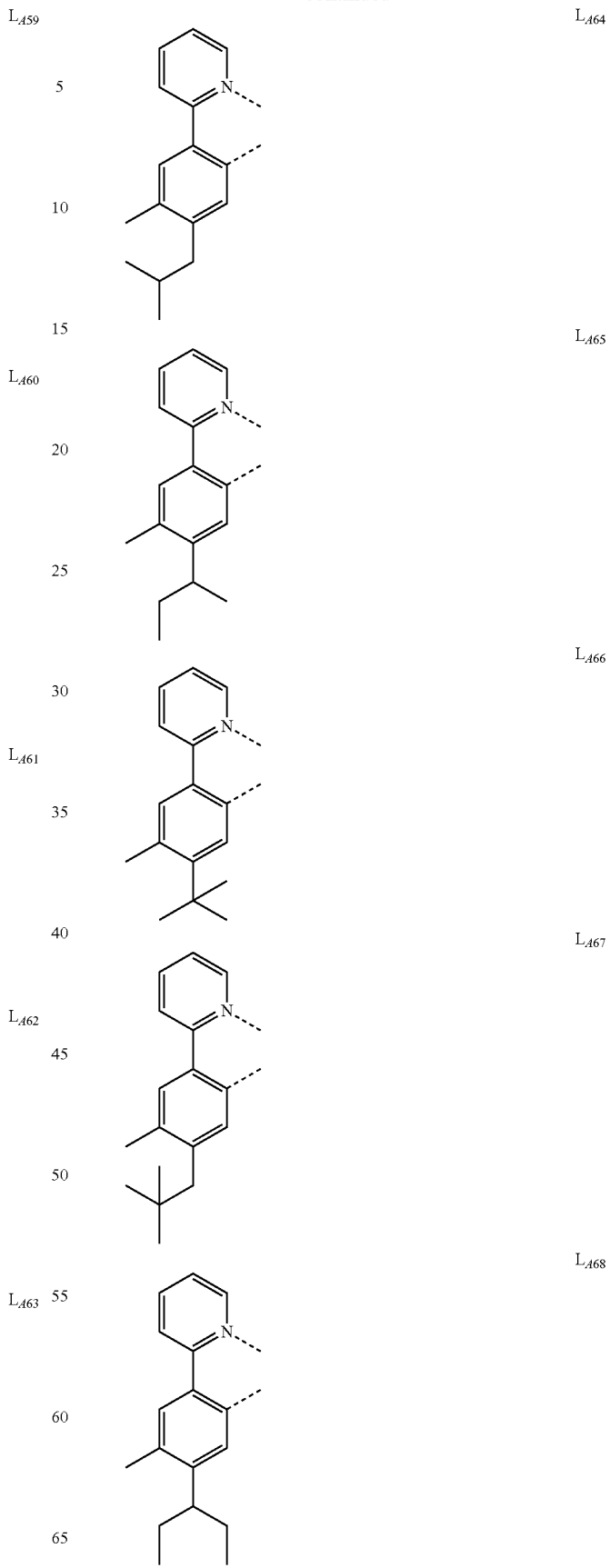

L_A69 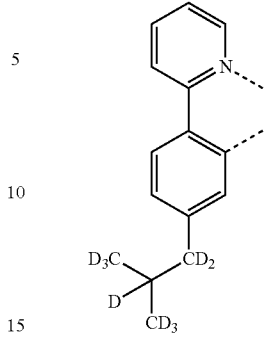
L_A70
L_A71 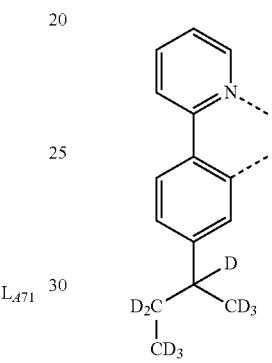
L_A72 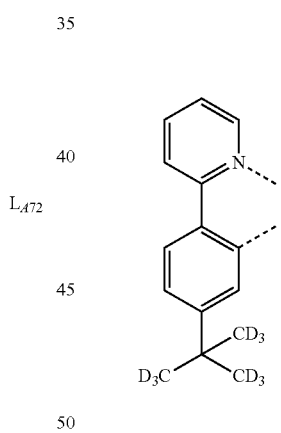
L_A73 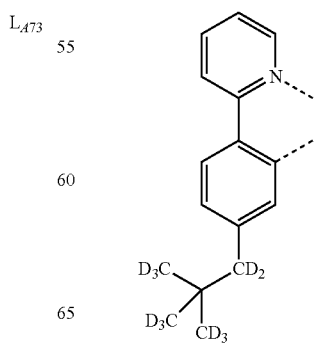
L_A74
L_A75
L_A76
L_A77
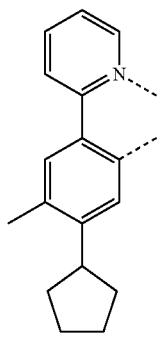
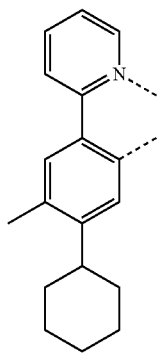
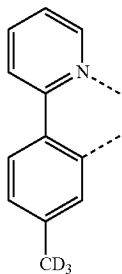
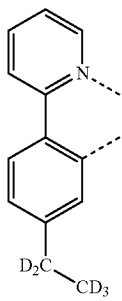
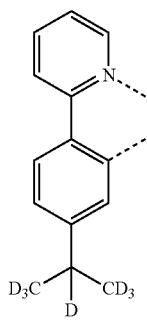

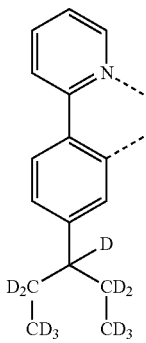
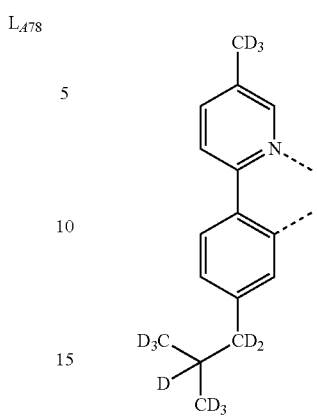
L<sub>A78</sub>
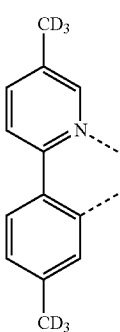
L<sub>A79</sub>
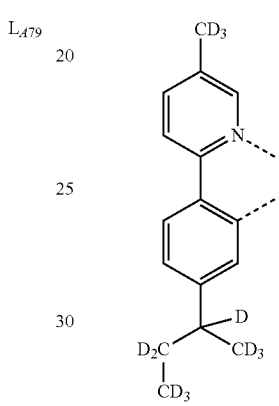
L<sub>A83</sub>
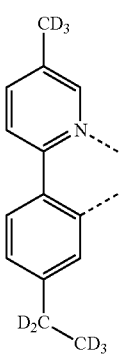
L<sub>A80</sub>
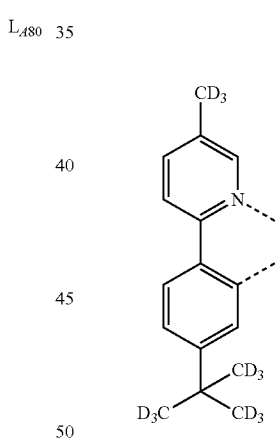
L<sub>A84</sub>
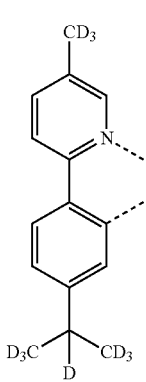
L<sub>A81</sub>
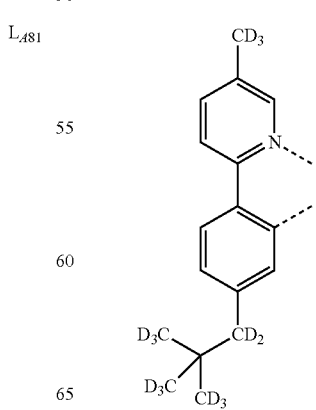
L<sub>A85</sub>
and

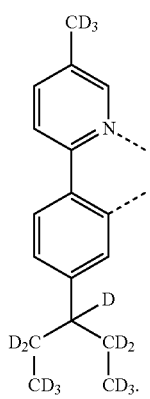
L_{A86}
In some embodiments, $L_A$ is selected from the group consisting of $L_{A87}$ to $L_{A172}$ listed below:
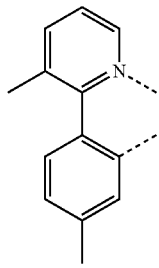
L_{A87}
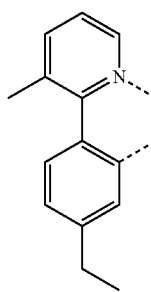
L_{A88}
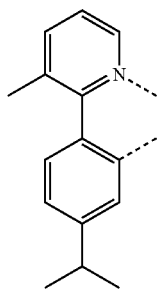
L_{A89}
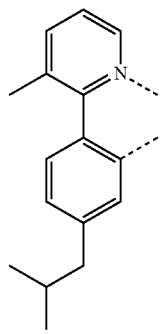
L_{A90}
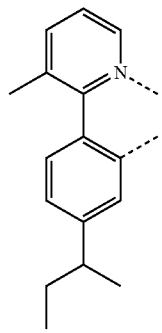
L_{A91}
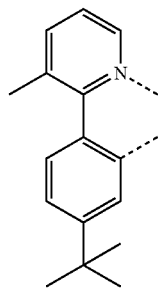
L_{A92}
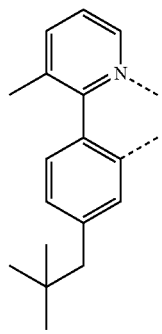
L_{A93}
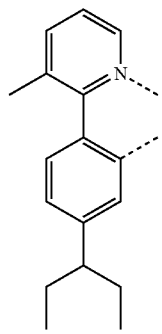
L_{A94}

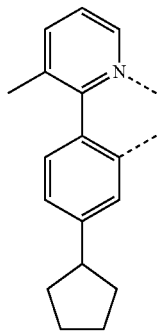
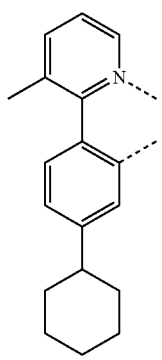
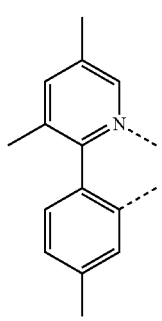
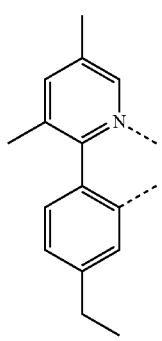
L$_{A95}$
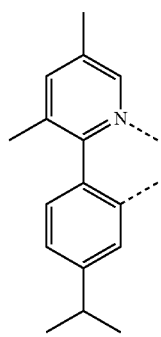
L$_{A96}$
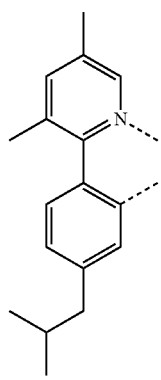
L$_{A97}$
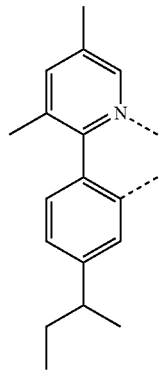
L$_{A98}$
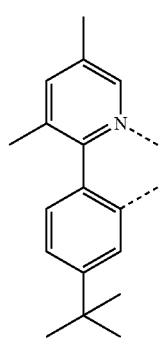
L$_{A99}$
L$_{A100}$
L$_{A101}$
L$_{A102}$ -continued
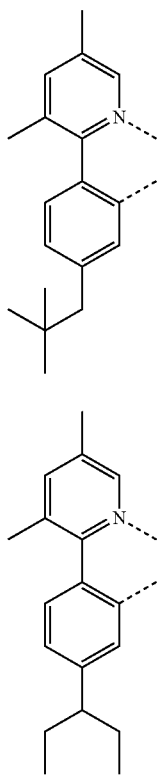
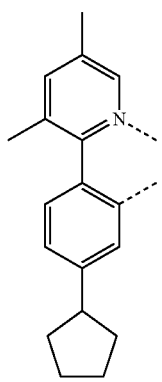
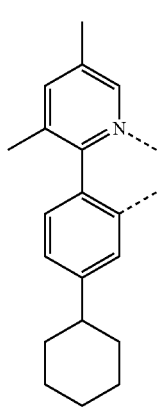
-continued
L$_{A103}$
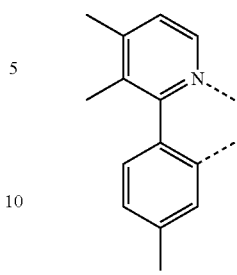
L$_{A104}$
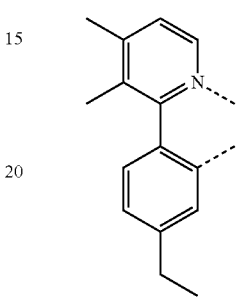
L$_{A105}$
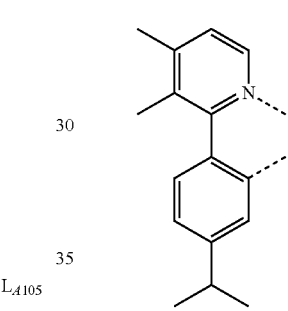
L$_{A106}$
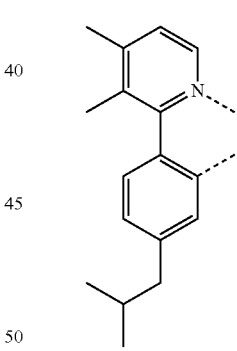
L$_{A107}$
L$_{A108}$
L$_{A109}$
L$_{A110}$
L$_{A111}$ -continued
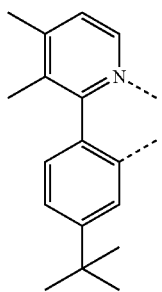
L<sub>A112</sub>
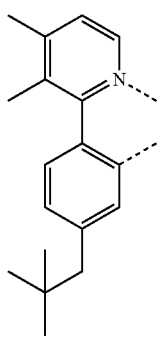
L<sub>A113</sub>
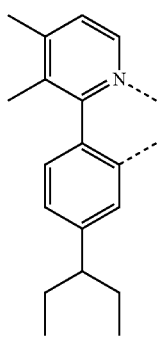
L<sub>A114</sub>
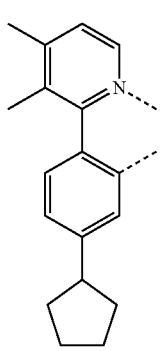
L<sub>A115</sub>
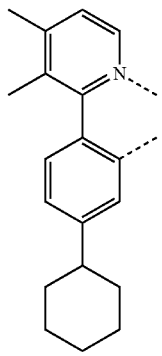
L<sub>A116</sub>
L<sub>A117</sub>
L<sub>A118</sub>
L<sub>A119</sub>

L<sub>A120</sub>
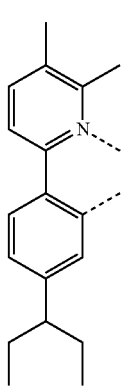
L<sub>A124</sub>
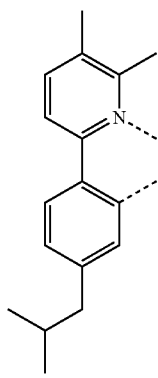
L<sub>A121</sub>
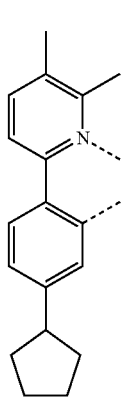
L<sub>A125</sub>
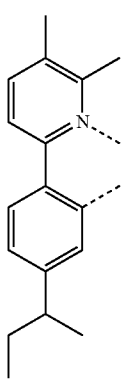
L<sub>A122</sub>
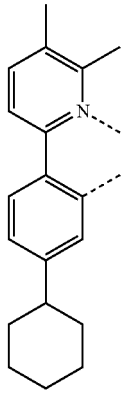
L<sub>A126</sub>
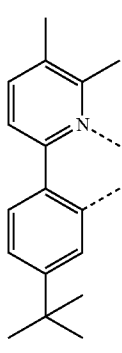
L<sub>A123</sub>
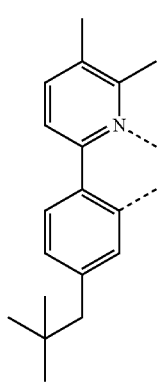
L<sub>A127</sub>
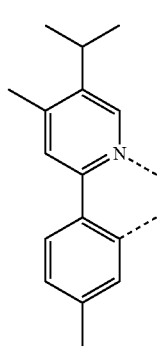

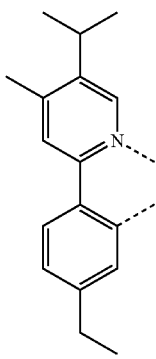
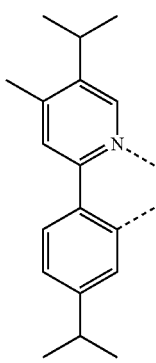
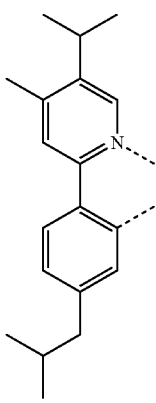
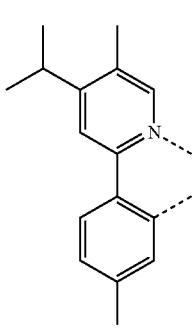
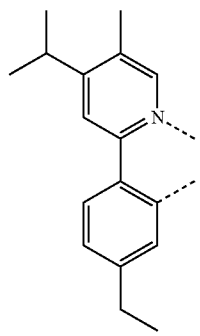
$L_{A128}$
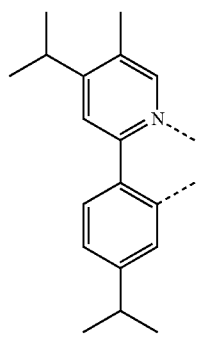
$L_{A129}$
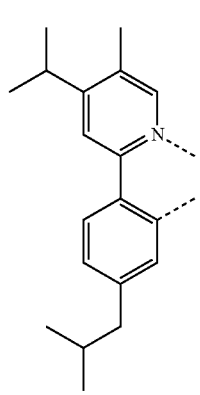
$L_{A130}$
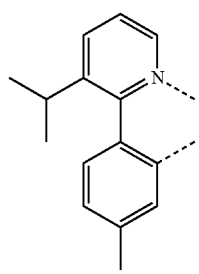
$L_{A131}$
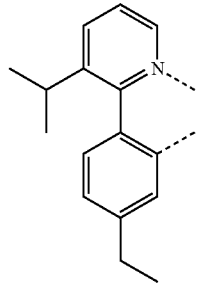
$L_{A132}$
$L_{A133}$
$L_{A134}$
$L_{A135}$
$L_{A136}$ L$_{A137}$ 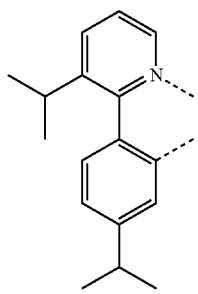
L$_{A138}$ 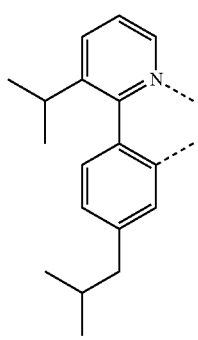
L$_{A139}$ 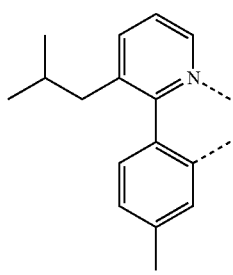
L$_{A140}$ 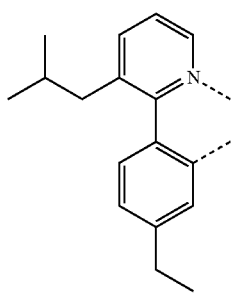
L$_{A141}$ 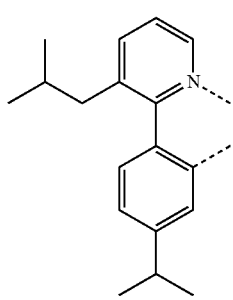
L$_{A142}$ 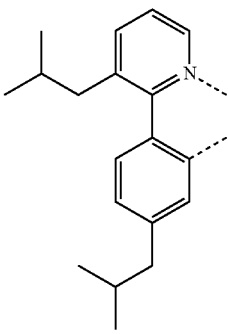
L$_{A143}$ 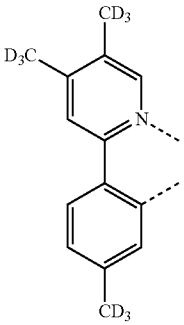
L$_{A144}$
L$_{A145}$ 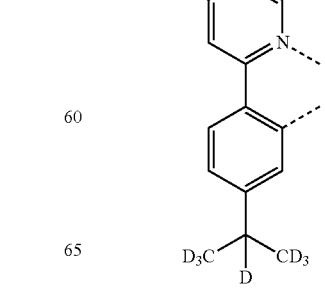

L<sub>A146</sub> 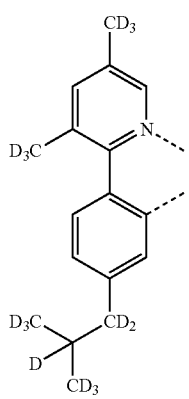
L<sub>A147</sub> 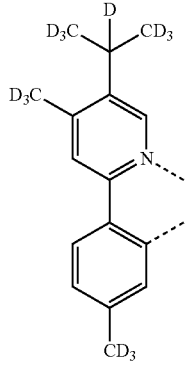
L<sub>A148</sub> 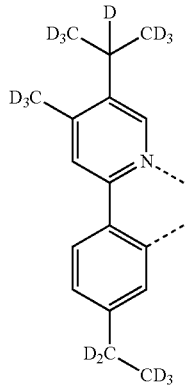
L<sub>A149</sub> 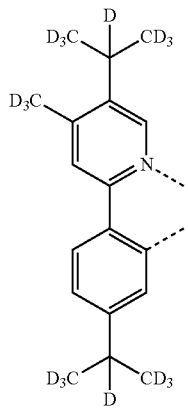
L<sub>A150</sub> 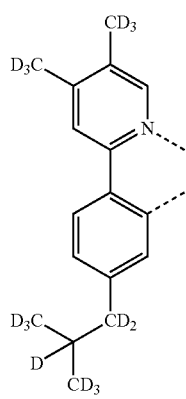
L<sub>A151</sub> 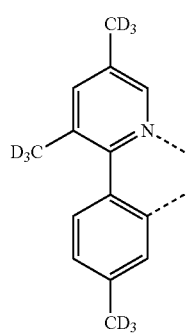
L<sub>A152</sub> 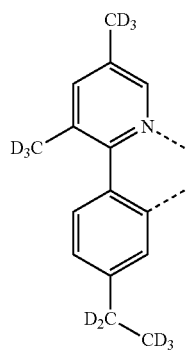
L<sub>A153</sub> 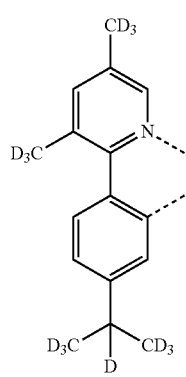

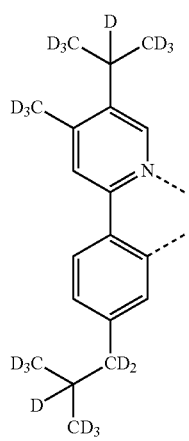
L_A154
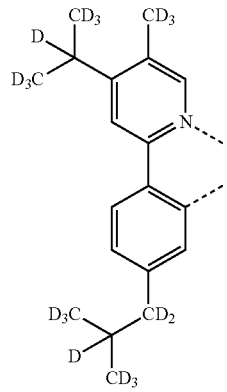
L_A155
L_A156
L_A157
L_A158
L_A159
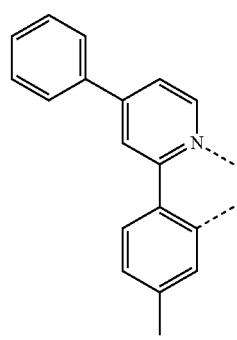
L_A160
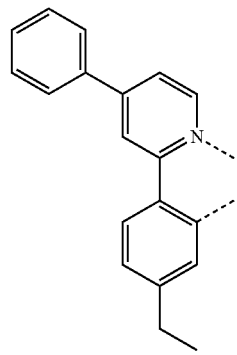
L_A161
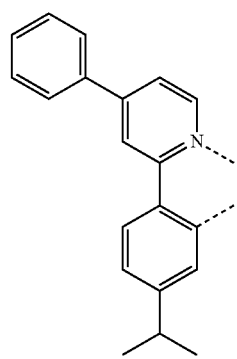

L<sub>A</sub>162
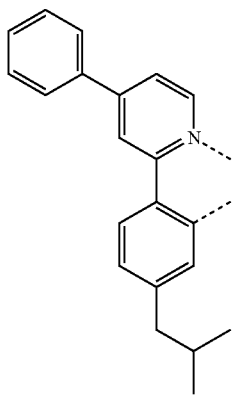
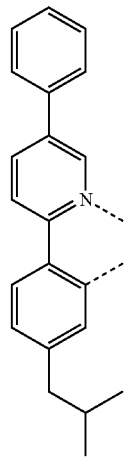
L<sub>A</sub>163
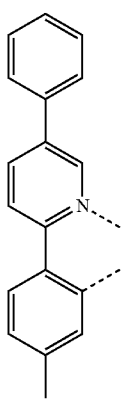
L<sub>A</sub>164
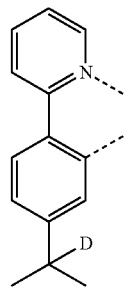
L<sub>A</sub>165
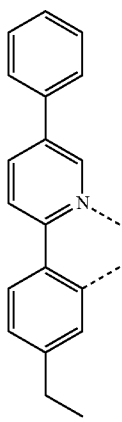
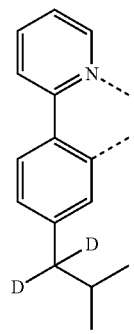
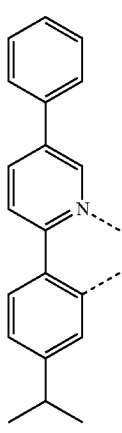
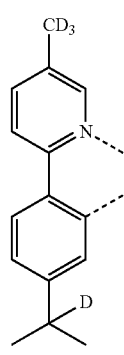
L<sub>A</sub>166
L<sub>A</sub>167
L<sub>A</sub>168
L<sub>A</sub>169

-continued

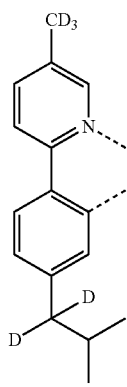

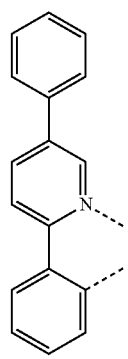
$L_{A170}$

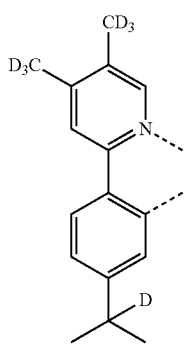
and

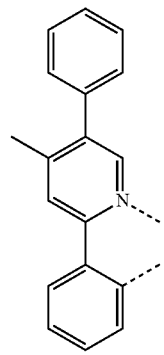
$L_{A171}$

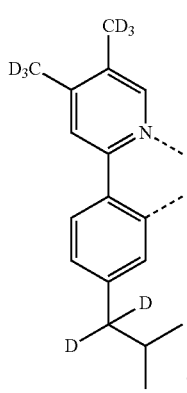

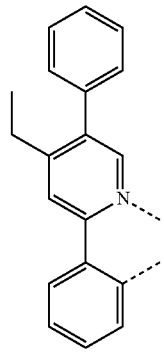
$L_{A172}$

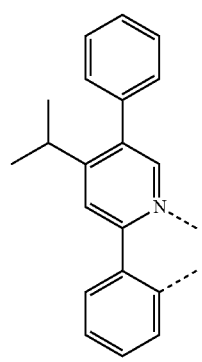

$L_{B1}$ $L_{B2}$ $L_{B3}$ $L_{B4}$

In some embodiments, $L_A$ is selected from the group consisting of $L_{A1}$, $L_{A2}$, $L_{A3}$, $L_{A4}$, $L_{A5}$, and $L_{A61}$. In some embodiments, $L_A$ is $L_{A1}$. In some embodiments, $L_A$ is $L_{A2}$. In some embodiments, $L_A$ is $L_{A3}$. In some embodiments, $L_A$ is $L_{A4}$. In some embodiments, $L_A$ is $L_{A5}$. In some embodiments, $L_A$ is $L_{A61}$.

In some embodiments, $L_B$ is selected from the group consisting of $L_{B1}$ to $L_{B259}$ listed below:

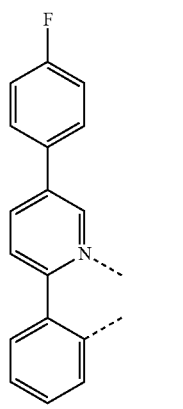

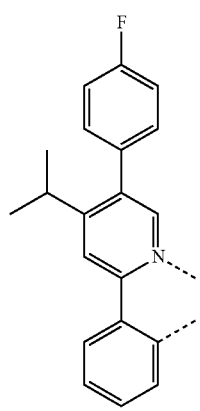
L$_{B5}$
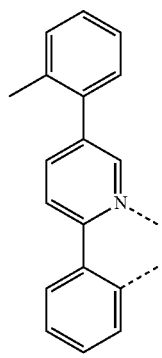
L$_{B6}$
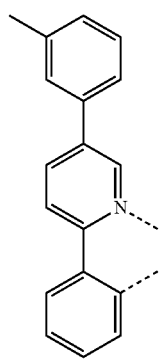
L$_{B7}$
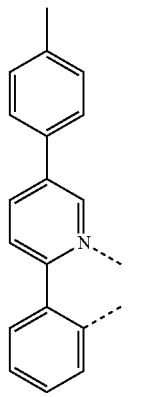
L$_{B8}$
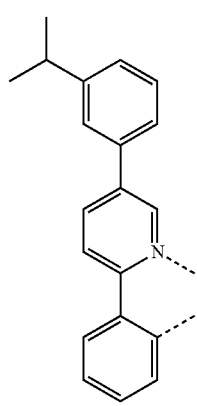
L$_{B9}$
L$_{B10}$
L$_{B11}$
L$_{B12}$

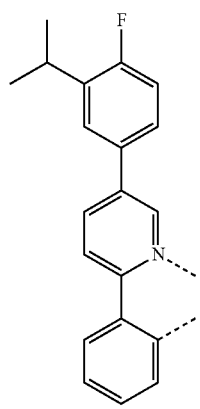
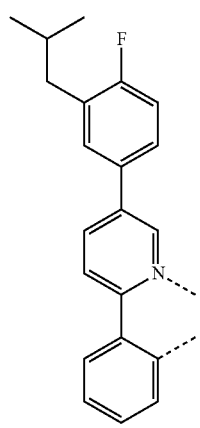
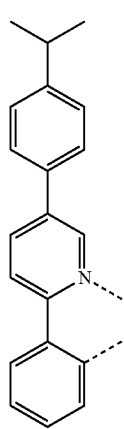
$L_{B13}$
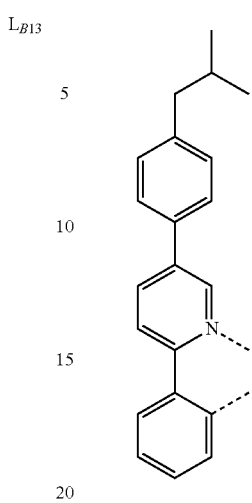
$L_{B14}$
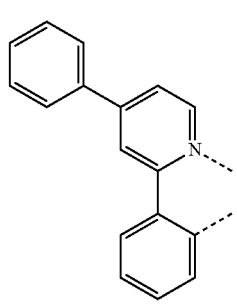
$L_{B15}$
$L_{B16}$
$L_{B17}$
$L_{B18}$
$L_{B19}$
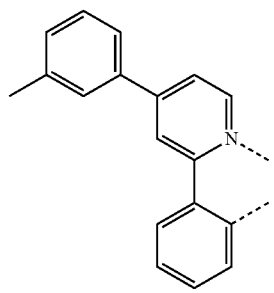

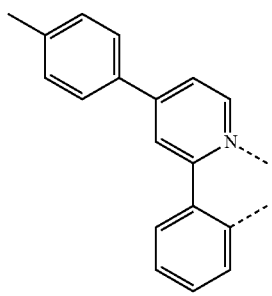
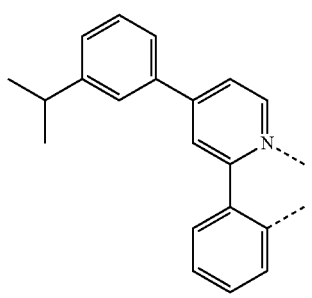

L$_{B20}$
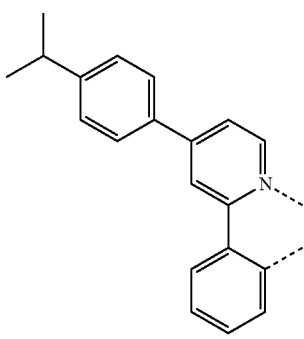
L$_{B21}$
L$_{B22}$
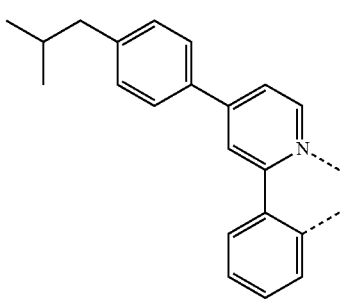
L$_{B23}$
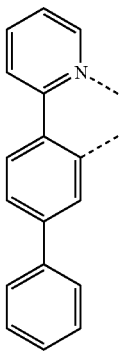
L$_{B24}$
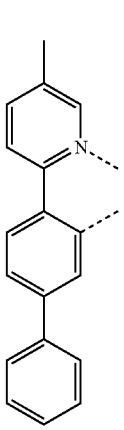
L$_{B25}$
L$_{B26}$
L$_{B27}$
L$_{B28}$

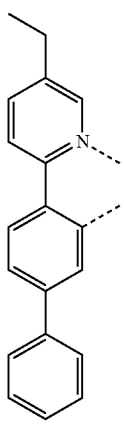 L_B28

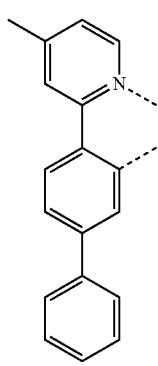 
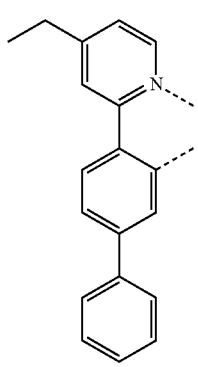 
L_B29 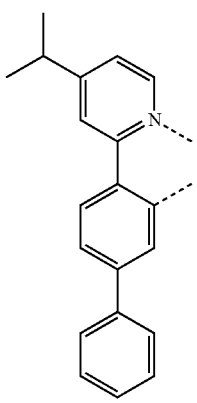
L_B30 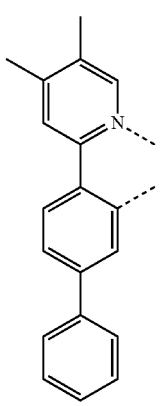
L_B31 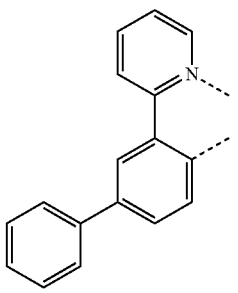
L_B32 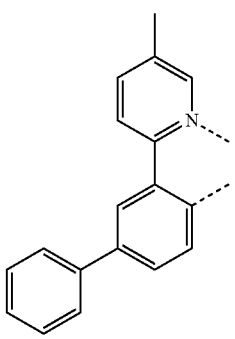
L_B33
L_B34
L_B35
L_B36

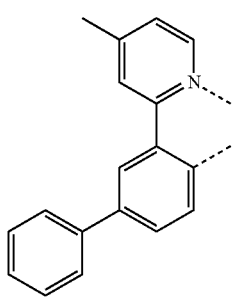
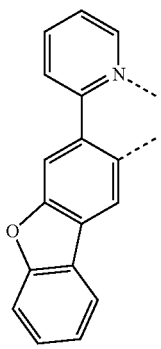
L$_{B37}$
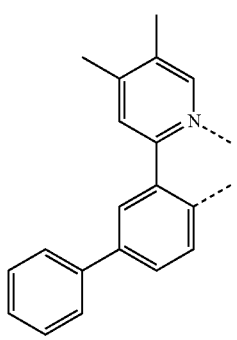
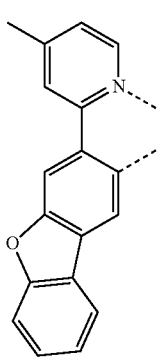
L$_{B38}$
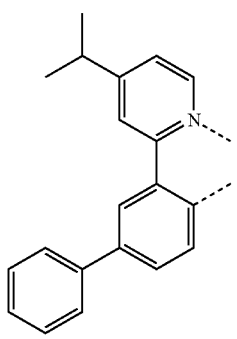
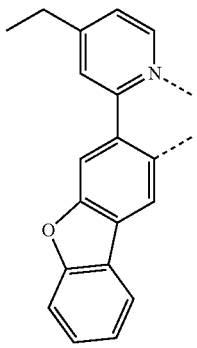
L$_{B39}$
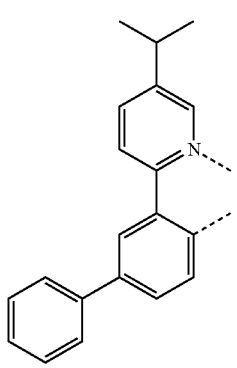
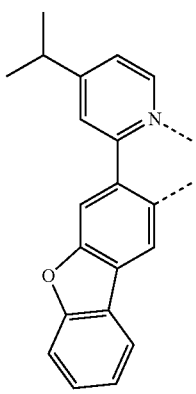
L$_{B40}$
L$_{B41}$
L$_{B42}$
L$_{B43}$
L$_{B44}$ L<sub>B45</sub> 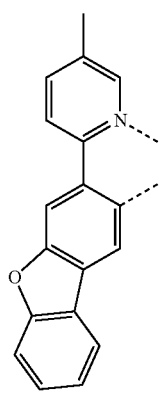 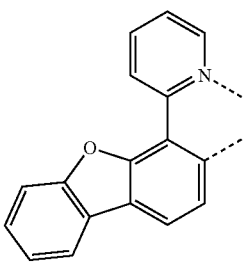 L<sub>B49</sub>
L<sub>B46</sub> 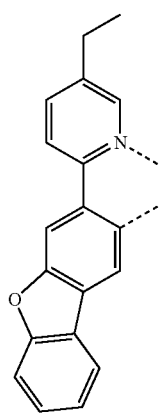 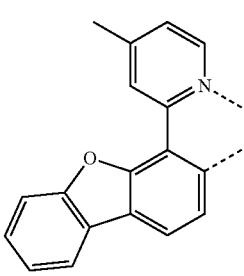 L<sub>B50</sub>
L<sub>B47</sub> 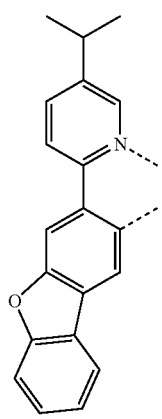 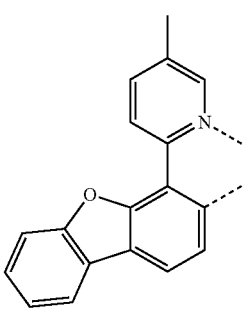 L<sub>B51</sub>
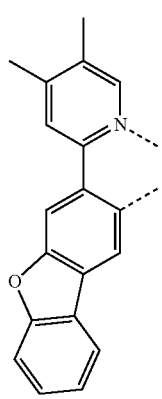 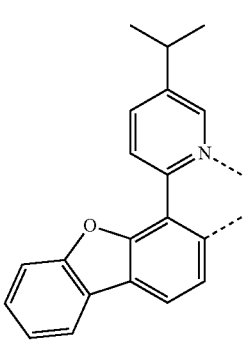 L<sub>B52</sub>
L<sub>B48</sub>
L<sub>B53</sub>

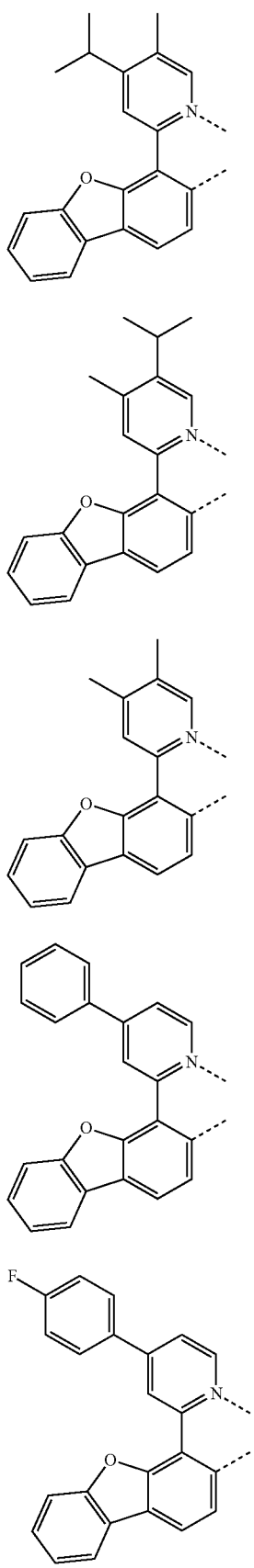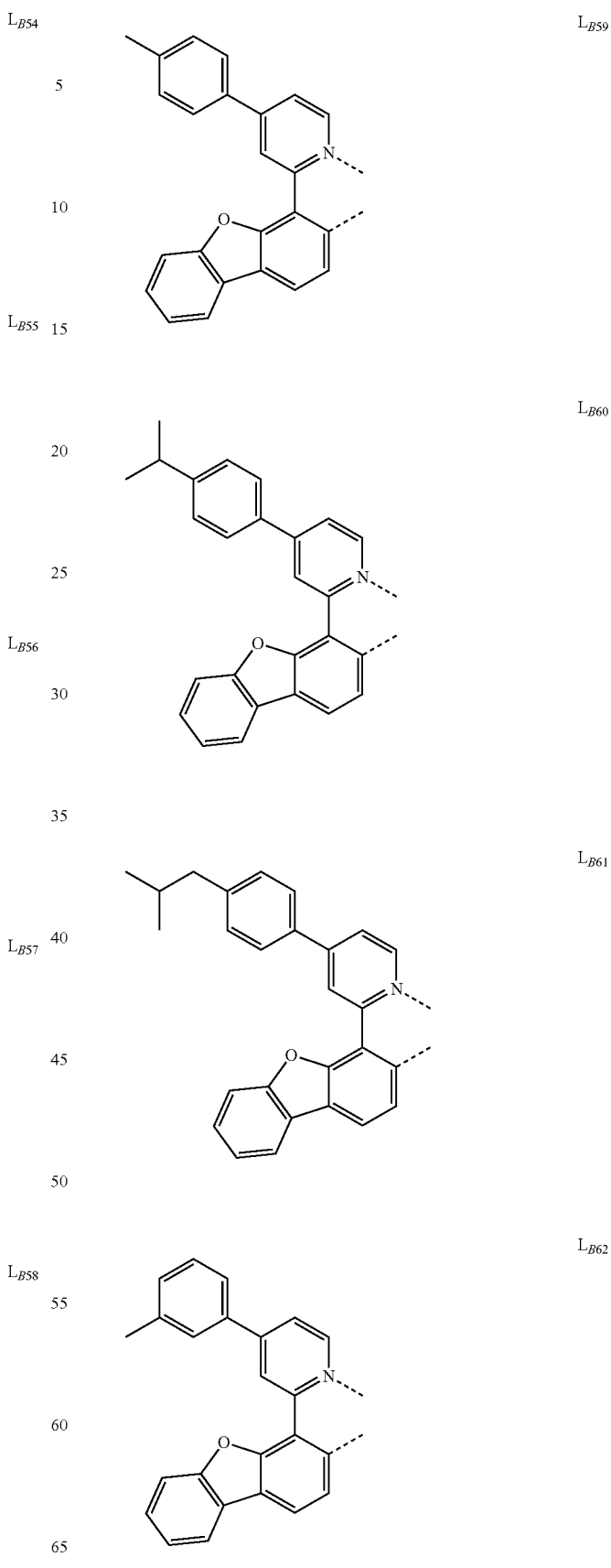

-continued
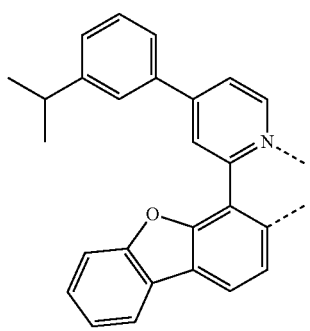
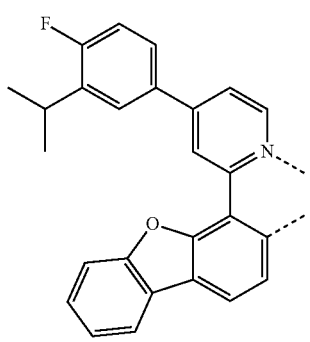
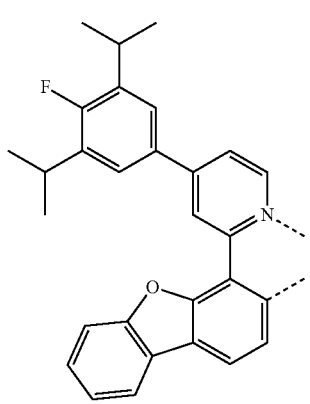
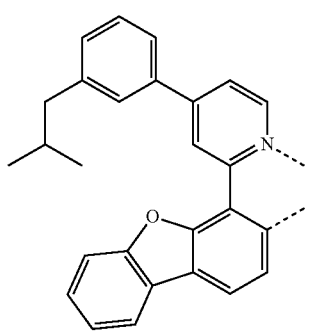
-continued
L<sub>B63</sub>
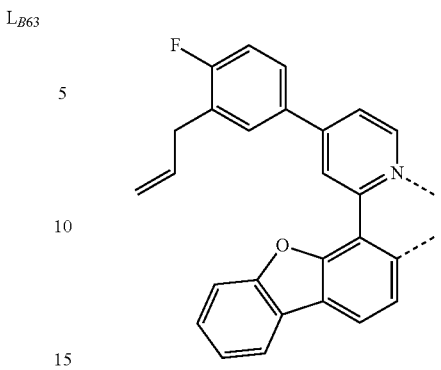
L<sub>B64</sub>
L<sub>B65</sub>
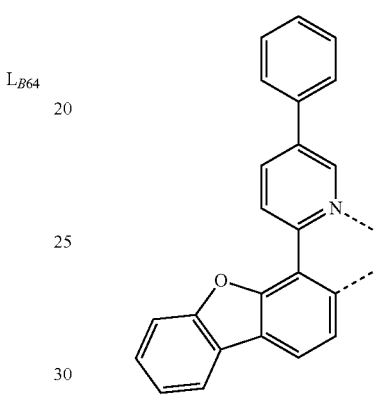
L<sub>B66</sub>
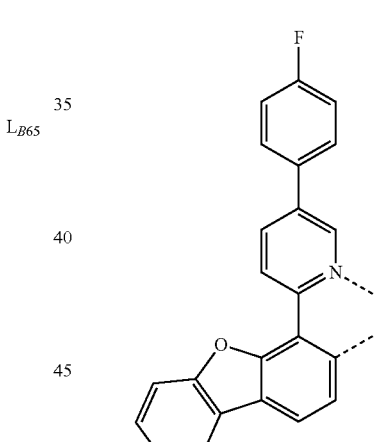
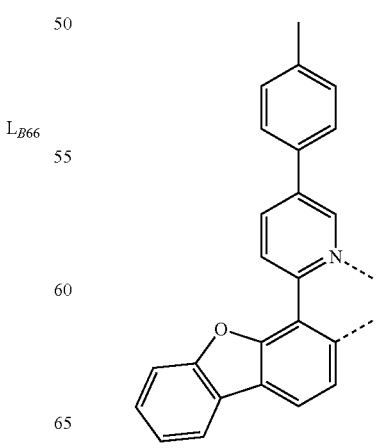
L<sub>B67</sub>
L<sub>B68</sub>
L<sub>B69</sub>
L<sub>B70</sub>

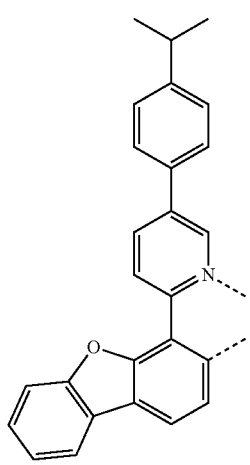
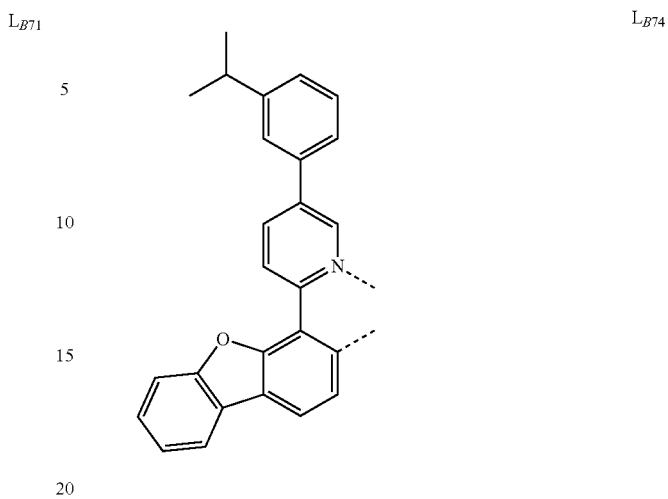
L<sub>B71</sub>
L<sub>B72</sub>
L<sub>B73</sub>
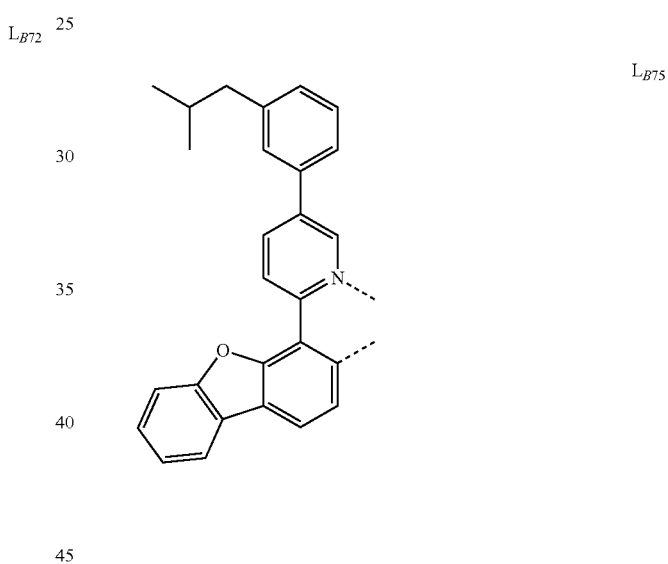
L<sub>B74</sub>
L<sub>B75</sub>
L<sub>B76</sub>
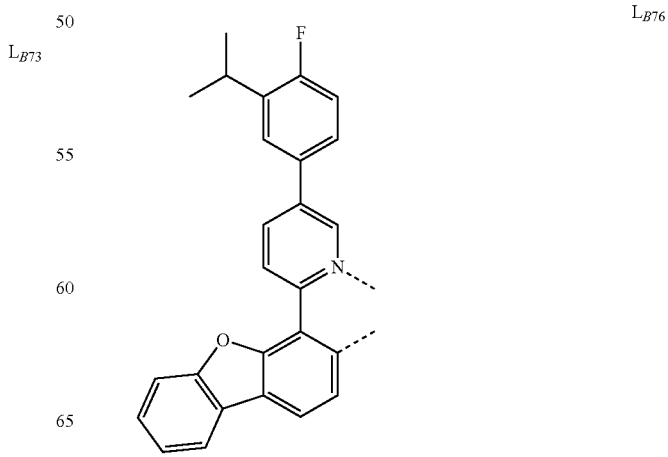

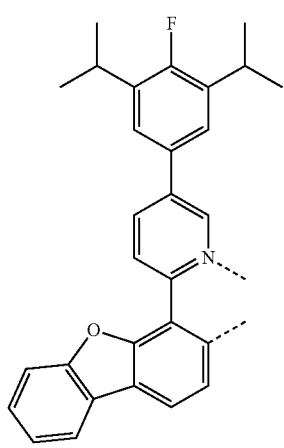
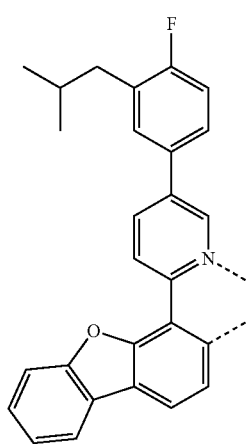
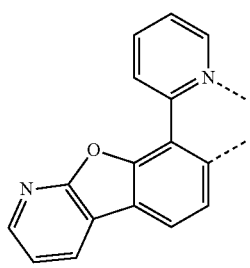
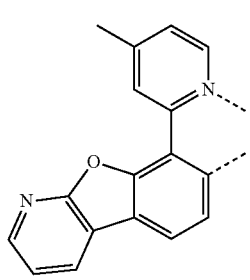
L$_{B77}$
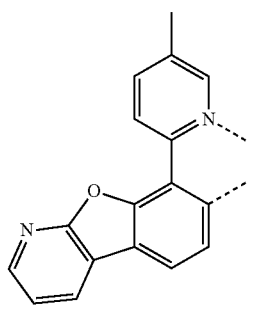
L$_{B78}$
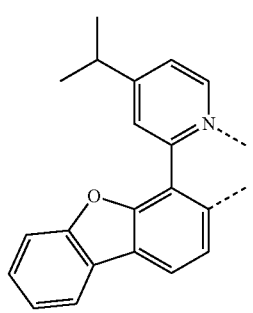
L$_{B79}$
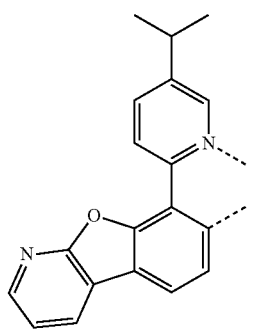
L$_{B80}$
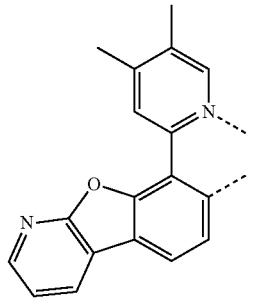
L$_{B81}$
L$_{B82}$
L$_{B83}$
L$_{B84}$
L$_{B85}$

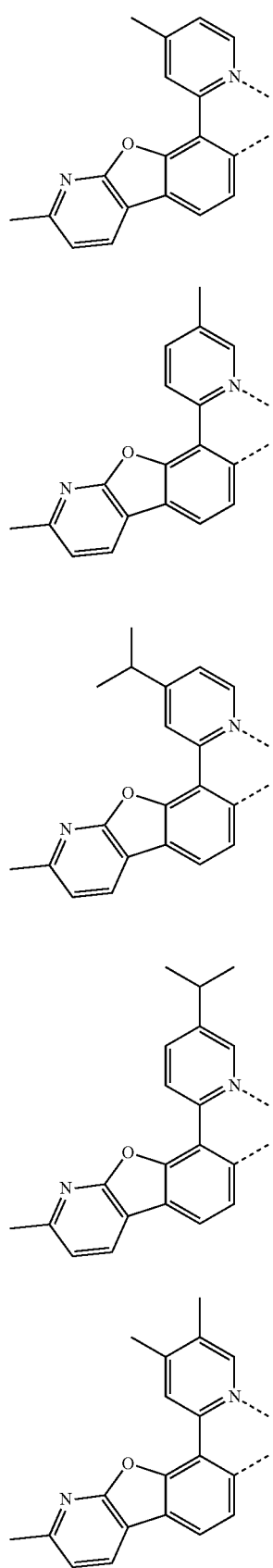
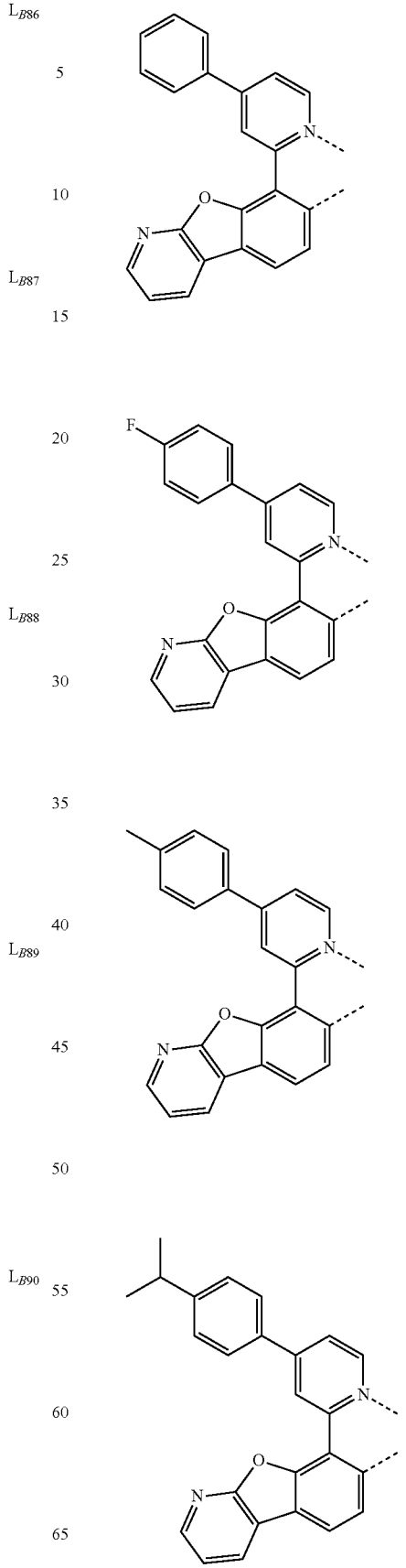

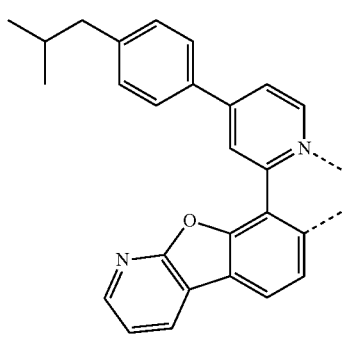 L_B95
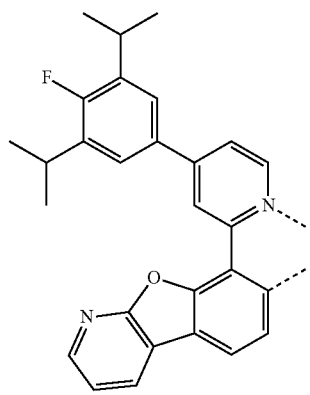 L_B99
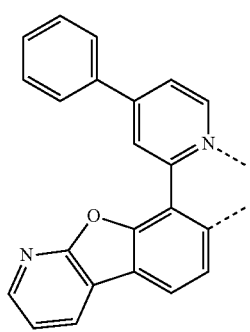 L_B96
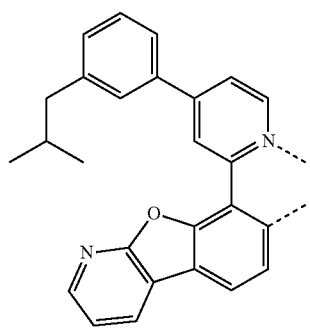 L_B100
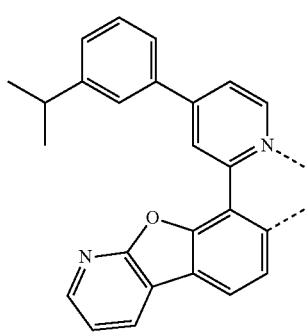 L_B97
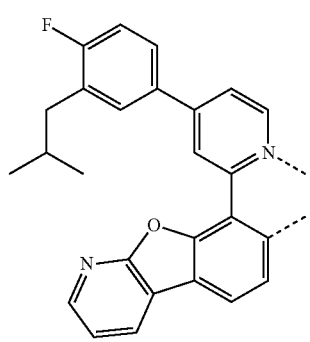 L_B101
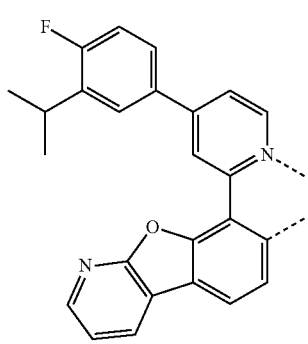 L_B98
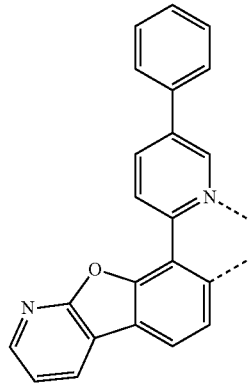 L_B102

-continued
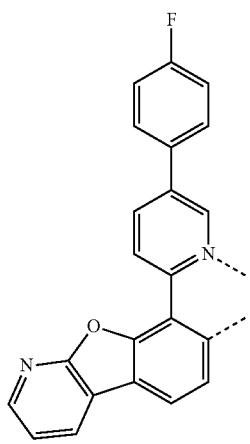
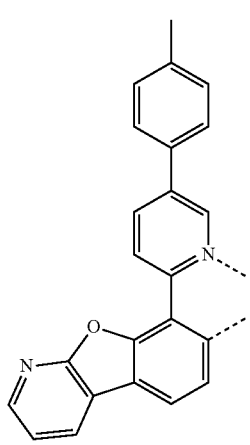
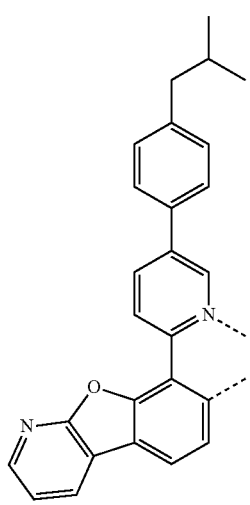 L_{B103}
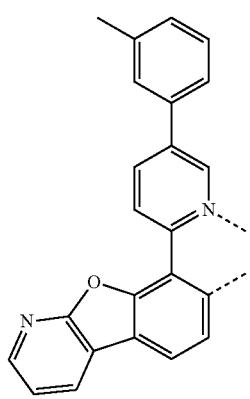 L_{B104}
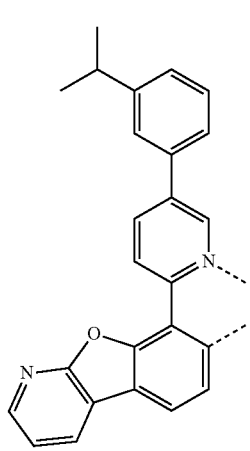 L_{B105}
L_{B106}
L_{B107}
L_{B108}

-continued
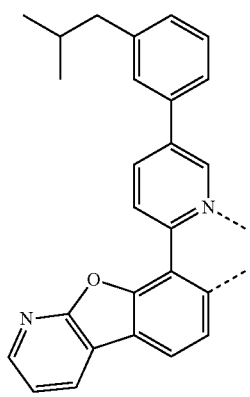
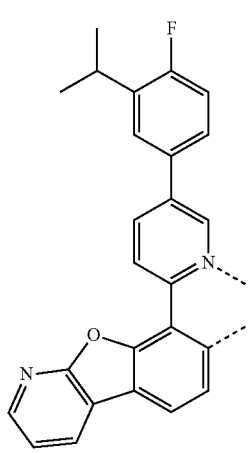
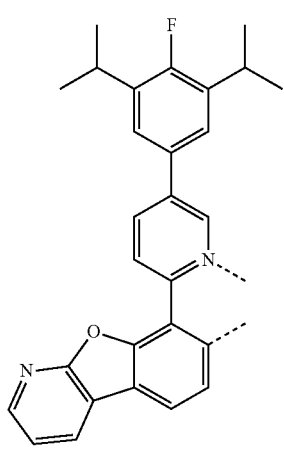
-continued
$L_{B109}$
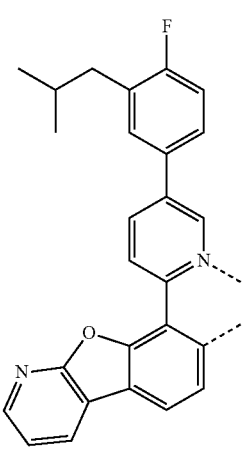
$L_{B110}$
$L_{B111}$
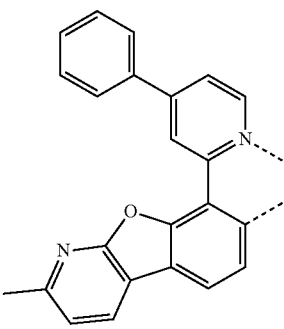
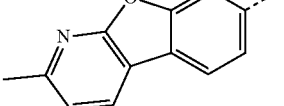
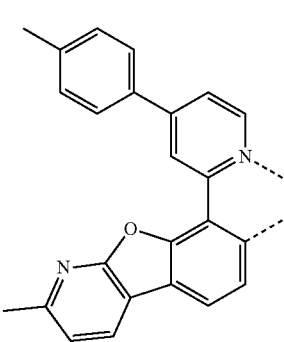
$L_{B112}$
$L_{B113}$
$L_{B114}$
$L_{B115}$ L<sub>B116</sub> 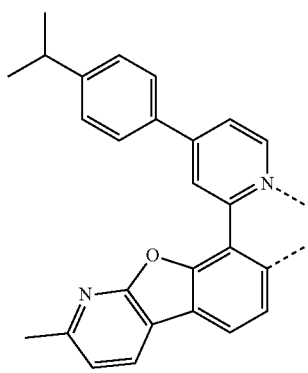
L<sub>B117</sub> 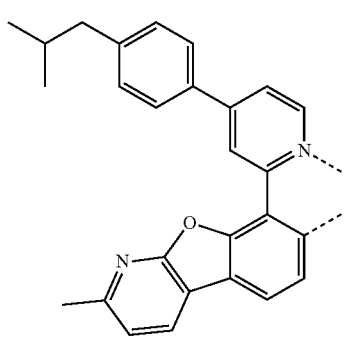
L<sub>B118</sub> 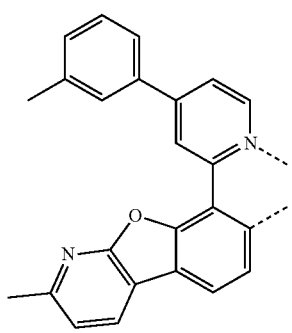
L<sub>B119</sub> 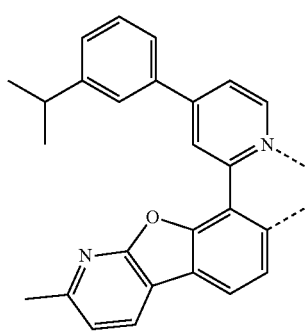
L<sub>B120</sub> 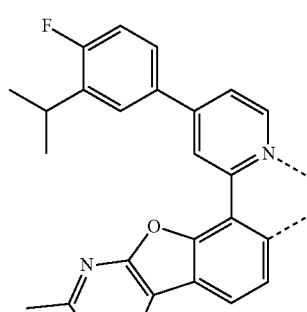
L<sub>B121</sub> 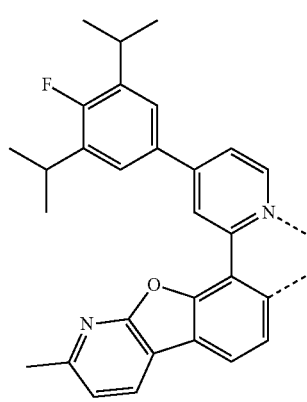
L<sub>B122</sub> 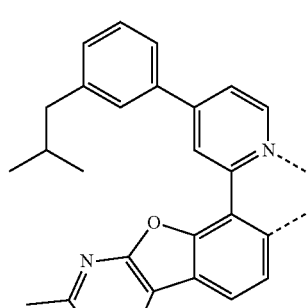
L<sub>B123</sub> 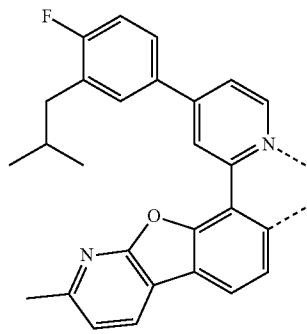

L_{B124}
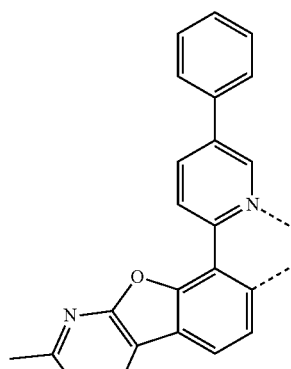
L_{B125}
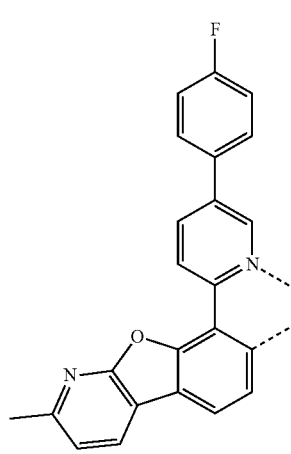
L_{B126}
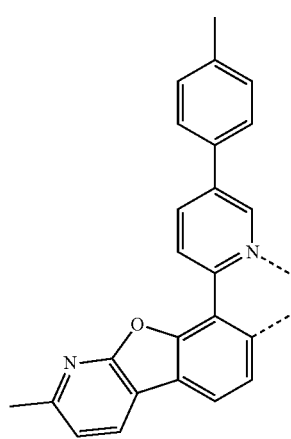
L_{B127}
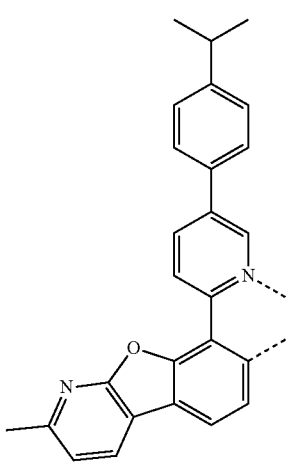
L_{B128}
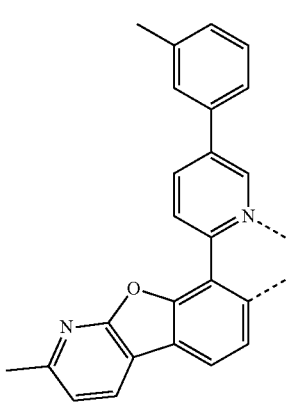
L_{B129}

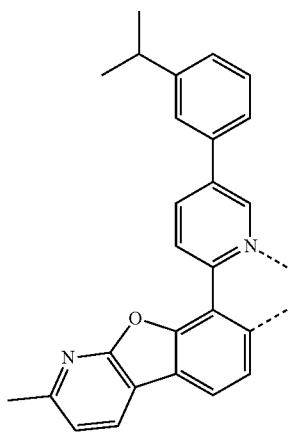
L_{B130}
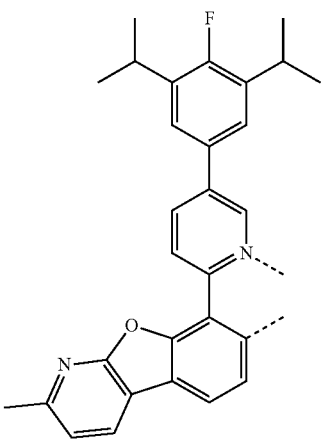
L_{B133}
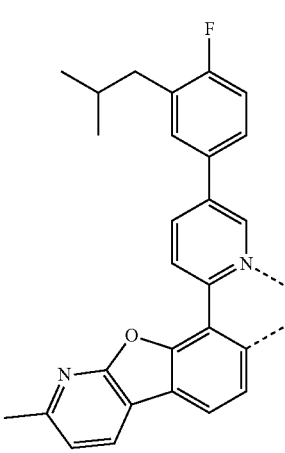
L_{B134}
L_{B131}
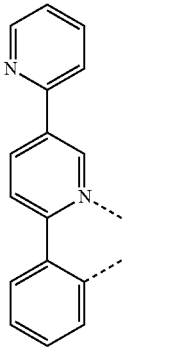
L_{B135}
L_{B132}
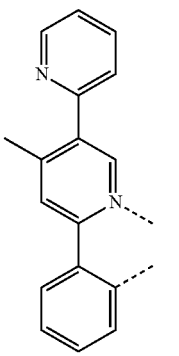
L_{B136}

L<sub>B137</sub> 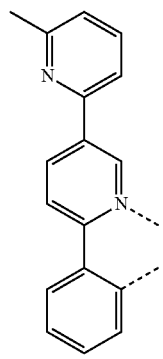
L<sub>B138</sub> 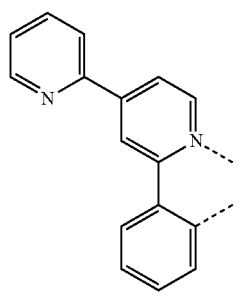
L<sub>B139</sub> 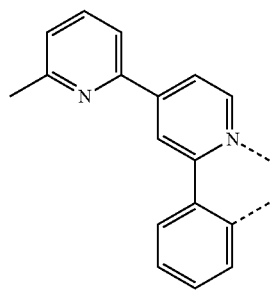
L<sub>B140</sub> 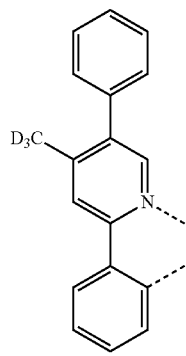
L<sub>B141</sub> 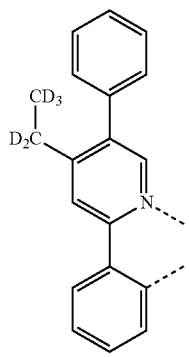
L<sub>B142</sub> 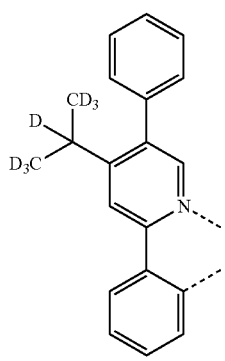
L<sub>B143</sub> 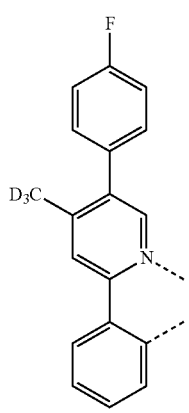
L<sub>B144</sub> 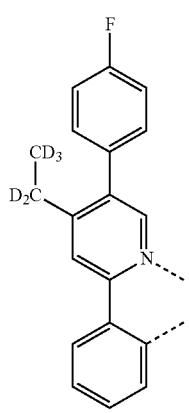

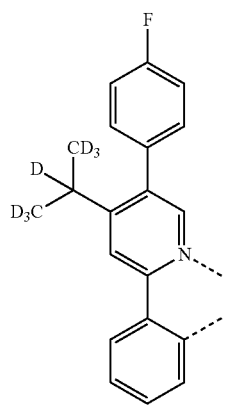
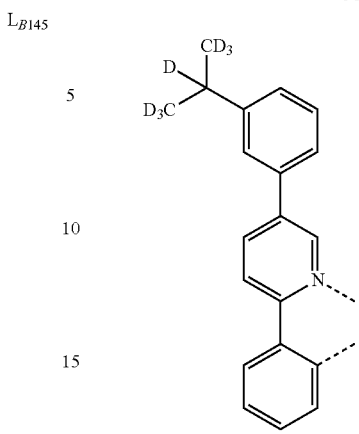
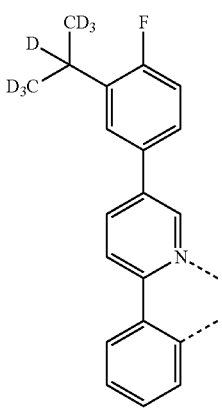
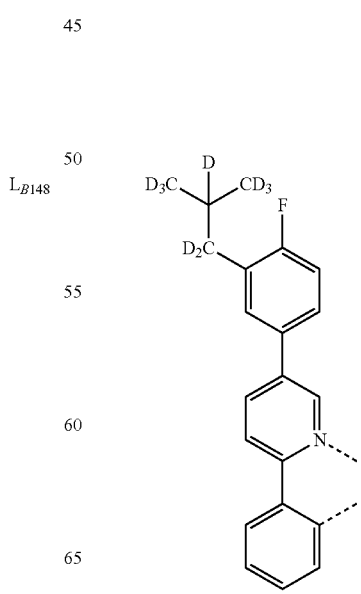

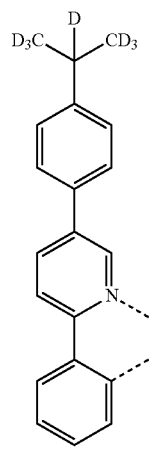
L_{B152}
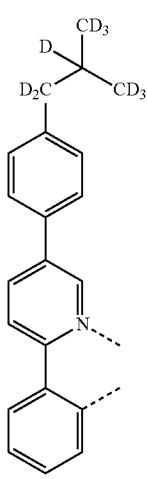
L_{B153}
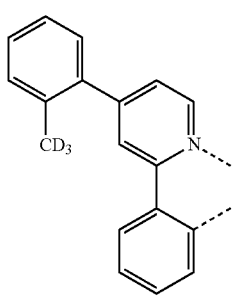
L_{B154}
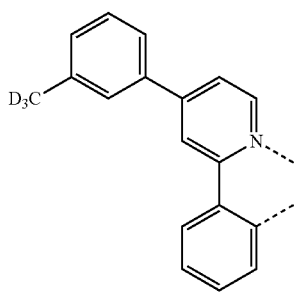
L_{B155}
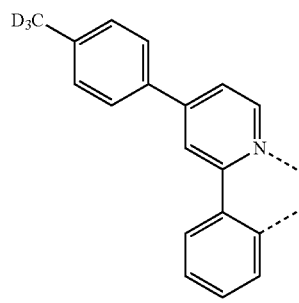
L_{B156}
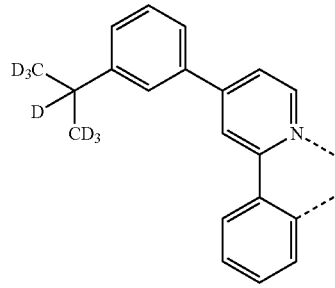
L_{B157}
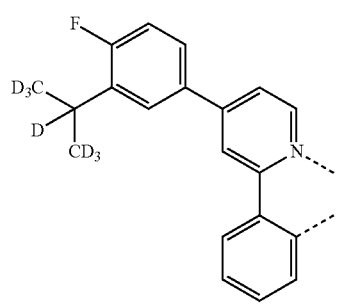
L_{B158}
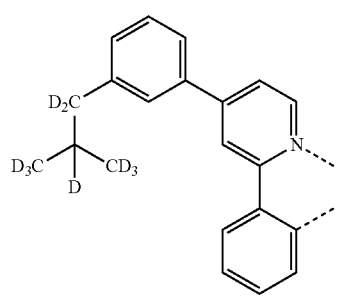
L_{B159}
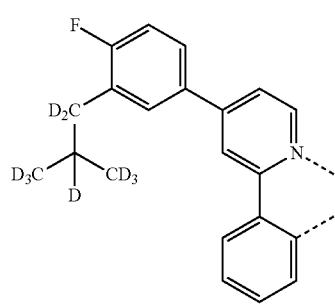
L_{B160}

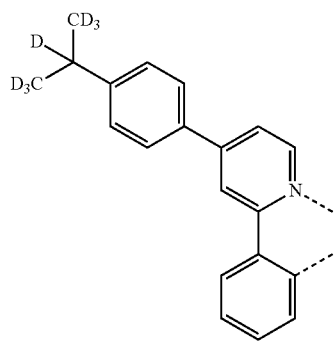
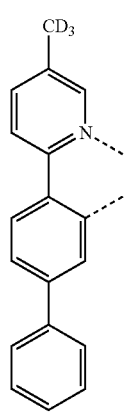
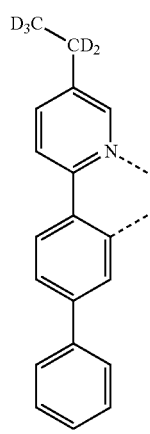
L<sub>B161</sub>
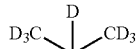
L<sub>B162</sub>
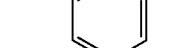
L<sub>B163</sub>
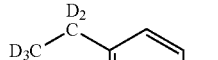
L<sub>B164</sub>

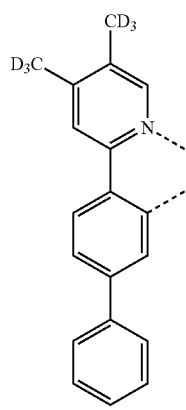
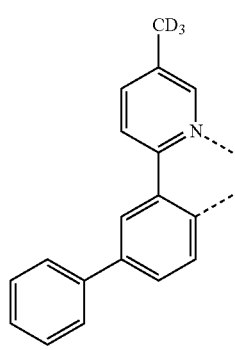
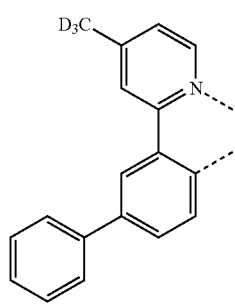
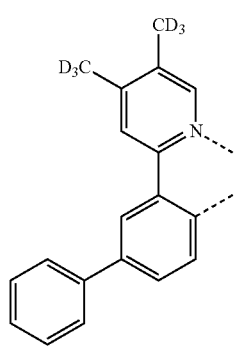
L$_{B169}$ 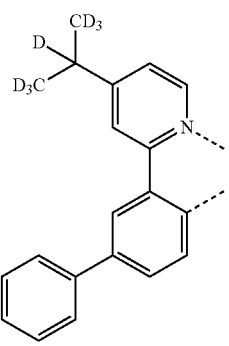 L$_{B173}$
L$_{B170}$ 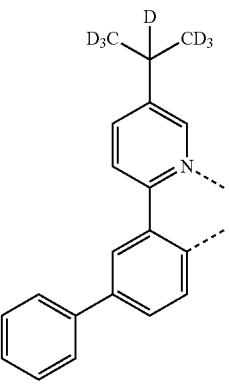 L$_{B174}$
L$_{B171}$ 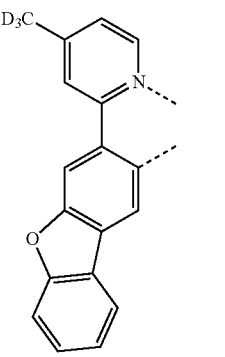 L$_{B175}$
L$_{B172}$ 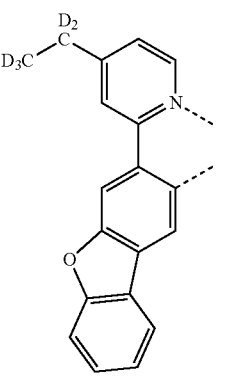 L$_{B176}$

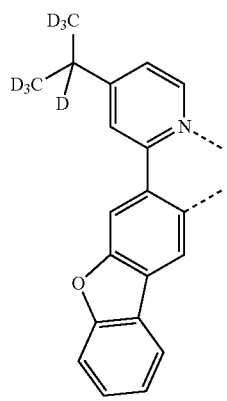
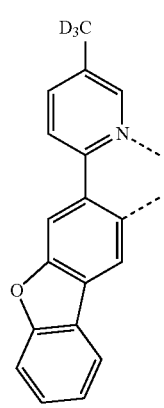
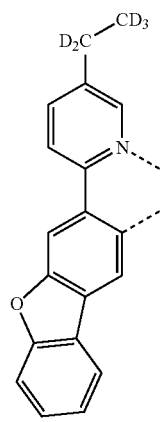
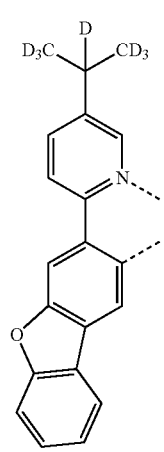
L<sub>B177</sub>
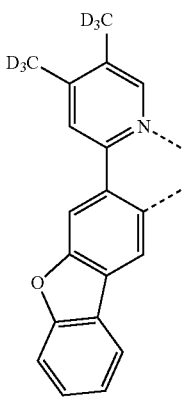
L<sub>B178</sub>
L<sub>B179</sub>
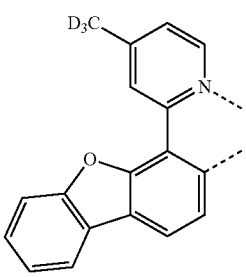
L<sub>B180</sub>
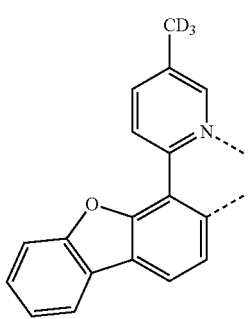
L<sub>B181</sub>
L<sub>B182</sub>
L<sub>B183</sub>
L<sub>B184</sub>
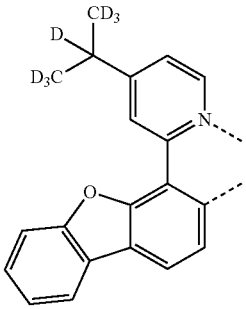

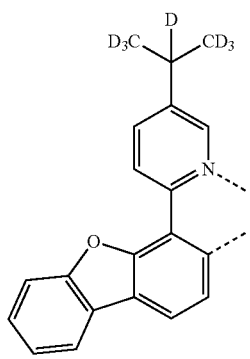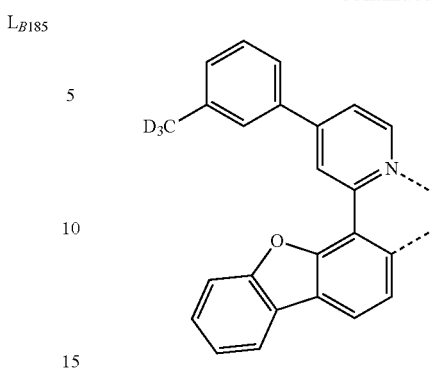

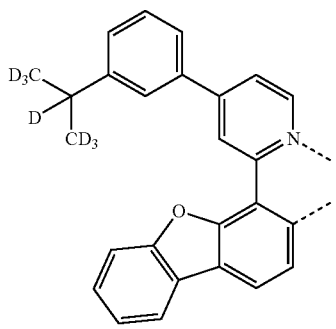 L_{B193}
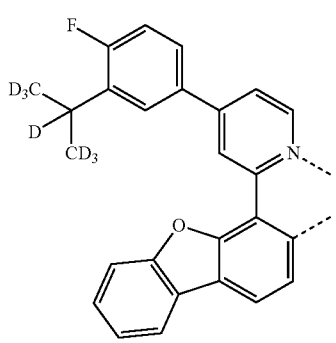 L_{B194}
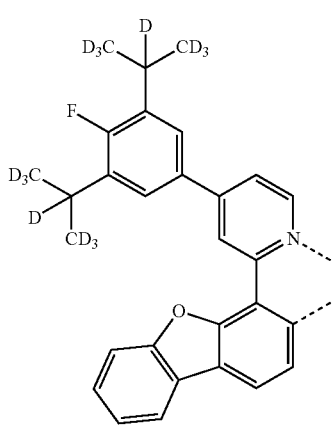 L_{B195}
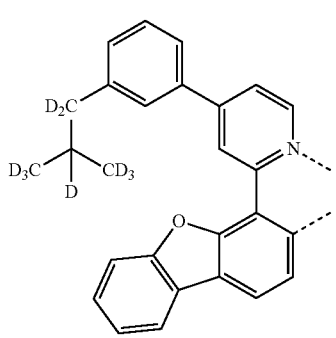 L_{B196}
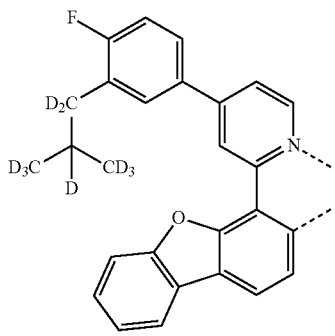 L_{B197}
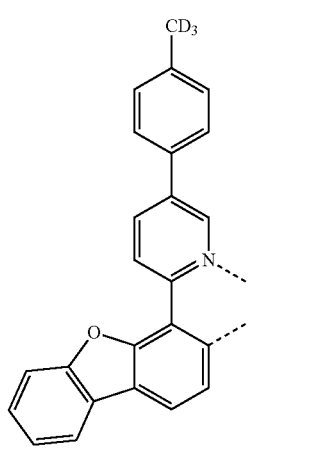 L_{B198}
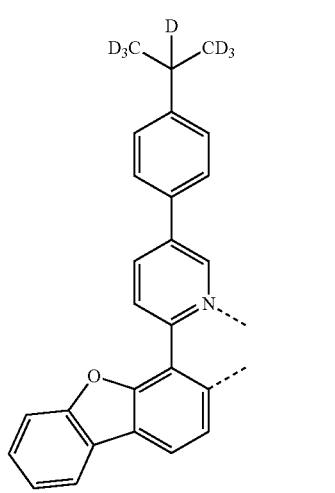 L_{B199}

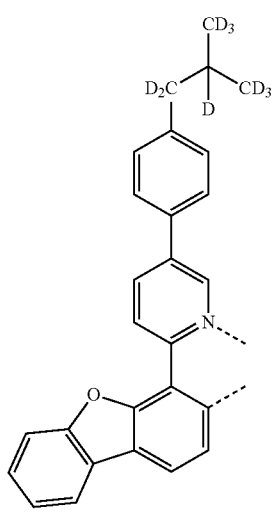
L_{B200}
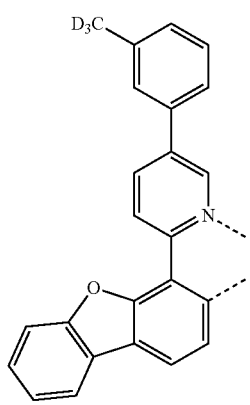
L_{B201}
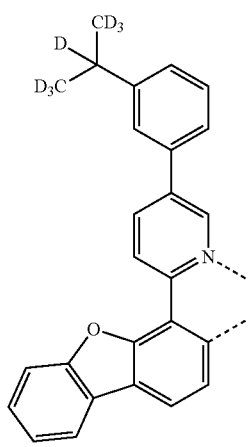
L_{B202}
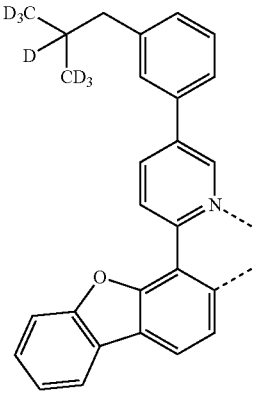
L_{B203}
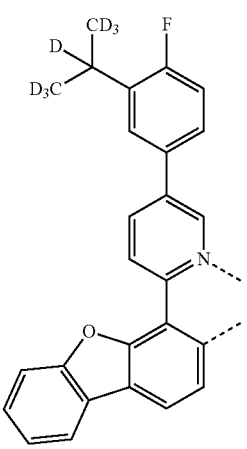
L_{B204}
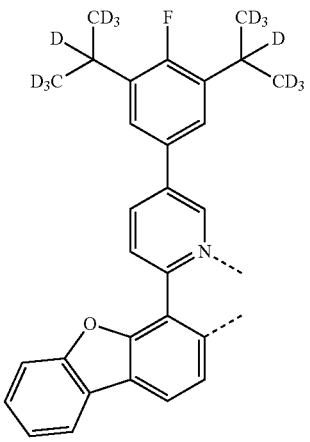
L_{B205}

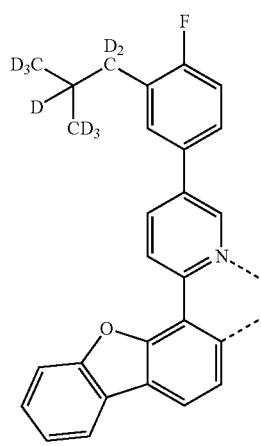
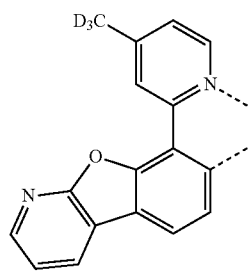
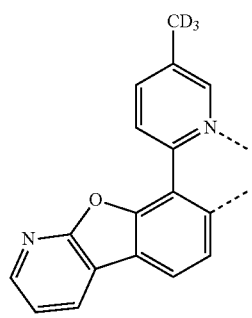
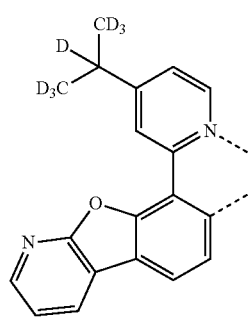
L_{B206}
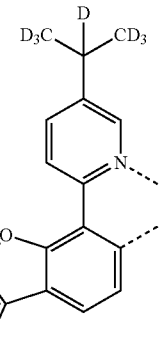
L_{B207}
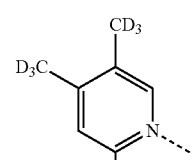
L_{B208}
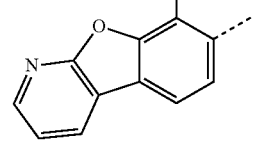
L_{B209}
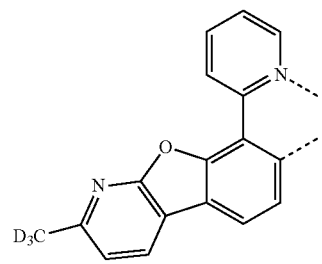
L_{B210}
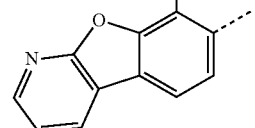
L_{B211}
L_{B212}
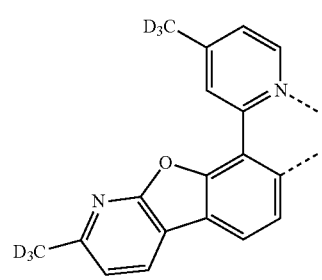
L_{B213}
L_{B214}
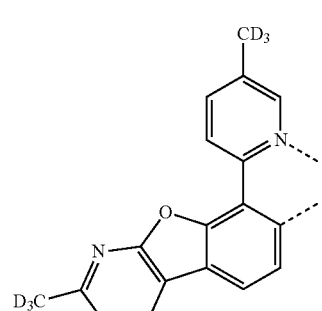

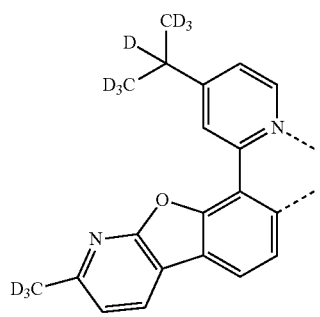
L_{B215}
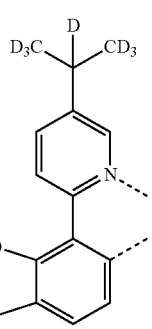
L_{B216}
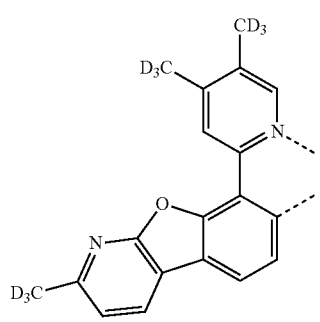
L_{B217}
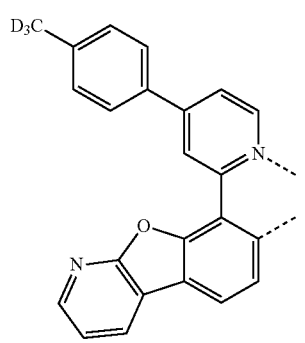
L_{B218}
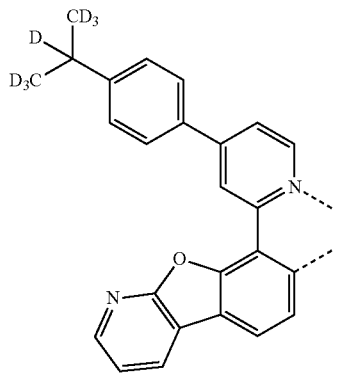
L_{B219}
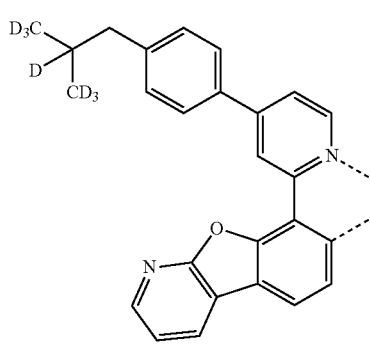
L_{B220}
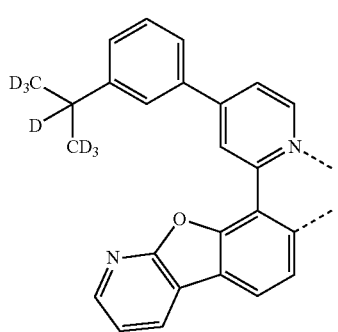
L_{B221}
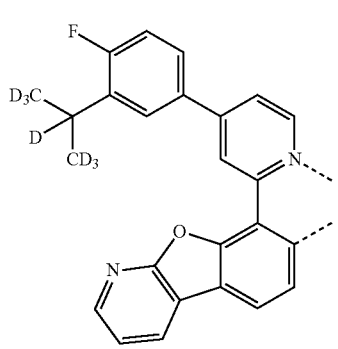
L_{B222}

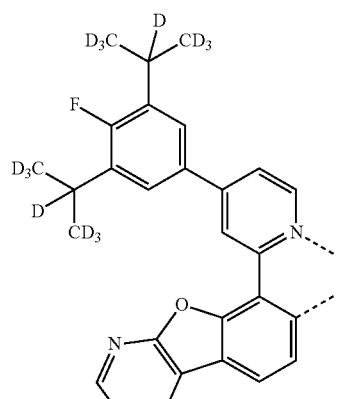
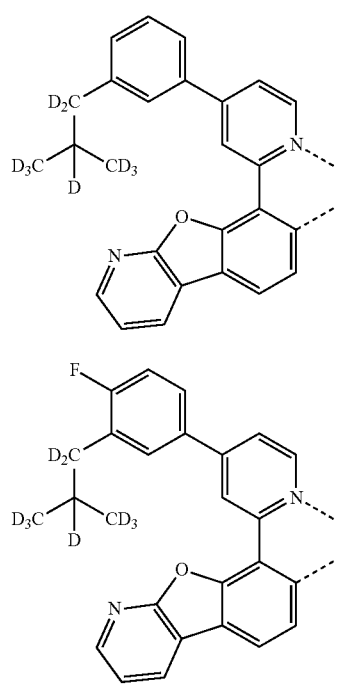
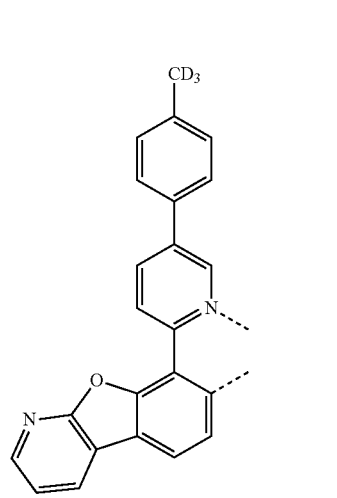
L<sub>B223</sub>
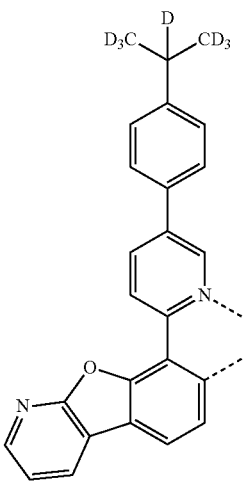
L<sub>B224</sub>
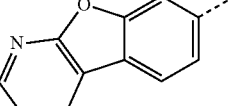
L<sub>B225</sub>
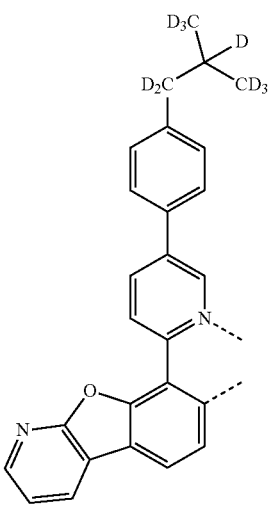
L<sub>B226</sub>
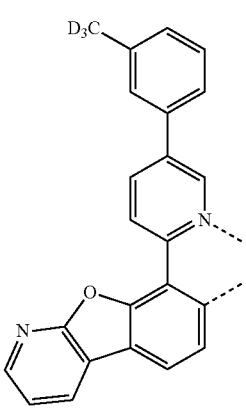
L<sub>B227</sub>
L<sub>B228</sub>
L<sub>B229</sub>

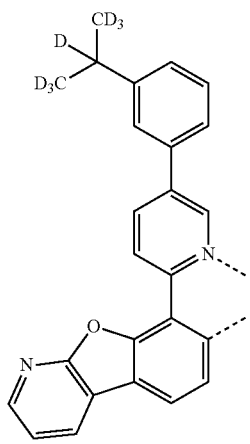
L_{B230}
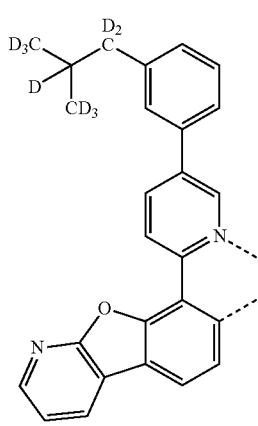
L_{B231}
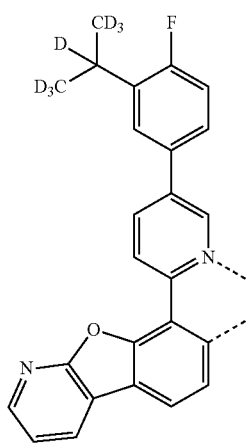
L_{B232}
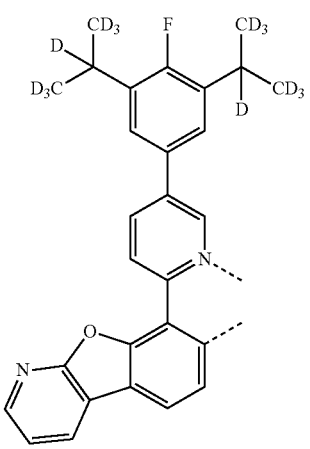
L_{B233}
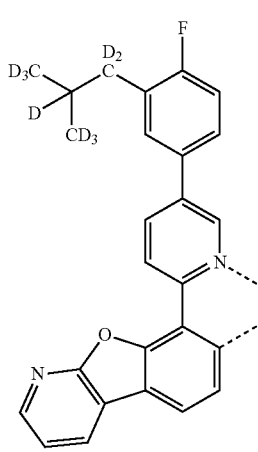
L_{B234}
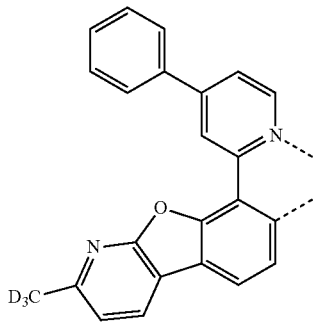
L_{B235}
L_{B236}

-continued
L<sub>B237</sub>
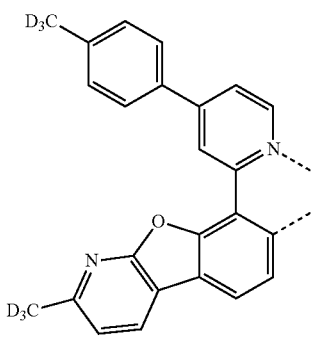
L<sub>B238</sub>
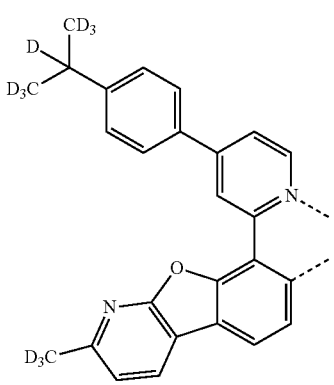
L<sub>B239</sub>
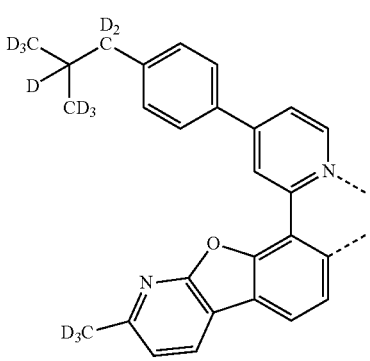
L<sub>B240</sub>
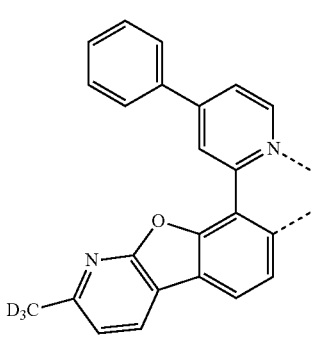
-continued
L<sub>B241</sub>
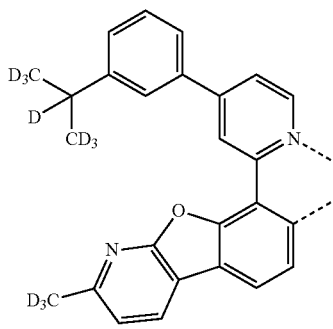
L<sub>B242</sub>
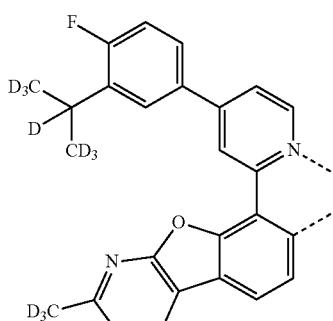
L<sub>B243</sub>
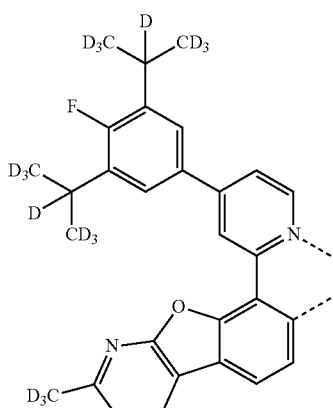
L<sub>B244</sub>
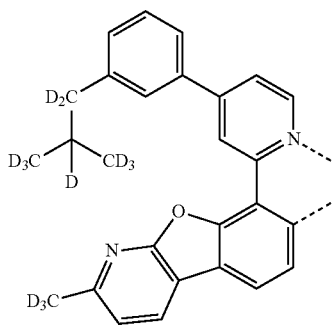

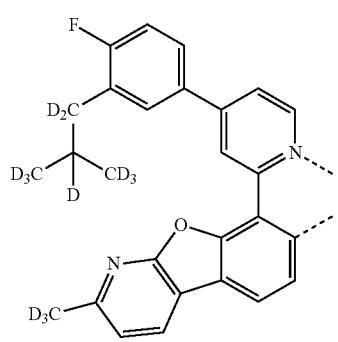
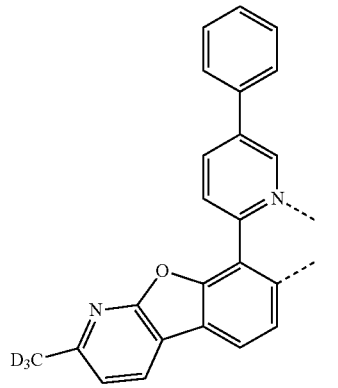
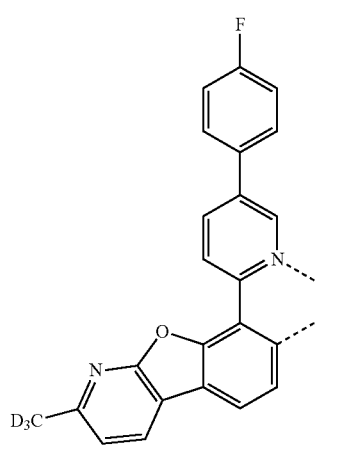
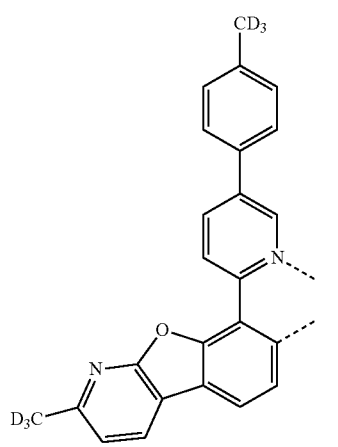
L$_{B245}$
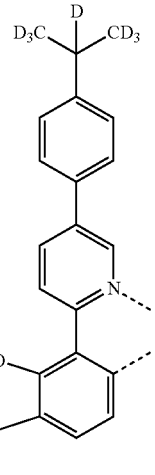
L$_{B246}$
L$_{B247}$
L$_{B248}$
L$_{B249}$
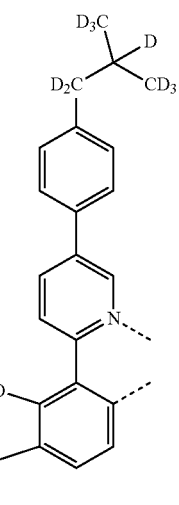
L$_{B250}$
L$_{B251}$
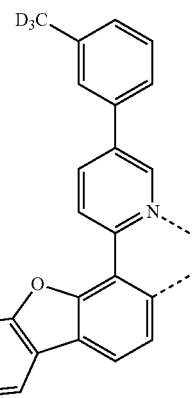

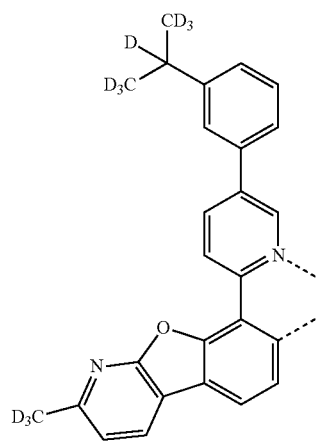
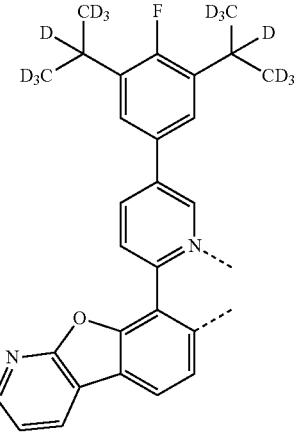

-continued $L_{B259}$

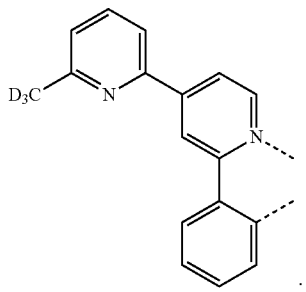

In some embodiments, $L_B$ is selected from the group consisting of $L_{B57}$, $L_{B58}$, $L_{B61}$, $L_{B67}$, and $L_{A69}$. In some embodiments, $L_B$ is $L_{B57}$. In some embodiments, $L_B$ is $L_{B58}$. In some embodiments, $L_B$ is $L_{B61}$. In some embodiments, $L_B$ is $L_{B67}$. In some embodiments, $L_B$ is $L_{B69}$.

In some embodiments, $L_A$ is formula II and $L_B$ is formula III. In embodiments where $L_A$ is formula II and $L_B$ is formula III, the compound has the formula I-A:

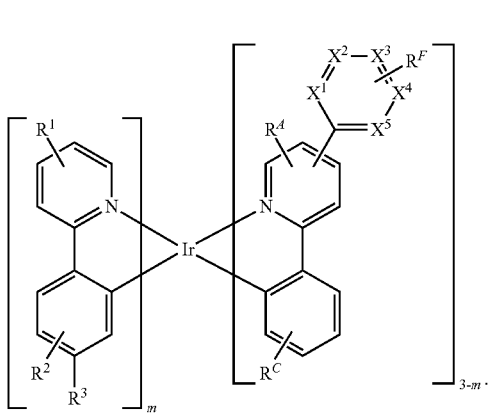

(I-A)

In the compound of formula I-A, $R^2$ and $R_A$ are each independently mono, di, or tri-substitution, or no substitution; $R^1$, $R_C$, and $R_F$ are each independently mono, di, tri, or tetra-substitution, or no substitution; $X^1$, $X^2$, $X^3$, $X^4$, and $X^5$ are each independently carbon or nitrogen; $R^1$, $R^2$, $R_A$, $R_C$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, $L_A$ is formula II and $L_B$ is formula IV. In embodiments where $L_A$ is formula II and $L_B$ is formula IV, the compound has the formula I-B;

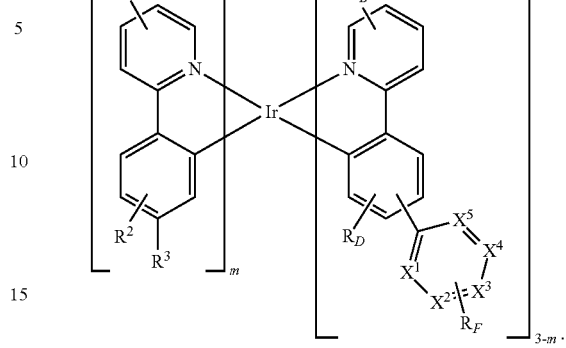

(I-B)

In the compound of formula I-B, $R^2$ and $R_D$ are each independently mono, di, or tri-substitution, or no substitution; $R^1$, $R_B$, and $R_F$ are each independently mono, di, tri, or tetra-substitution, or no substitution; $X^1$, $X^2$, $X^3$, $X^4$, and $X^5$ are each independently carbon or nitrogen; $R^1$, $R^2$, $R_B$, $R_D$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, $L_A$ is formula II and $L_B$ is formula V. In embodiments where $L_A$ is formula II and $L_B$ is formula V, the compound has the formula I-C:

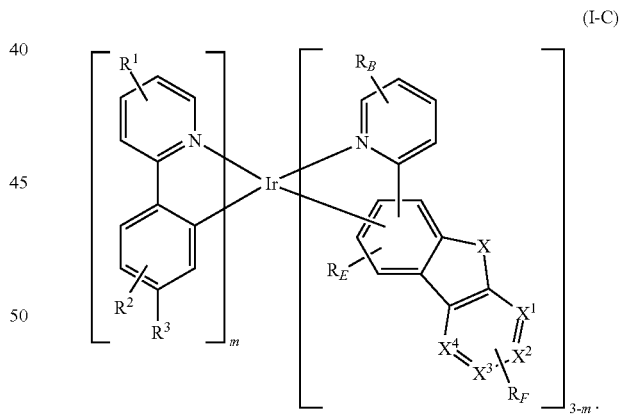

(I-C)

In the compound of formula I-C, $R_E$ represents mono or di-substitution, or no substitution; $R^2$ represents mono, di, or tri-substitution, or no substitution; $R^1$, $R_B$, and $R_F$ are each independently mono, di, tri, or tetra-substitution, or no substitution; $X^1$, $X^2$, $X^3$, and $X^4$ are each independently carbon or nitrogen; $R^1$, $R^2$, $R_B$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, m is 1. In some embodiments, m is 2.

In some embodiments, X is O. In some embodiments, X is S. In some embodiments, X is Se.

In some embodiments, no more than 2 of $X^1$, $X^2$, $X^3$, $X^4$, and $X^5$ are nitrogen.

In some embodiments, no more than 1 of $X^1$, $X^2$, $X^3$, $X^4$, and $X^5$ is nitrogen. In some embodiments, $X^1$, $X^2$, $X^3$, $X^4$, and $X^5$ are carbon.

In some embodiments, $R^3$ is an alkyl having at least 2 carbons. In some embodiments, $R^3$ is an alkyl having at least 3 carbons. In some embodiments, $R^3$ is a cycloalkyl. In some embodiments, $R^3$ is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, and cyclohexyl, wherein each is optionally partially or fully deuterated.

In some embodiments, $R^1$ is selected from the group consisting of hydrogen, deuterium, alkyl, cycloalkyl, and combinations thereof.

In some embodiments, $R^2$ represents no substitution.

In some embodiments, $R_F$ is selected from the group consisting of hydrogen, deuterium, alkyl, cycloalkyl, halogen, and combinations thereof in some embodiments, $R_F$ is fluorine.

In some embodiments, $R_C$, $R_D$, and $R_E$ each represent no substitution.

In some embodiments, the compound of formula I is selected from the group consisting of Compound I-1 to Compound I-15 listed below:

Compound I-1

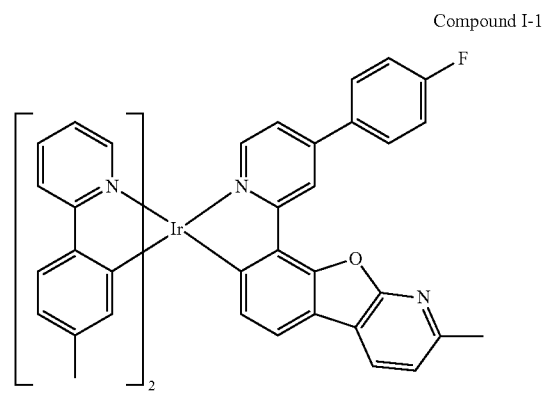

Compound I-2

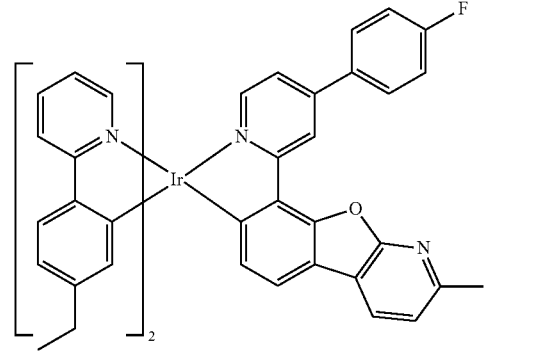

Compound I-3

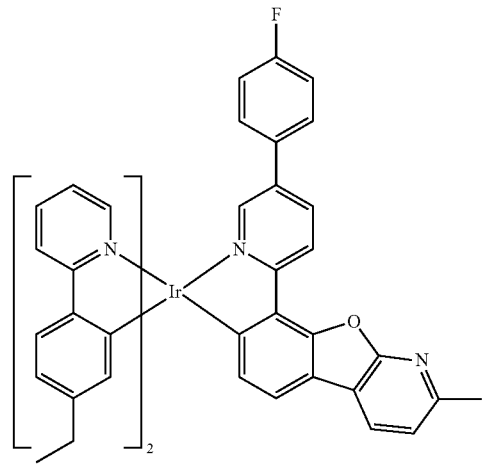

Compound I-4

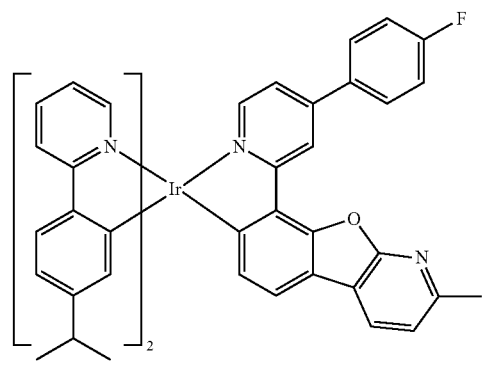

Compound I-5

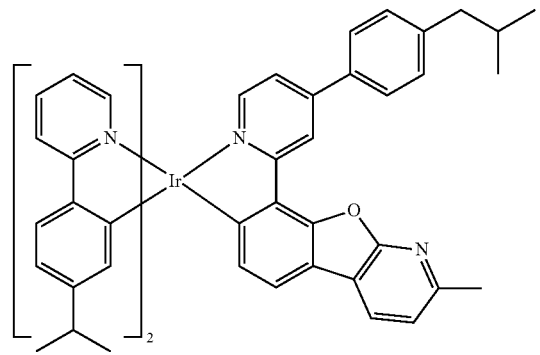

Compound I-6

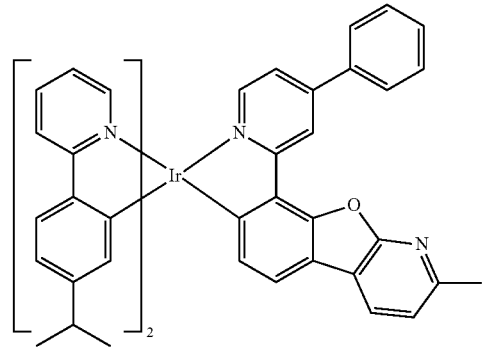

Compound I-7
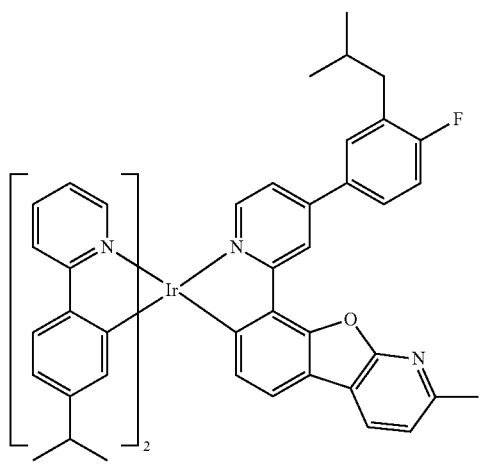
Compound I-8
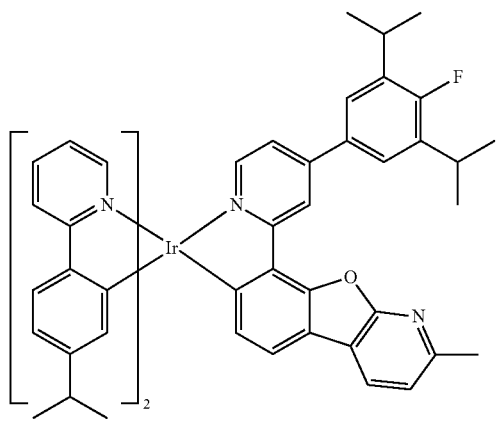
Compound I-9
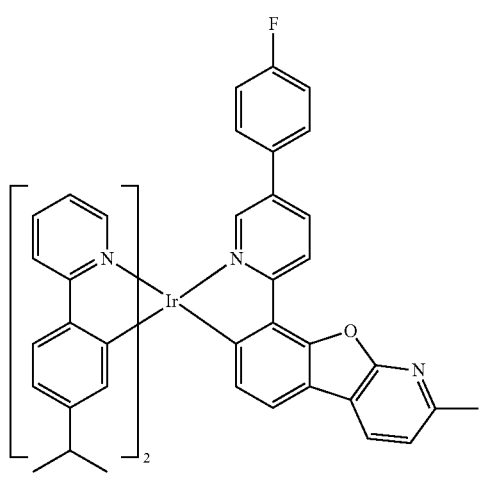
Compound I-10
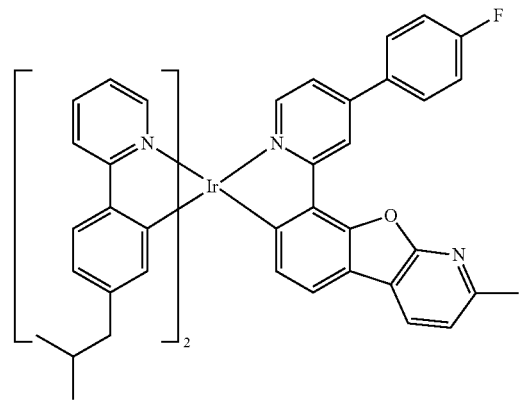
Compound I-11
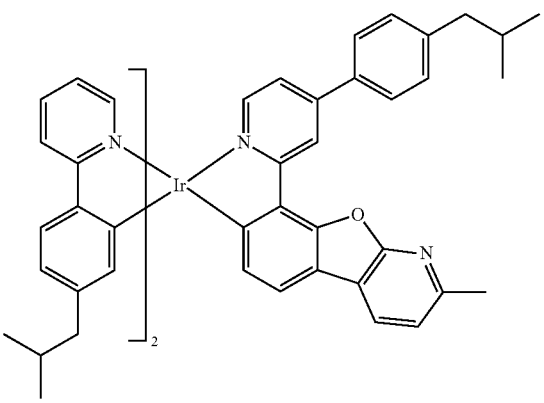
Compound I-12
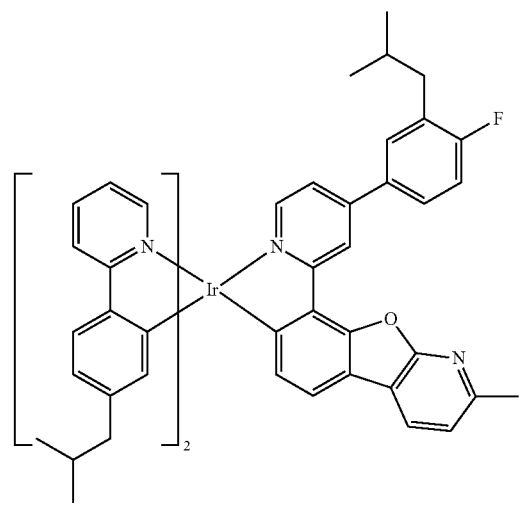

-continued
Compound I-13
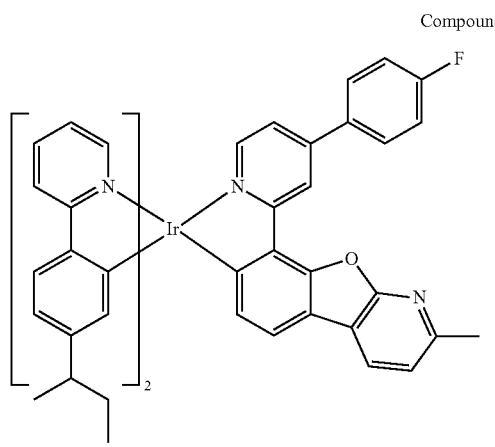
Compound I-14
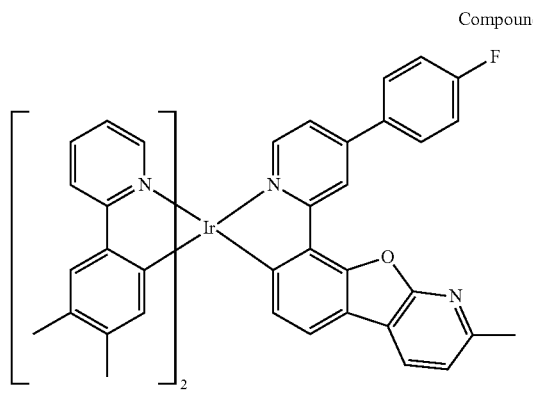
and
Compound I-15
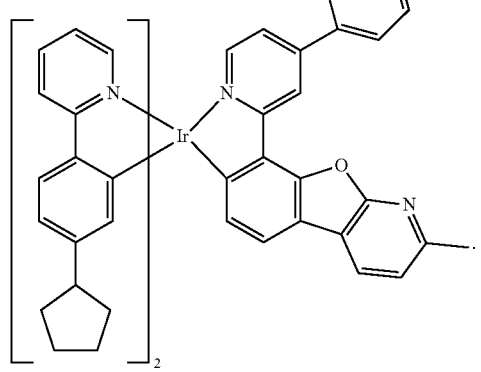
Compound I-15
In some embodiments, the compound of formula I is selected from the group consisting of Compound I-16 to Compound I-19 listed below:
Compound I-16
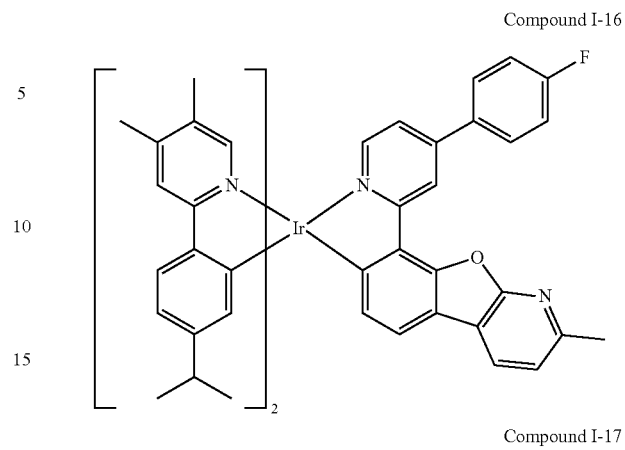
Compound I-17
Compound I-18
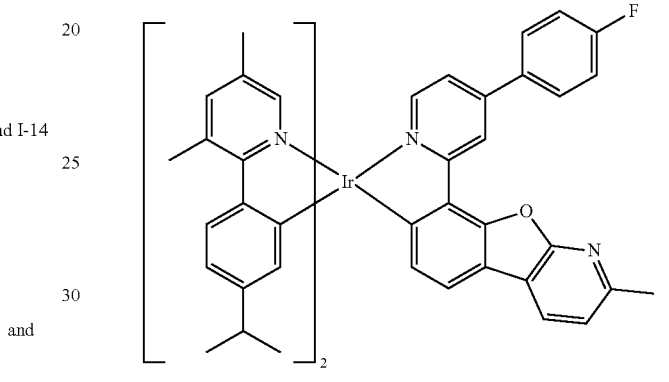
Compound I-19
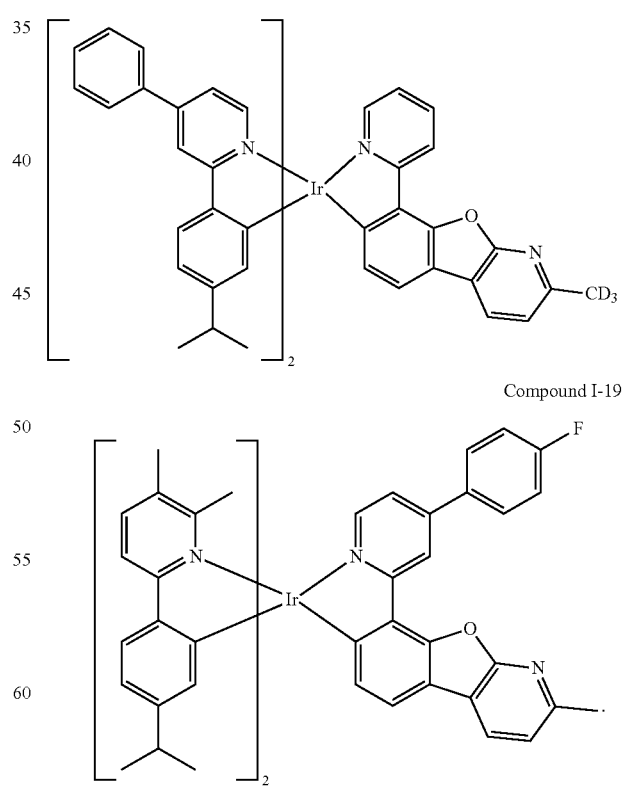
In some embodiments, a first device is provided. The first device comprises an anode, a cathode, and an organic layer, disposed between the anode and the cathode, comprising a compound having the formula:

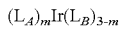  (I).

In the compound of formula I, $L_A$ is

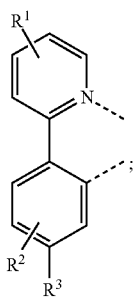  (II)

$L_B$ is selected from the group consisting of:

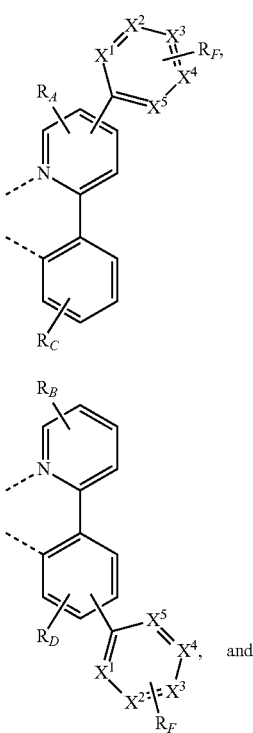

(III)

(IV)

and (V)

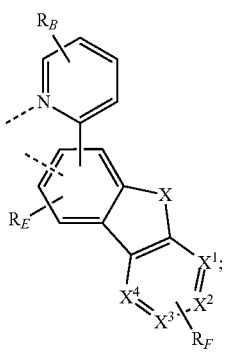

$R_E$ represents mono or di-substitution, or no substitution; $R^2$, $R_A$, and $R_D$ are each independently mono, di, or tri-substitution, or no substitution; $R^1$, $R_B$, $R_C$, and $R_F$ are each independently mono, di, tri, or tetra-substitution, or no substitution; $X^1$, $X^2$, $X^3$, $X^4$, and $X^5$ are each independently carbon or nitrogen; X is selected from the group consisting of O, S, and Se; $R^1$, $R^2$, $R_A$, $R_B$, $R_C$, $R_D$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, the first device comprises an anode, a cathode, and an organic layer, disposed between the anode and the cathode, comprising a compound having the formula I-A. In embodiments where $L_A$ is formula II and $L_B$ is formula III, the compound has the formula I-A:

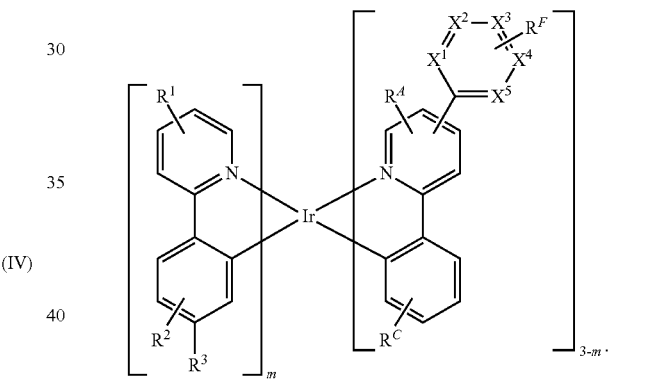

(I-A)

In the compound of formula I-A, $R^2$ and $R_A$ are each independently mono, di, or tri-substitution, or no substitution; $R^1$, $R_C$, and $R_F$ are each independently mono, di, or tetra-substitution, or no substitution; $X^1$, $X^2$, $X^3$, $X^4$, and $X^5$ are each independently carbon or nitrogen; $R^1$, $R^2$, $R_A$, $R_C$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, the first device comprises an anode, a cathode, and an organic layer, disposed between the anode and the cathode, comprising a compound having the formula I-B. In embodiments where $L_A$ is formula II and $L_B$ is formula IV, the compound has the formula I-B:

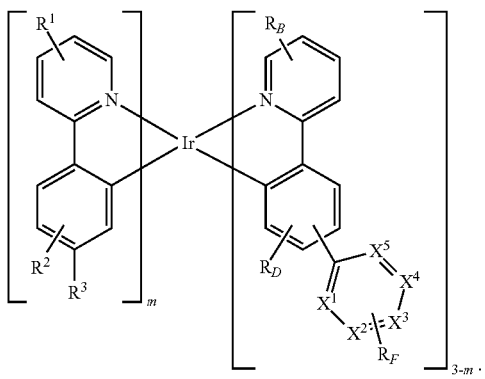

(I-B)

In the compound of formula I-B, $R^2$ and $R_D$ are each independently mono, di, or tri-substitution, or no substitution; $R^1$, $R_B$, and $R_F$ are each independently mono, di, tri, or tetra-substitution, or no substitution; $X^1$, $X^2$, $X^3$, $X^4$, and $X^5$ are each independently carbon or nitrogen; $R^1$, $R^2$, $R_B$, $R_D$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, the first device comprises an anode, a cathode, and an organic layer, disposed between the anode and the cathode, comprising a compound having the formula I-C. In embodiments where $L_A$ is formula II and $L_B$ is formula V, the compound has the formula I-C:

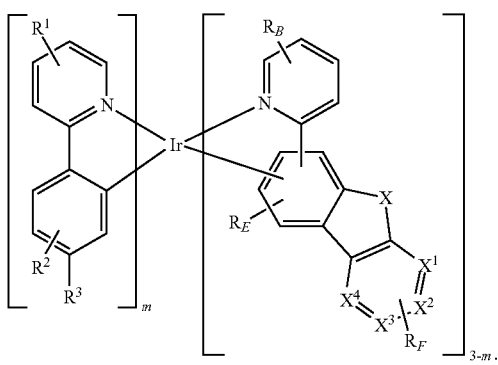

(I-C)

In the compound of formula I-C, $R_E$ represents mono or di-substitution, or no substitution; $R^2$ represents mono, di, or tri-substitution, or no substitution; $R^1$, $R_B$, and $R_F$ are each independently mono, di, tri, or tetra-substitution, or no substitution; $X^1$, $X^2$, $X^3$, $X^4$, and $X^5$ are each independently carbon or nitrogen; $R^1$, $R^2$, $R_B$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof; $R^3$ is selected from the group consisting of alkyl, cycloalkyl, and combinations thereof; $R^3$ is optionally partially or fully deuterated; and m is 1 or 2.

In some embodiments, the first device is a consumer product.

In some embodiments, the first device is an organic light-emitting device.

In some embodiments, the first device comprises a lighting panel.

In some embodiments, the organic layer of the first device is an emissive layer and the compound is an emissive dopant. In some embodiments, the organic layer of the first device is an emissive layer and the compound is a non-emissive dopant.

In some embodiments, the organic layer of the first device further comprises a host.

In some embodiments, the host of the first device comprises a triphenylene containing benzo-fused thiophene or benzo-fused furan; wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $Ar_1$, $Ar_1-Ar_2$, $C_nH_{2n}-Ar_1$, or no substitution; wherein n is from 1 to 10; and wherein $Ar_1$ and $Ar_2$ are independently selected from the group consisting of benzene, biphenyl, naphthalene, triphenylene, carbazole, and heteroaromatic analogs thereof.

In some embodiments, the host of the first device comprises at least one chemical group selected from the group consisting of carbazole, dibenzothiophene, dibenzofuran, dibenzoselenophene, azacarbazole, aza-dibenzothiophene, aza-dibenzofuran, and aza-dibenzoselenophene.

In some embodiments, the host is selected from the group consisting of:

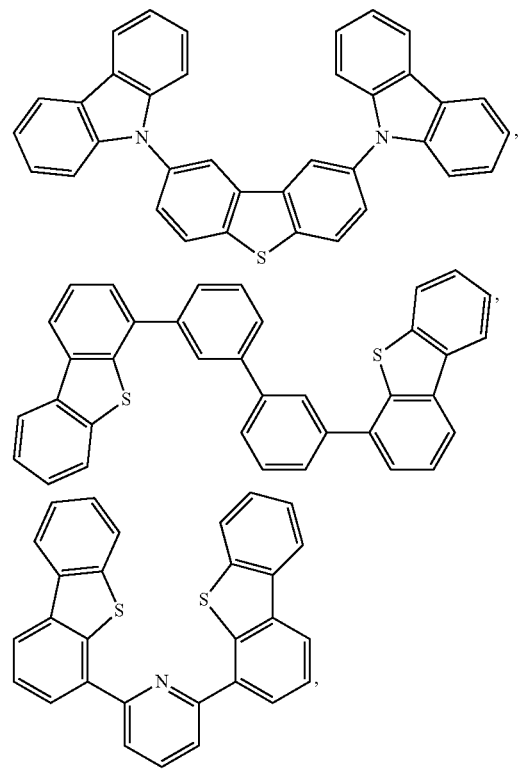

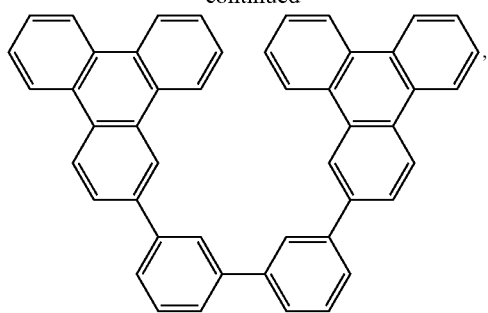

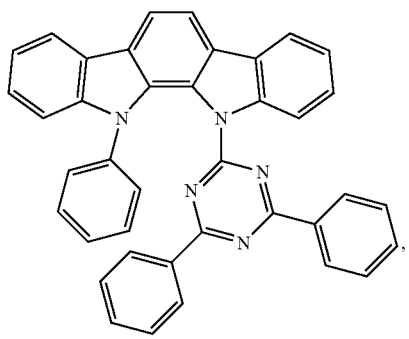

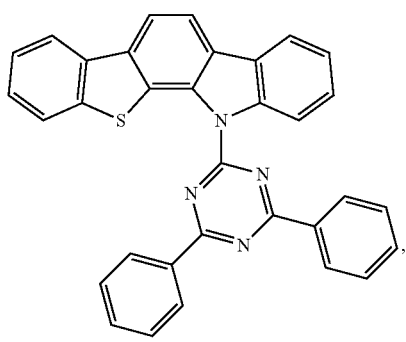

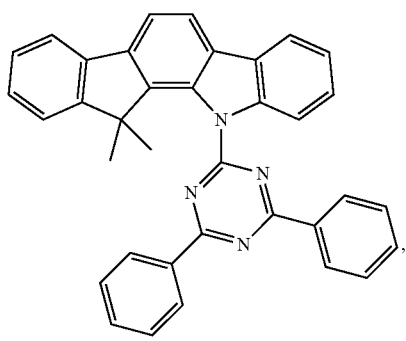

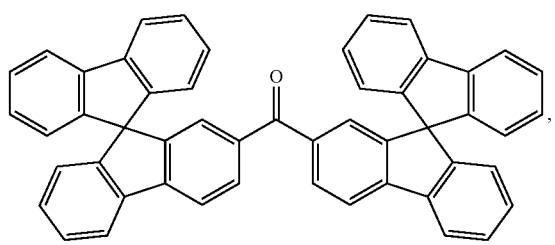

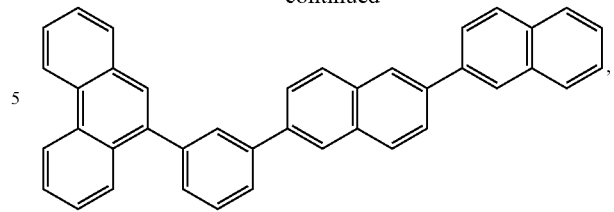

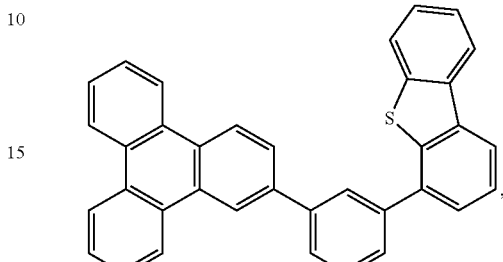

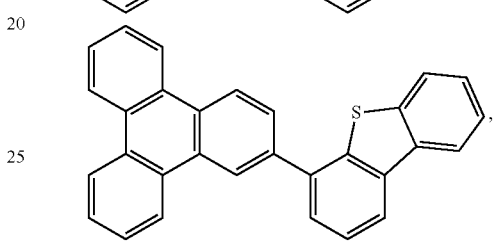

and combinations thereof.

In some embodiments, the host of the first device comprises a metal complex.

In some embodiments, a formulation comprising a compound of formula I is provided.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to the following general structures:

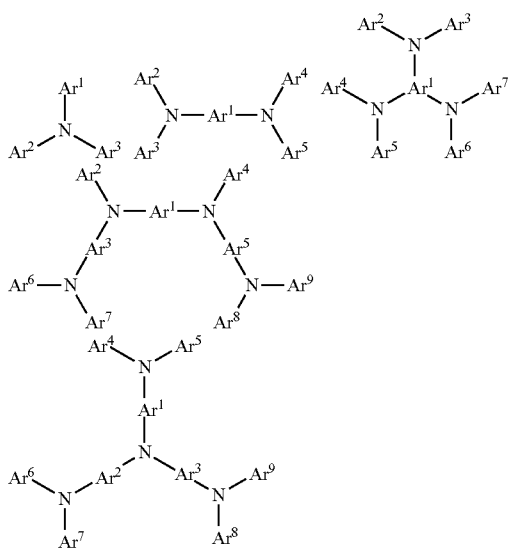

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, $Ar^1$ to $Ar^9$ is independently selected from the group consisting of:

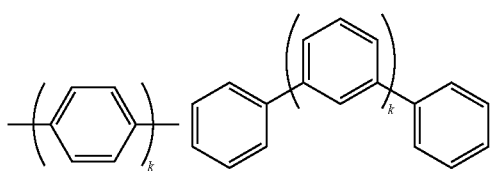

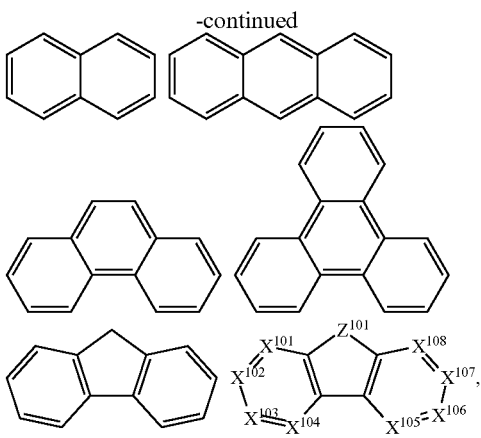

k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

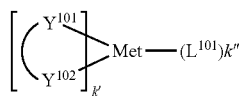

Met is a metal; ($Y^{101}$-$Y^{102}$) is a bidentate ligand, $Y^{101}$ and $Y^{102}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In some embodiments, ($Y^{101}$-$Y^{102}$) is a 2-phenylpyridine derivative.

In some embodiments, ($Y^{101}$-$Y^{102}$) is a carbene ligand.

In some embodiments, Met is selected from Ir, Pt, Os, and Zn.

In a further aspect, the metal complex has a smallest oxidation potential in solution vs. $Fc^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

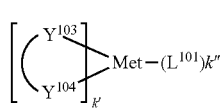

Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In some embodiments, the metal complexes are:

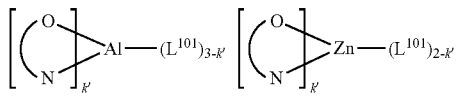

(O—N) is a bidentate ligand, having metal coordinated to atoms O and N.

In some embodiments, Met is selected from Ir and Pt.

In a further aspect, $(Y^{101}-Y^{104})$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof.

In some embodiments, the host compound contains at least one of the following groups in the molecule:

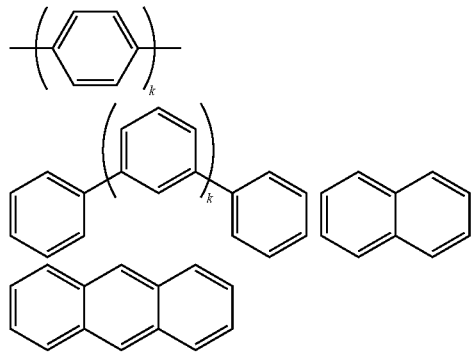

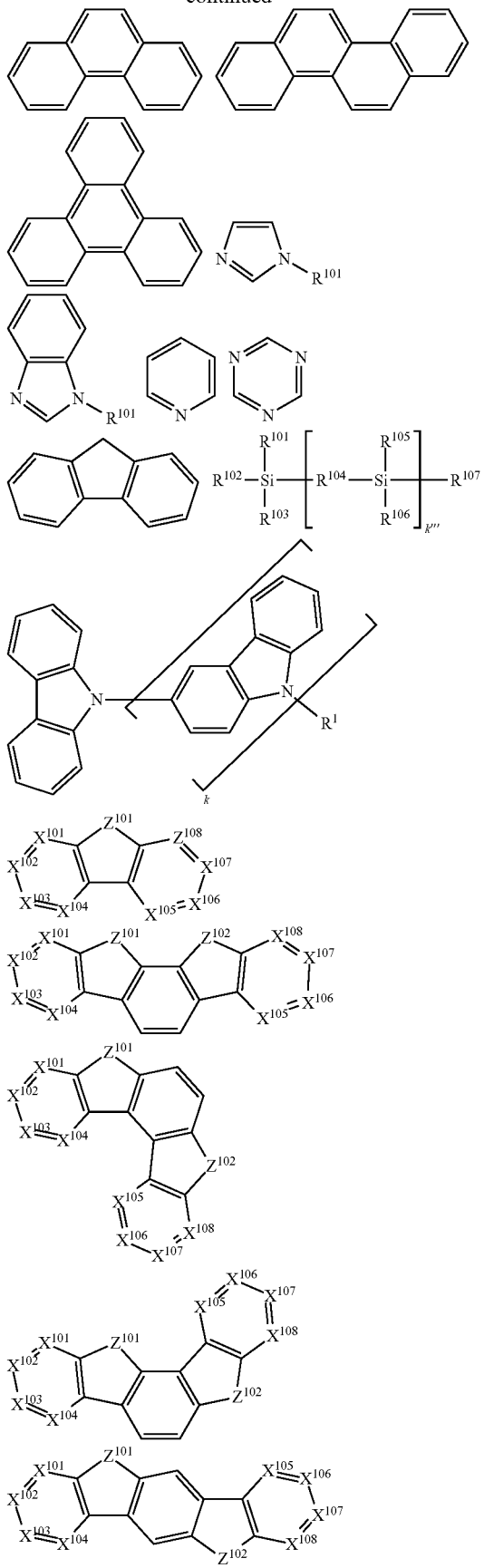

-continued

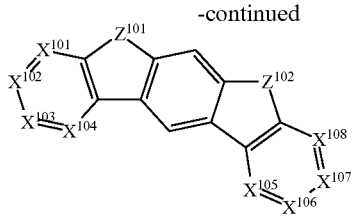

R¹⁰¹ to R¹⁰⁷ is independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, when it is aryl or heteroaryl, it has the similar definition as Ar's mentioned above.

k is an integer from 1 to 20; k''' is an integer from 0 to 20.
X¹⁰¹ to X¹⁰⁸ is selected from C (including CH) or N.
Z¹⁰¹ and Z¹⁰² is selected from NR¹⁰¹, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In some embodiments, compound used in HBL contains the same molecule or the same functional groups used as host described above.

In some embodiments, compound used in HBL contains at least one of the following groups in the molecule:

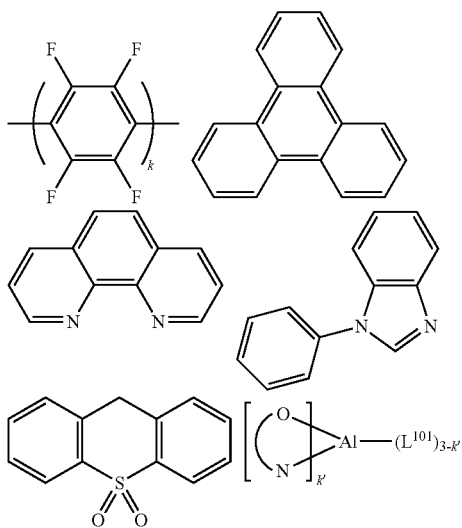

k is an integer from 1 to 20; L¹⁰¹ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In some embodiments, compound used in ETL contains at least one of the following groups in the molecule:

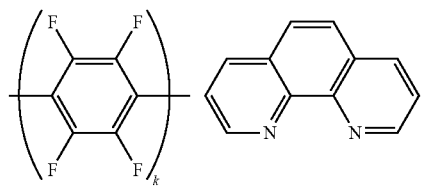

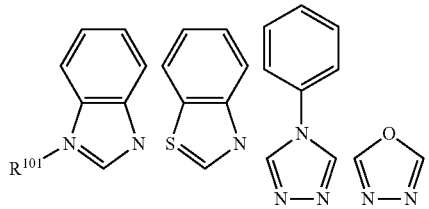

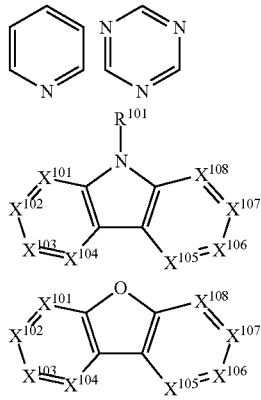

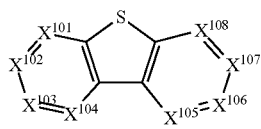

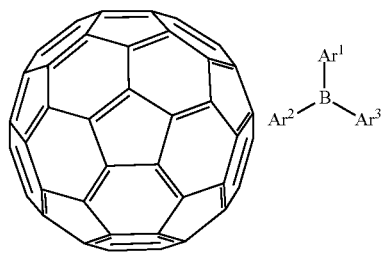

R¹⁰¹ is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, when it is aryl or heteroaryl, it has the similar definition as Ar's mentioned above.

Ar¹ to Ar³ has the similar definition as Ar's mentioned above.

k is an integer from 1 to 20.

X¹⁰¹ to X¹⁰⁸ is selected from C (including CH) or N.

In some embodiments, the metal complexes used in ETL contains, but are not limited to the following general formula:

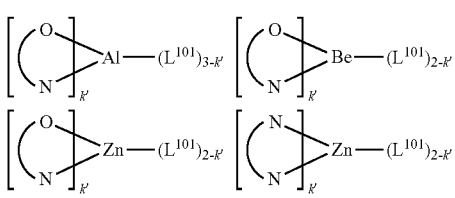

(O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in TABLE 3 below. TABLE 3 lists non-limiting classes of materials, non-limiting examples of compounds for each class, and references that disclose the materials.

TABLE 1

| MATERIAL | EXAMPLES OF MATERIAL | PUBLICATIONS |
|---|---|---|
| Hole injection materials | | |
| Phtalocyanine and porphryin compounds | (Cu phthalocyanine structure) | Appl. Phys. Lett, 69, 2160 (1996) |
| Starburst triarylamines | (triarylamine structure) | J. Lumin. 72-74, 985 (1997) |
| $CF_x$ Fluorohydrocarbon polymer | $-[CH_xF_y]_n-$ | App. Phys. Lett. 78, 673 (2001) |

TABLE 1-continued
| MATERIAL | EXAMPLES OF MATERIAL | PUBLICATIONS |
| --- | --- | --- |
| Conducting polymers (e.g, PEDOT:PSS, polyaniline, polypthiophene) | 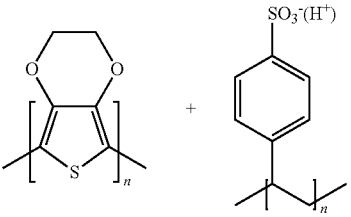 | Synth. Met. 87, 171 (1997) WO2007002683 |
| Phosphonic acid and sliane SAMs | 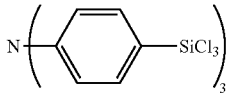 | US20030162053 |
| Triarylamine or polythiophene polymers with conductivity dopants | 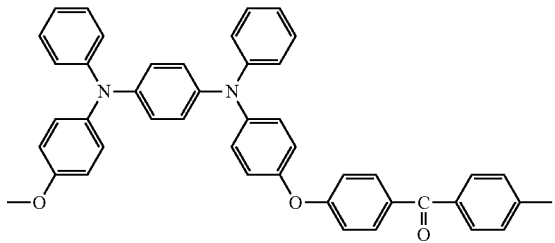 and 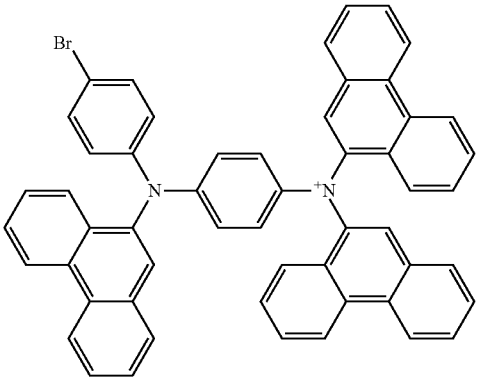 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | EP1725079A1 |

TABLE 1-continued

| MATERIAL | EXAMPLES OF MATERIAL | PUBLICATIONS |
|---|---|---|
| Organic compounds with conductive inorganic compounds, such as molybdenum and tungsten oxides | + MoO$_x$ | US20050123751<br>SID Symposium Digest, 37, 923 (2006)<br>WO2009018009 |
| n-type semiconducting organic complexes | | US20020158242 |
| Metal organometallic complexes | | US20060240279 |
| Cross-linkable compounds | | US20080220265 |

TABLE 1-continued
| MATERIAL | EXAMPLES OF MATERIAL | PUBLICATIONS |
|---|---|---|
| Polythiophene based polymers and copolymers | 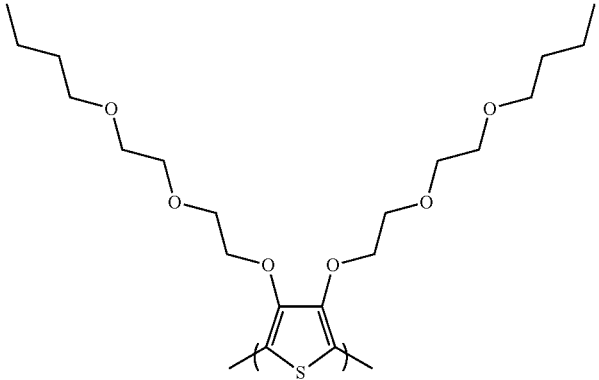 | WO 2011075644<br>EP2350216 |
| Hole transporting material | | |
| Triarylamines (e.g., TPD, α-NPD) | 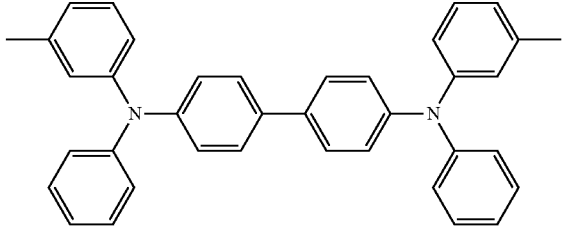 | Appl. Phys. Lett. 51, 913 (1987) |
| | 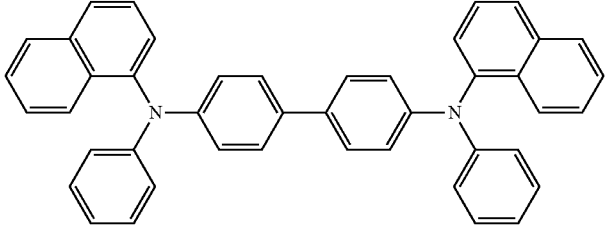 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 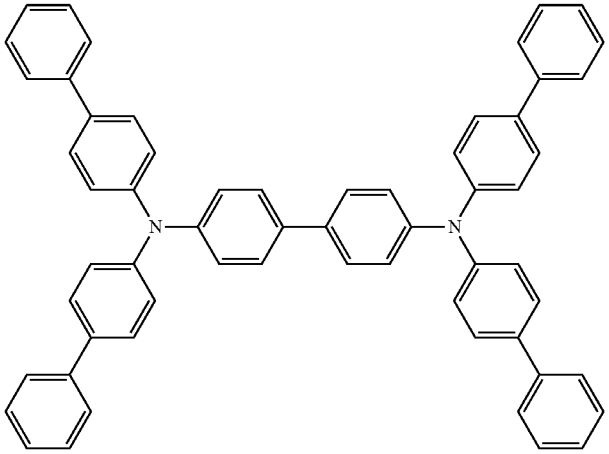 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |

TABLE 1-continued
| MATERIAL | EXAMPLES OF MATERIAL | PUBLICATIONS |
|---|---|---|
| | 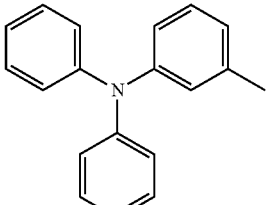 | J. Mater. Chem. 3, 319 (1993) |
| | 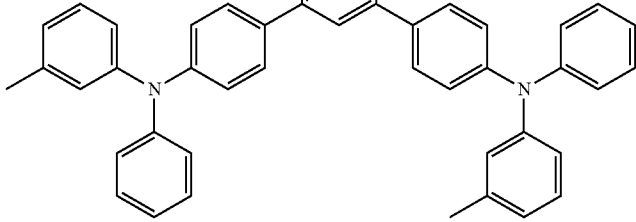 | Appl. Phys. Lett. 90, 183503 (2007) |
| | 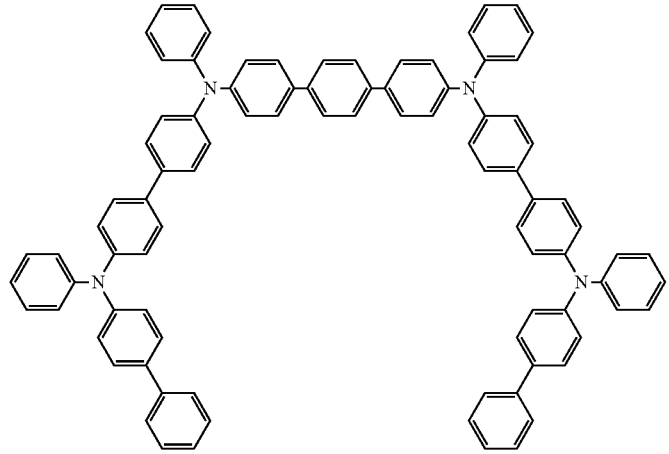 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |
| Triarylamine on spirofluorence core | 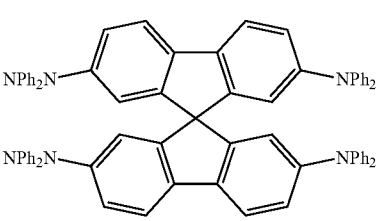 | Synth. Met. 91, 209 (1997) |

TABLE 1-continued

| MATERIAL | EXAMPLES OF MATERIAL | PUBLICATIONS |
| --- | --- | --- |
| Arylamine carbazole compounds | | Adv. Mater. 6, 677 (1994), US20080124572 |
| Triarylamine with (di)benzothiophene/ (di)benzofuran | | US20070278938, US20080106190 US20110163302 |
| Indolocarbazoles | | Synth. Met. 111, 421 (2000) |
| Isoindole compounds | | Chem. Mater. 15, 3148 (2003) |

TABLE 1-continued

| MATERIAL | EXAMPLES OF MATERIAL | PUBLICATIONS |
| --- | --- | --- |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |
| Metal 8-hydroxy-quinolates (e.g., Alq$_3$, BAlq) | | Nature 395, 151 (1998) |
| | | US20060202194 |
| | | WO2005014551 |
| | | WO2006072002 |

TABLE 1-continued

| MATERIAL | EXAMPLES OF MATERIAL | PUBLICATIONS |
|---|---|---|
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
|---|---|---|
| Arylcarbazoles | | Appl. Phys. Lett 78, 1622 (2001) |

TABLE 1-continued
| MATERIAL | EXAMPLES OF MATERIAL | PUBLICATIONS |
|---|---|---|
| | 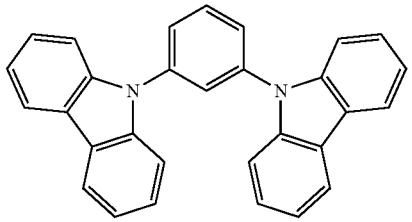 [SMILES: c1cc(-n2c3ccccc3c3ccccc32)cc(-n2c3ccccc3c3ccccc32)c1] | US20030175553 |
| | 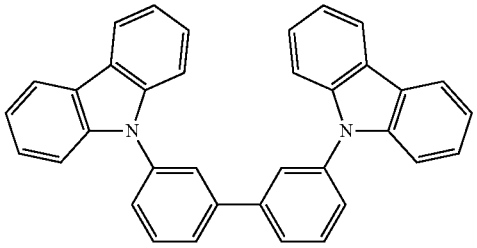 [SMILES: c1cc(-c2cccc(-n3c4ccccc4c4ccccc43)c2)cc(-n2c3ccccc3c3ccccc32)c1] | WO2001039234 |
| Aryltriphenylene compounds | 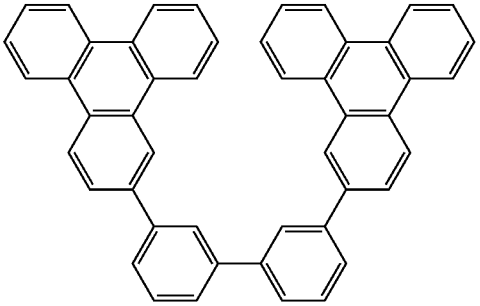 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 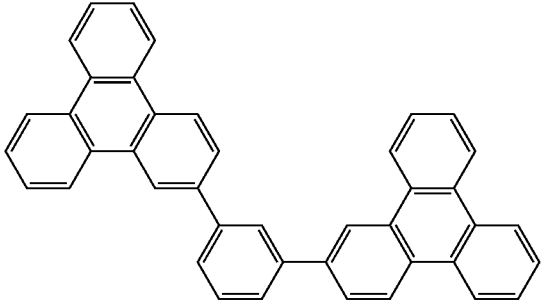 [SMILES: c1cc(-c2ccc3c4ccccc4c4ccccc4c3c2)cc(-c2ccc3c4ccccc4c4ccccc4c3c2)c1] | US20060280965 |
| | 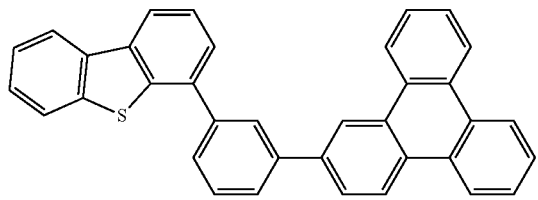 [SMILES: c1cc(-c2ccc3c4ccccc4c4ccccc4c3c2)cc(-c2cccc3c2sc2ccccc23)c1] | WO2009021126 |

| MATERIAL | EXAMPLES OF MATERIAL | PUBLICATIONS |
|---|---|---|
| Poly-fused heteroaryl compounds | 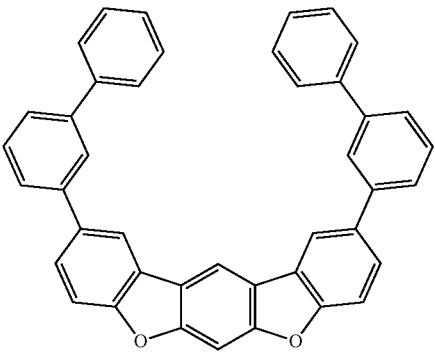 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 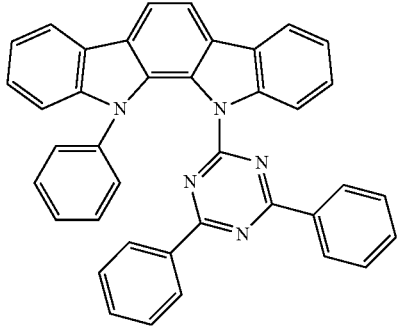 [SMILES: c1ccc(-c2nc(-c3ccccc3)nc(-n3c4ccccc4c4ccc5c6ccccc6n(-c6ccccc6)c5c43)n2)cc1] | WO2008056746 |
|  | 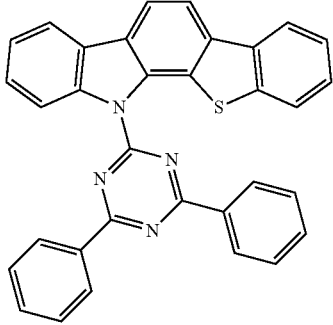 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 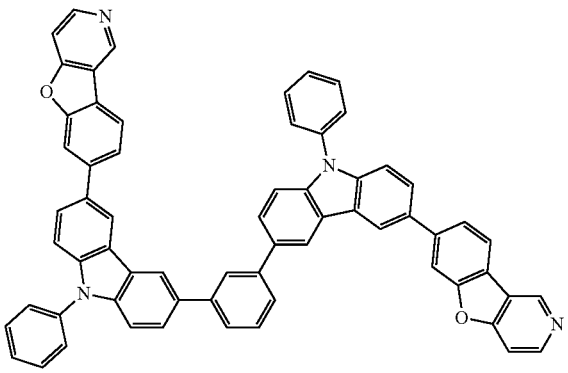 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |

TABLE 1-continued

| MATERIAL | EXAMPLES OF MATERIAL | PUBLICATIONS |
|---|---|---|
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |
| | | WO2006132173 |
| | | JP200511610 |

TABLE 1-continued

| MATERIAL | EXAMPLES OF MATERIAL | PUBLICATIONS |
|---|---|---|
| Spirofluorene-carbazole compounds | | JP2007254297 |
| | | JP2007254297 |
| Indolocarbazoles | | WO2007063796 |
| | | WO2007063754 |
| 5-member ring electron deficient heterocyles (e.g., triazole, oxadiazole) | | J. Appl. Phys. 90, 5048 (2001) |

TABLE 1-continued
| MATERIAL | EXAMPLES OF MATERIAL | PUBLICATIONS |
|---|---|---|
| | 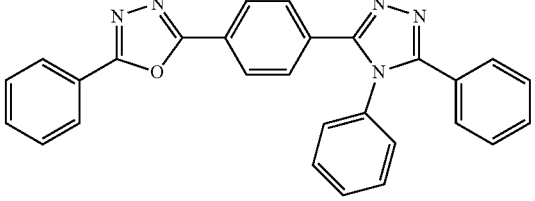 | WO2004107822 |
| Tetraphenylene complexes | 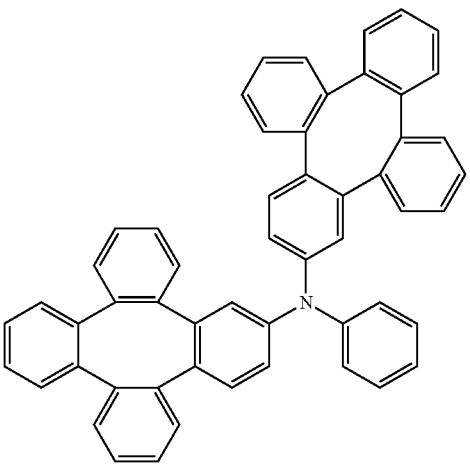 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 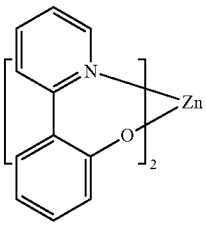 | WO2005030900 |
| Metal coordination complexes (e.g., Zn, Al with NN ligands) | 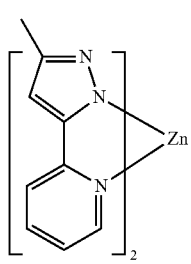 | US20040137268, US20040137267 |
Blue hosts
| | | |
|---|---|---|
| Arylcarbazoles | 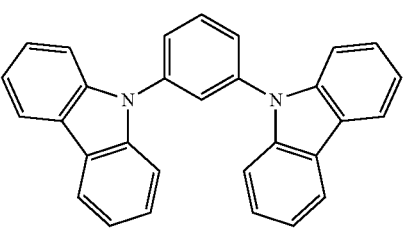 [SMILES: c1cc(-n2c3ccccc3c3ccccc32)cc(-n2c3ccccc3c3ccccc32)c1] | Appl. Pys. Lett, 82, 2422 (2003) |

| MATERIAL | EXAMPLES OF MATERIAL | PUBLICATIONS |
|---|---|---|
| | 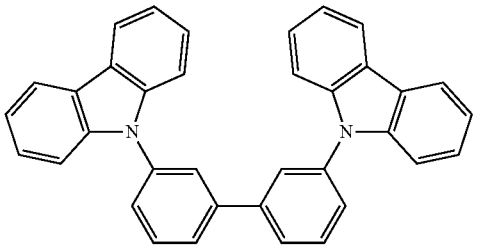 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 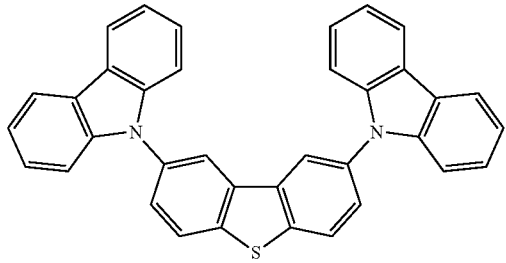 [SMILES: c1ccc2c(c1)c1ccccc1n2-c1ccc2sc3ccc(-n4c5ccccc5c5ccccc54)cc3c2c1] | WO2006114966, US20090167162 |
| | 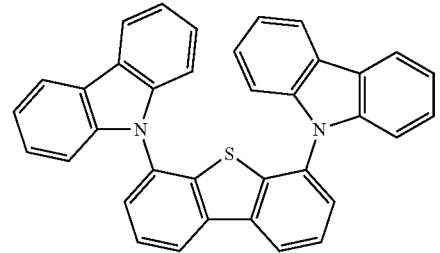 [SMILES: c1cc(-n2c3ccccc3c3ccccc32)c2sc3c(-n4c5ccccc5c5ccccc54)cccc3c2c1] | US20090167162 |
| | 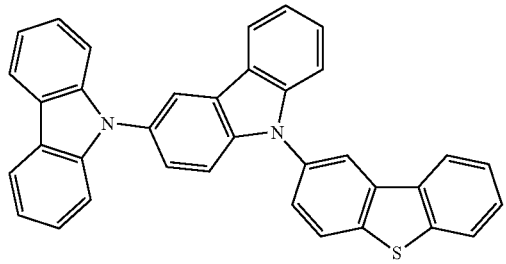 [SMILES: c1ccc2c(c1)sc1ccc(-n3c4ccccc4c4cc(-n5c6ccccc6c6ccccc65)ccc43)cc12] | WO2009086028 |
| | 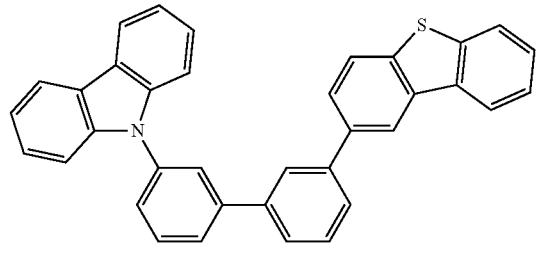 [SMILES: c1cc(-c2cccc(-n3c4ccccc4c4ccccc43)c2)cc(-c2ccc3sc4ccccc4c3c2)c1] | US20090030202, US20090017330 |

TABLE 1-continued
| MATERIAL | EXAMPLES OF MATERIAL | PUBLICATIONS |
|---|---|---|
|  | 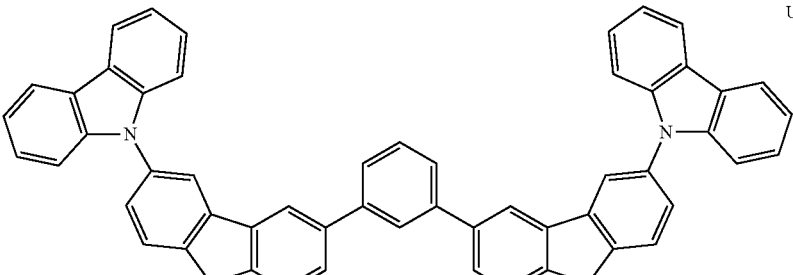 | US20100084966 |
| Silicon aryl compounds | 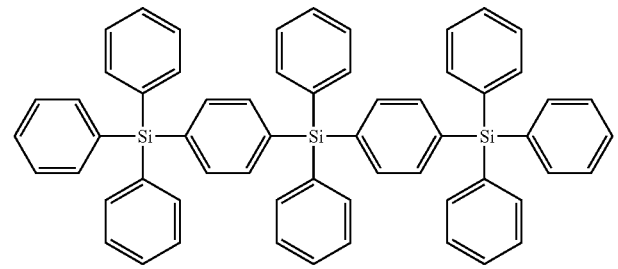 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
|  | 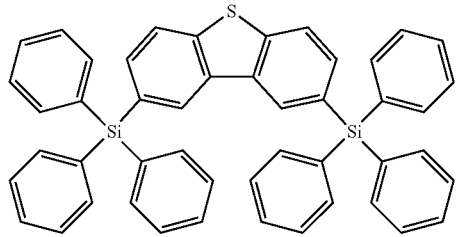 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/ Germanium aryl compounds | 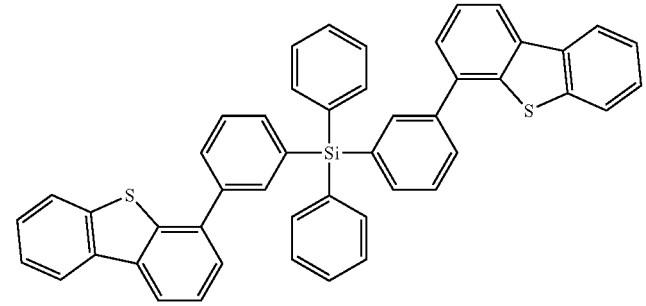 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 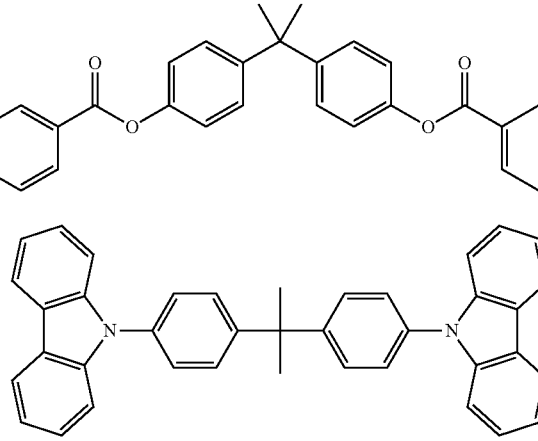 | WO2006100298 |
| Carbazole linked by non-conjugated groups | | US20040115476 |

TABLE 1-continued

| MATERIAL | EXAMPLES OF MATERIAL | PUBLICATIONS |
|---|---|---|
| Aza-carbzoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |
| | | US2006835469 |

TABLE 1-continued

| MATERIAL | EXAMPLES OF MATERIAL | PUBLICATIONS |
|---|---|---|
| | | US2006835469 |
| | | US20060202194 |
| | | US20060202194 |
| | | US20070087321 |
| | | US20080261076<br>US20100090591 |

| MATERIAL | EXAMPLES OF MATERIAL | PUBLICATIONS |
|---|---|---|
| | 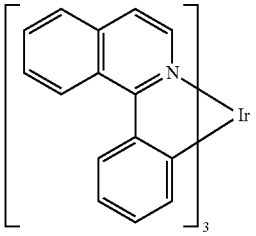 | US20070087321 |
| | 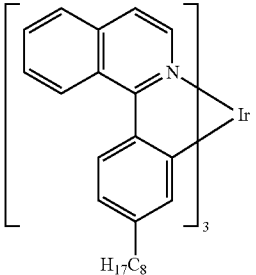 | Adv. Mater. 19, 739 (2007) |
| | 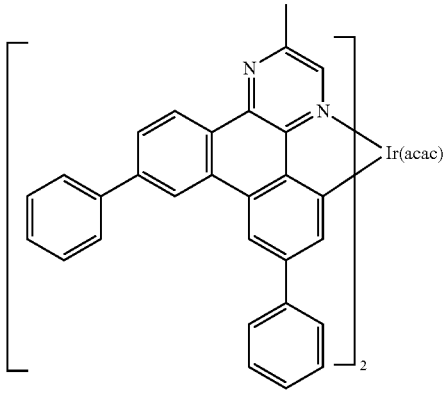 | WO2009100991 |
| | 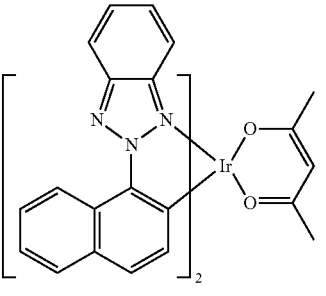 | WO2008101842 |
| | 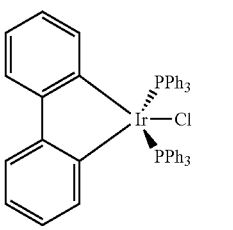 | U.S. Pat. No. 7,232,618 |

TABLE 1-continued
| MATERIAL | EXAMPLES OF MATERIAL | PUBLICATIONS |
|---|---|---|
| Platinum (II) organometallic complexes | 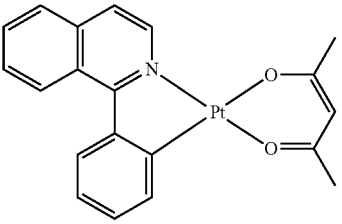 | WO2003040257 |
| | 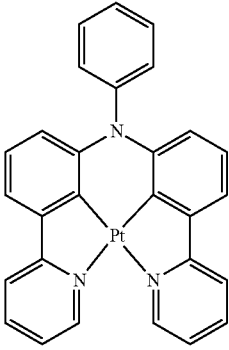 | US20070103060 |
| Osmium(III) complexes | 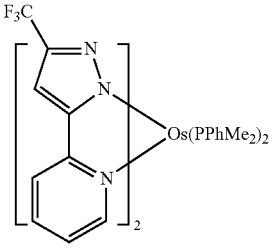 | Chem. Mater. 17, 3532 (2005) |
| Ruthenium(II) complexes | 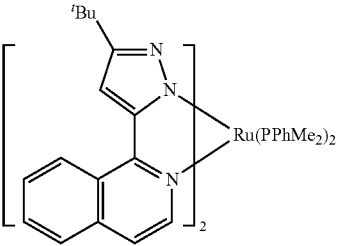 | Adv. Mater. 17, 1059 (2005) |
| Rhenium (I), (II), and (III) complexes | 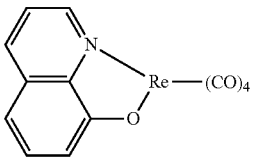 | US20050244673 |
Green dopants

TABLE 1-continued
| MATERIAL | EXAMPLES OF MATERIAL | PUBLICATIONS |
| --- | --- | --- |
| Iridium(III) organometallic complexes | 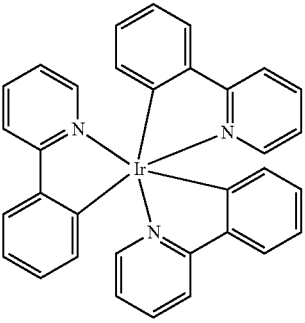<br>and its derivatives | Inorg. Chem. 40, 1704 (2001) |
| | 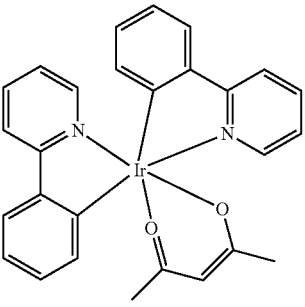 | US20020034656 |
| | 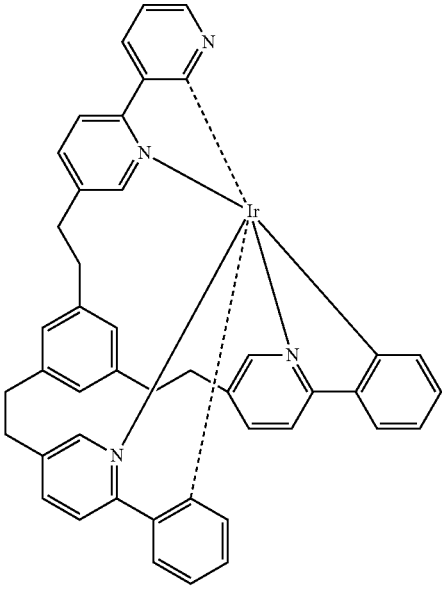 | U.S. Pat. No. 7,332,232 |
| | 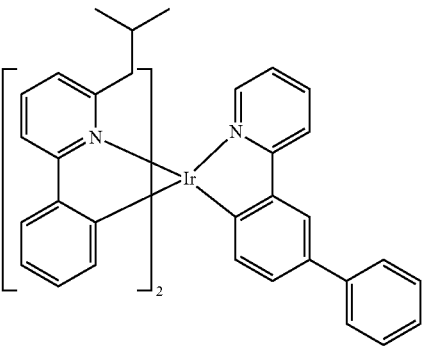 | US20090108737 |

TABLE 1-continued

| MATERIAL | EXAMPLES OF MATERIAL | PUBLICATIONS |
|---|---|---|
| | | WO2010028151 |
| | | EP1841834B |
| | | US20060127696 |
| | | US20090039776 |
| | | U.S. Pat. No. 6,921,915 |

TABLE 1-continued

| MATERIAL | EXAMPLES OF MATERIAL | PUBLICATIONS |
| --- | --- | --- |
| | | US20100244004 |
| | | U.S. Pat. No. 6,687,266 |
| | | Chem. Mater. 16, 2480 (2004) |
| | | US20070190359 |
| | | US20060008670<br>JP2007123392 |
| | | WO2010086089,<br>WO2011044988 |

TABLE 1-continued

| MATERIAL | EXAMPLES OF MATERIAL | PUBLICATIONS |
|---|---|---|
| | | Adv. Mater. 16, 2003 (2004) |
| | | Angew. Chem. Int. Ed. 2006, 45, 7800 |
| | | WO2009050290 |
| | | US20090165846 |
| | | US20080015355 |
| | | US20010015432 |

TABLE 1-continued
| MATERIAL | EXAMPLES OF MATERIAL | PUBLICATIONS |
|---|---|---|
| | 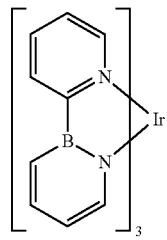 | US20100295032 |
| Monomer for polymeric metal organometallic compounds | 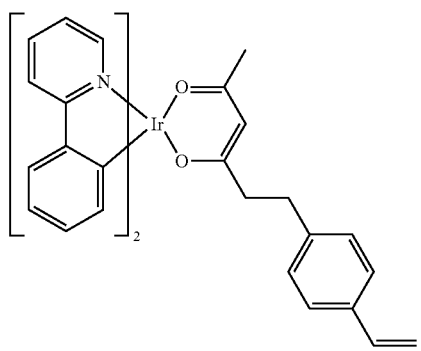 | U.S. Pat. No. 7,250,226, U.S. Pat. No. 7,396,598 |
| Pt(II) organometallic complexes, including polydentated ligands | 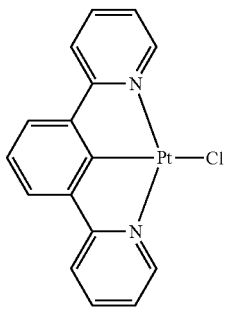 | Appl. Phys. Lett. 86, 153505 (2005) |
| | 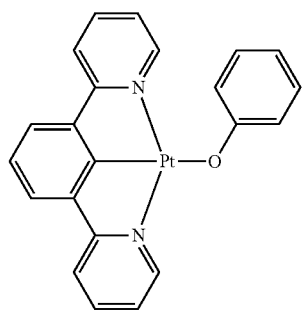 | Appl. Phys. Lett. 86, 153505 (2005) |
| | 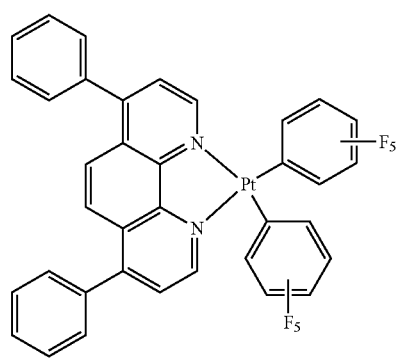 | Chem. Lett. 34, 592 (2005) |

TABLE 1-continued
| MATERIAL | EXAMPLES OF MATERIAL | PUBLICATIONS |
|---|---|---|
| | 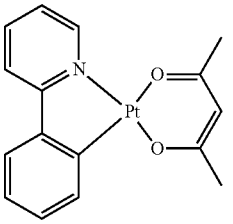 | WO2002015645 |
| | 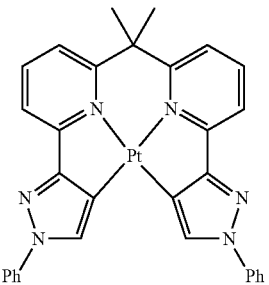 | US20060263635 |
| | 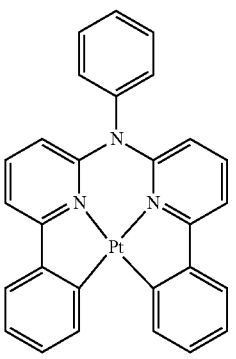 | US20060182992<br>US20070103060 |
| Cu complexes | 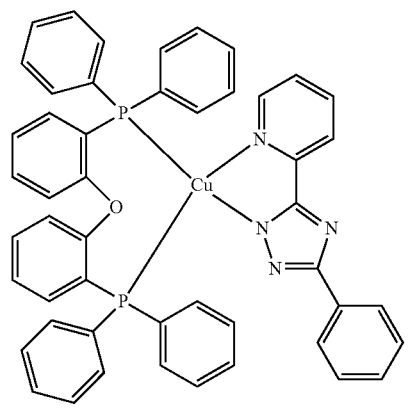 | WO2009000673 |

| MATERIAL | EXAMPLES OF MATERIAL | PUBLICATIONS |
|---|---|---|
| | 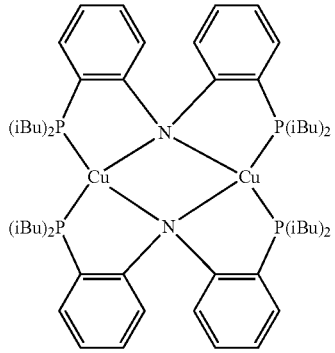 | US20070111026 |
| Gold complexes | 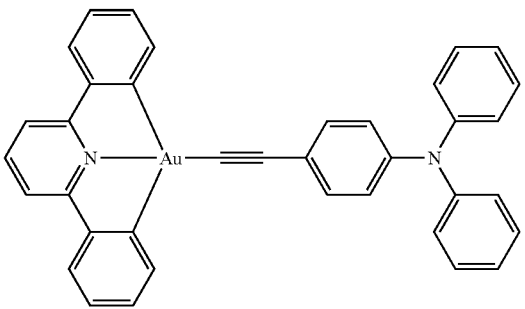 | Chem. Commun. 2906 (2005) |
| Rhenium(III) complexes | 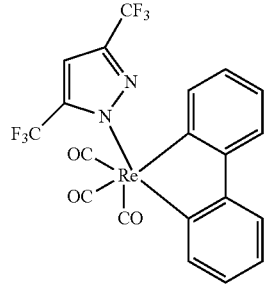 | Inorg. Chem. 42, 1248 (2003) |
| Osmium(II) complexes | 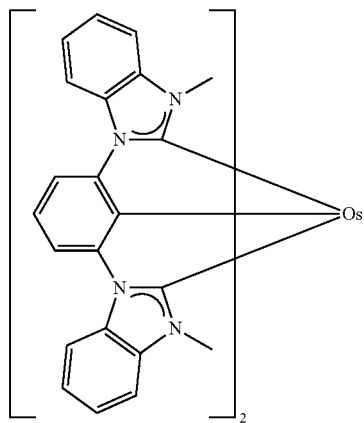 | U.S. Pat. No. 7,279,704 |

TABLE 1-continued

| MATERIAL | EXAMPLES OF MATERIAL | PUBLICATIONS |
| --- | --- | --- |
| Deuterated organometallic complexes | | US20030138657 |
| Organometallic complexes with two or more metal centers | | US20030152802 |
| | | U.S. Pat. No. 7,090,928 |

Blue dopants

| | | |
| --- | --- | --- |
| Iridium(III) organometallic complexes | | WO2002002714 |

TABLE 1-continued

| MATERIAL | EXAMPLES OF MATERIAL | PUBLICATIONS |
|---|---|---|
| | | WO2006009024 |
| | | US20060251923<br>US20110057559<br>US20110204333 |
| | | U.S. Pat. No. 7,393,599,<br>WO2006056418,<br>US20050260441,<br>WO2005019373 |
| | | U.S. Pat. No. 7,534,505 |
| | | WO2011051404 |
| | | U.S. Pat. No. 7,445,855 |

TABLE 1-continued
| MATERIAL | EXAMPLES OF MATERIAL | PUBLICATIONS |
|---|---|---|
| | 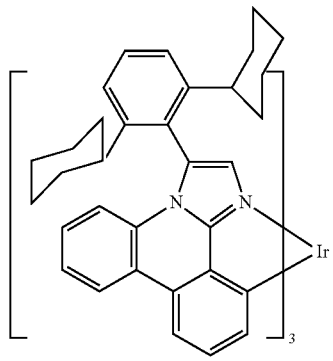 | US20070190359, US20080297033 US20100148663 |
| | 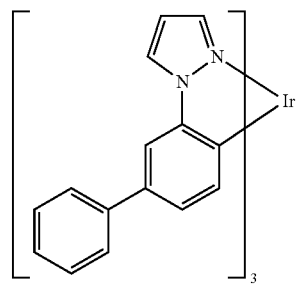 | U.S. Pat. No. 7,338,722 |
| | 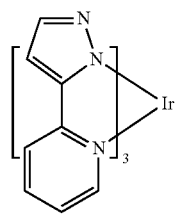 | US20020134984 |
| | 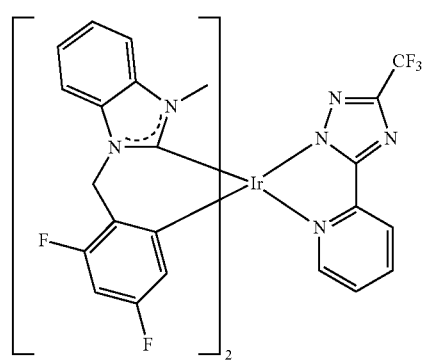 | Angew. Chem. Int. Ed. 47, 4542 (2008) |
| | 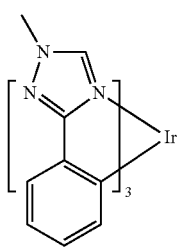 | Chem. Mater. 18, 5119 (2006) |

TABLE 1-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |
| | | WO2007004380 |
| | | WO2006082742 |

TABLE 1-continued

| MATERIAL | EXAMPLES OF MATERIAL | PUBLICATIONS |
|---|---|---|
| Osmium(II) complexes | | U.S. Pat. No. 7,279,704 |
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |

Exciton/hole blocking layer materials

| | | |
|---|---|---|
| Bathocuprine compounds (e.g., BCP, BPhen) | | Appl. Phys. Lett. 75, 4 (1999) |

TABLE 1-continued

| MATERIAL | EXAMPLES OF MATERIAL | PUBLICATIONS |
|---|---|---|
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxidiazole, imidazole, benzoimidazolee | | Appl. Phys. Lett. 81, 162 (2002) |
| Triphenylene compounds | | US20050025993 |

TABLE 1-continued
| MATERIAL | EXAMPLES OF MATERIAL | PUBLICATIONS |
|---|---|---|
| Fluorinated aromatic compounds | 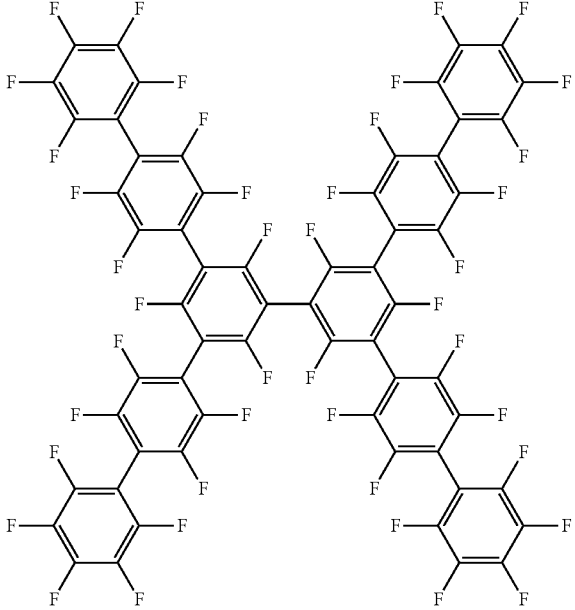 [SMILES: Fc1c(F)c(F)c(-c2c(F)c(F)c(-c3c(F)c(-c4c(F)c(F)c(-c5c(F)c(F)c(F)c(F)c5F)c(F)c4F)c(F)c(-c4c(F)c(-c5c(F)c(F)c(-c6c(F)c(F)c(F)c(F)c6F)c(F)c5F)c(F)c(-c5c(F)c(F)c(-c6c(F)c(F)c(F)c(F)c6F)c(F)c5F)c4F)c3F)c(F)c2F)c(F)c1F] | Appl. Phys. Lett. 79, 156 (2001) |
| Phenothiazine-S-oxide | 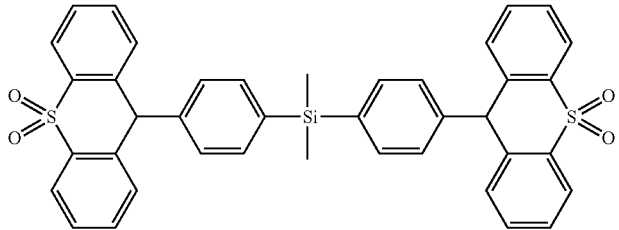 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silyalted five-membered nitrogen, oxygen, sulfur or phosphorus dibenzoheterocycles | 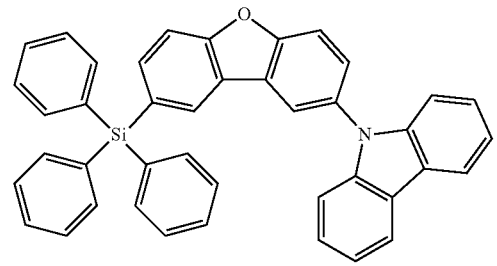 [SMILES: c1ccc([Si](c2ccccc2)(c2ccccc2)c2ccc3oc4ccc(-n5c6ccccc6c6ccccc65)cc4c3c2)cc1] | WO2010079051 |
| Aza-carbazoles | 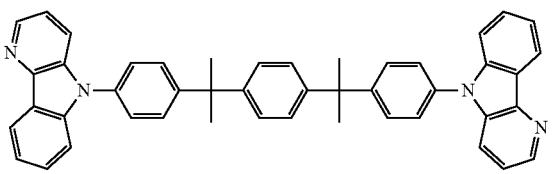 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
Electron transporting materials

TABLE 1-continued

| MATERIAL | EXAMPLES OF MATERIAL | PUBLICATIONS |
| --- | --- | --- |
| Anthracene-benzoimidazole compounds | | WO2003060956 |
| | | US20090179554 |
| Aza triphenylene derivatives | | US20090115316 |
| Anthracene-benzothiazole compounds | | Appl. Phys. Lett. 89, 063504 (2006) |
| Metal 8-hydroxyquinolates (e.g., Alq$_3$, Zrq$_4$) | | Appl. Phys. Lett. 51, 913 (1987) US7230107 |

TABLE 1-continued

| MATERIAL | EXAMPLES OF MATERIAL | PUBLICATIONS |
|---|---|---|
| Metal hydroxybenzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued
| MATERIAL | EXAMPLES OF MATERIAL | PUBLICATIONS |
|---|---|---|
| Silole compounds | 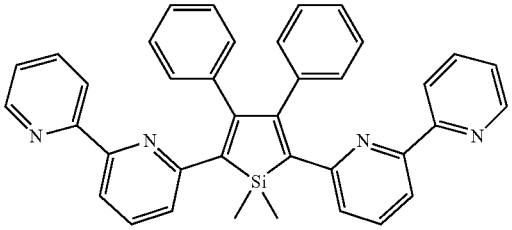 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 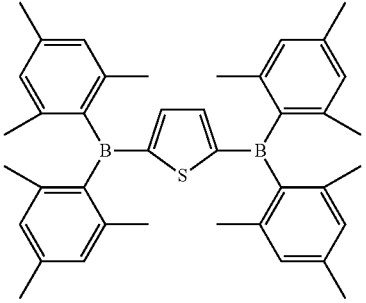 | J. Am. Chem. Soc. 120, 9714 (1998) |
| Fluorinated aromatic compounds | 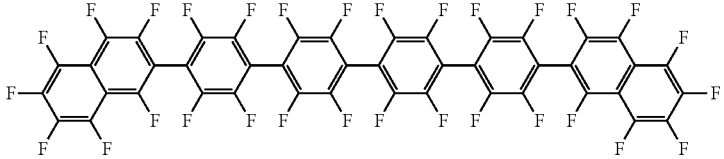 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem Soc. 122, 1832 (2000) |
| Fullerene (e.g., C60) | 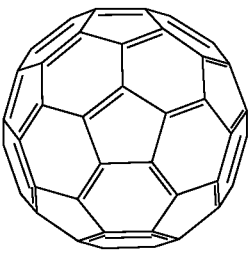 | US20090101870 |
| Triazine complexes | 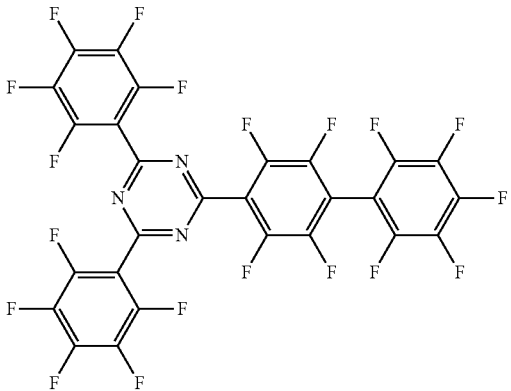 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE 1-continued

| MATERIAL | EXAMPLES OF MATERIAL | PUBLICATIONS |
| --- | --- | --- |
| Zn (NN) complexes | 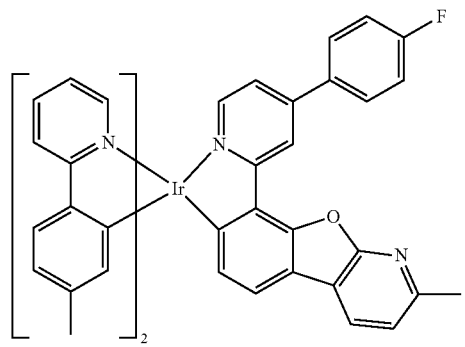 | U.S. Pat. No. 6,528,187 |

EXPERIMENTAL

Compound Examples

Chemical abbreviations used throughout this document are as follows: DMF is dimethylformamide and DCM is dichloromethane.

Example 1

Synthesis of Compound I-1

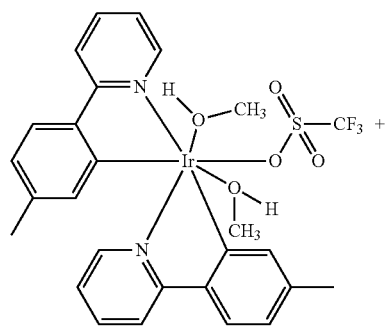 +

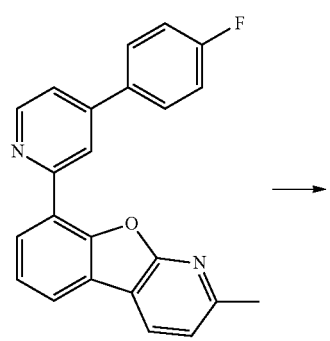

-continued

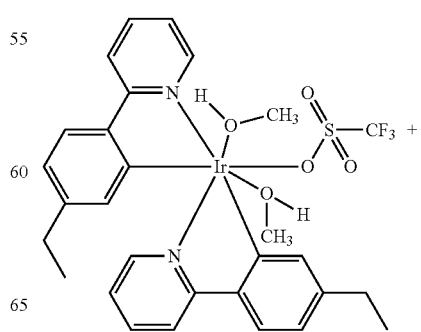

Compound I-1

A mixture of iridium precursor (The synthesis was disclosed in US2011227049) (2.5 g, 3.37 mmol), 8-(4-(4-fluorophenyl)pyridin-2-yl)-2-methylbenzofuro[2,3-b]pyridine (2.15 g, 6.07 mmol), 2-ethoxyethanol (40 mL), and DMF (40 mL) was heated at 130° C. overnight. The solvent mixture was evaporated under vacuum. The residue was run through a short silica plug. The mixture obtained was further purified by silica gel column with DCM/Heptane as eluent to obtain Compound I-1 (1.8 g, 60.6% yield) which was confirmed by LC-MS.

Example 2

Synthesis of Compound I-2

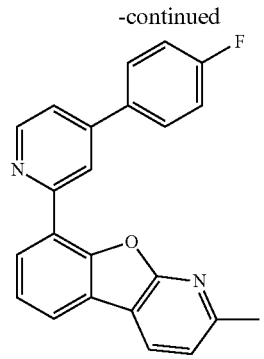

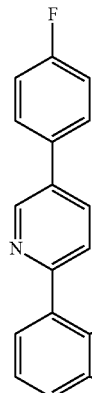

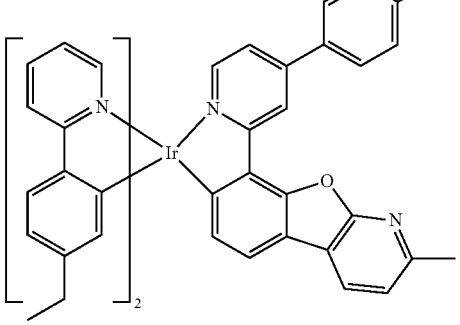

Compound I-2

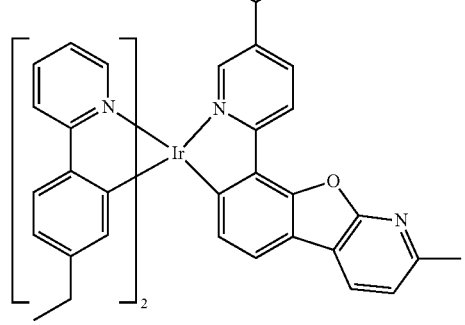

Compound I-3

A mixture of iridium precursor (2.5 g, 3.25 mmol), 8-(4-(4-fluorophenyl)pyridin-2-yl)-2-methylbenzofuro[2,3-b]pyridine (2.071 g, 5.85 mmol), 2-ethoxyethanol (40 mL), and DMF (40 mL) was heated at 130° C. overnight. The solvent mixture was evaporated under vacuum. The residue was run through a short silica plug. The mixture obtained was further purified by silica gel column with DCM/Heptane as eluent to obtain Compound I-2 (1.88 g, 63.6% yield) which was confirmed by LC-MS.

Example 3

Synthesis of Compound I-3

A mixture of iridium precursor (2.5 g, 3.25 mmol), 8-(5-(4-fluorophenyl)pyridin-2-yl)-2-methylbenzofuro[2,3-b]pyridine (2.071 g, 5.85 mmol), 2-ethoxyethanol (40 mL), and DMF (40 mL) was heated at 130° C. overnight. The solvent mixture was evaporated under vacuum. The residue was run through a short silica plug. The mixture obtained was further purified by silica gel column with DCM/Heptane as eluent to obtain Compound I-3 (1.75 g, 59.2% yield) which was confirmed by LC-MS.

Example 4

Synthesis of Compound I-4

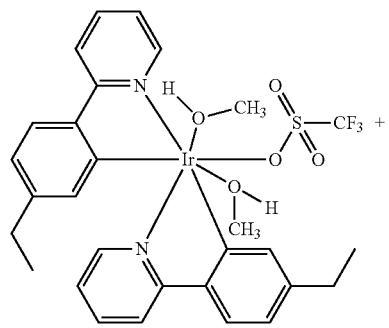

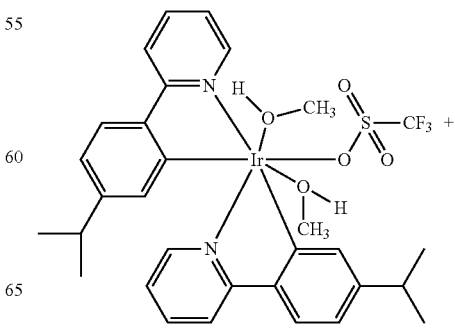

225

-continued

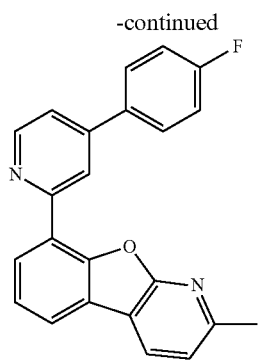

→

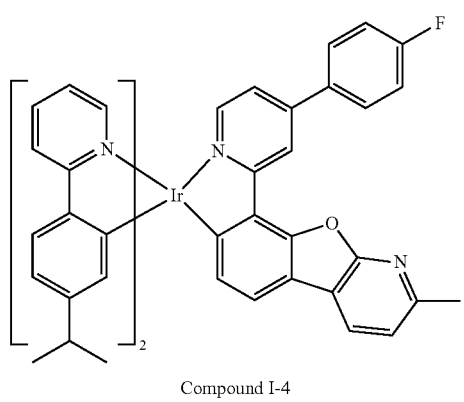

Compound I-4

A mixture of iridium precursor (2.0 g, 2.507 mmol), 8-(4-(4-fluorophenyl)pyridin-2-yl)-2-methylbenzofuro[2,3-b]pyridine (1.599 g, 4.51 mmol), 2-ethoxyethanol (25 mL), and DMF (25 mL) was heated at 130° C. overnight. The solvent mixture was evaporated under vacuum. The residue was run through a short silica plug. The mixture obtained was further purified by silica gel column with DCM/Heptane as eluent to obtain Compound I-4 (1.18 g, 50.2% yield) which was confirmed by LC-MS.

Example 5

Synthesis of Compound I-5

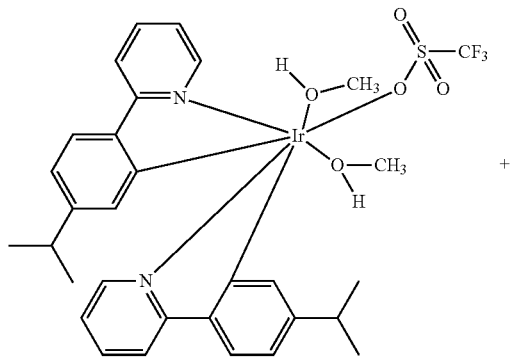

226

-continued

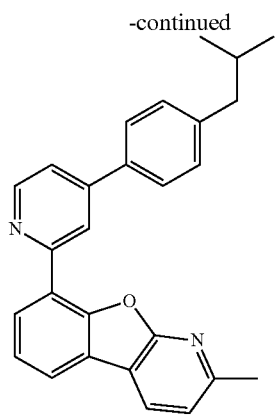

⇢

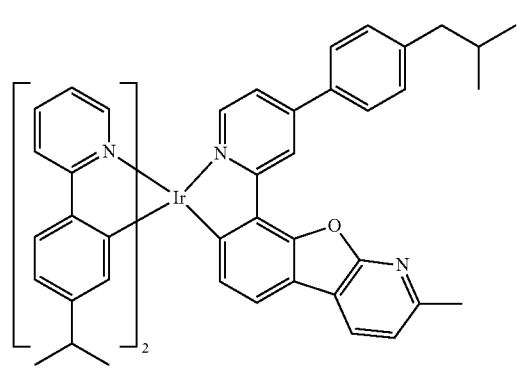

Compound I-5

A mixture of iridium precursor (1.55 g, 1.943 mmol), 8-(4-(4-isobutylphenyl)pyridin-2-yl)-2-methylbenzofuro[2,3-b]pyridine (1.525 g, 3.89 mmol), and ethanol (60 mL) was heated at 85° C. for 3 days. The solvent mixture was evaporated under vacuum. The residue was run through a short silica plug. The mixture obtained was further purified by silica gel column with DCM/Heptane as eluent to obtain Compound I-5 (1.0 g, 52.7% yield) which was confirmed by LC-MS.

Example 6

Synthesis of Compound I-6

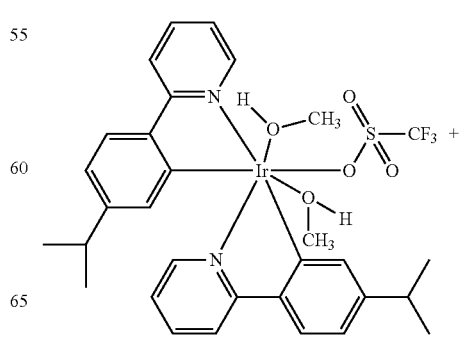

227
-continued

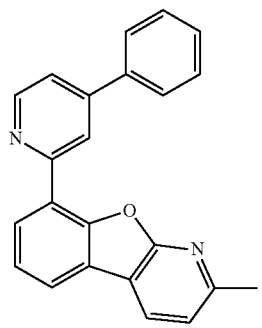

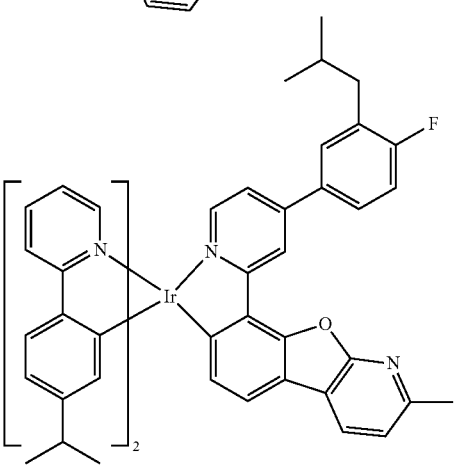

Compound I-6

A mixture of iridium precursor (2.2 g, 2.76 mmol), 2-methyl-8-(4-phenylpyridin-2-yl)benzofuro[2,3-b]pyridine (1.669 g, 4.96 mmol), and ethanol (100 mL) was heated at 85° C. for 3 days. The solvent mixture was evaporated under vacuum. The residue was run through a short silica plug. The mixture obtained was further purified by silica gel column with DCM/Heptane as eluent to obtain Compound I-6 (1.1 g, 43.4% yield) which was confirmed by LC-MS.

Example 7

Synthesis of Compound I-7

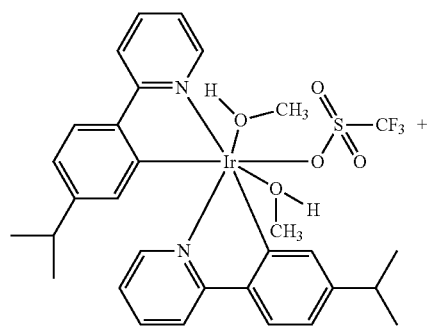

228
-continued

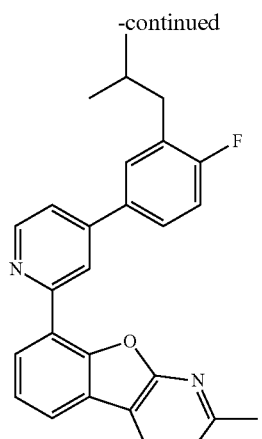

Compound I-7

A mixture of iridium complex (1.8 g, 2.256 mmol), 8-(4-(4-fluoro-3-isobutylphenyl)pyridin-2-yl)-2-methylbenzofuro[2,3-b]pyridine (1.482 g, 4.51 mmol), 2-ethoxyethanol (40 mL) and DMF (40 mL) was heated at 130° C. overnight. The solvent mixture was evaporated under vacuum. The residue was run through a short silica plug. The mixture obtained was further purified by silica gel column with DCM/Heptane as eluent to obtain Compound I-7 (1.00 g, 44.6% yield) which was confirmed by LC-MS.

Example 8

Synthesis of Compound I-8

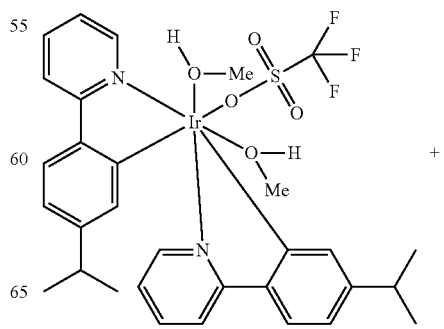

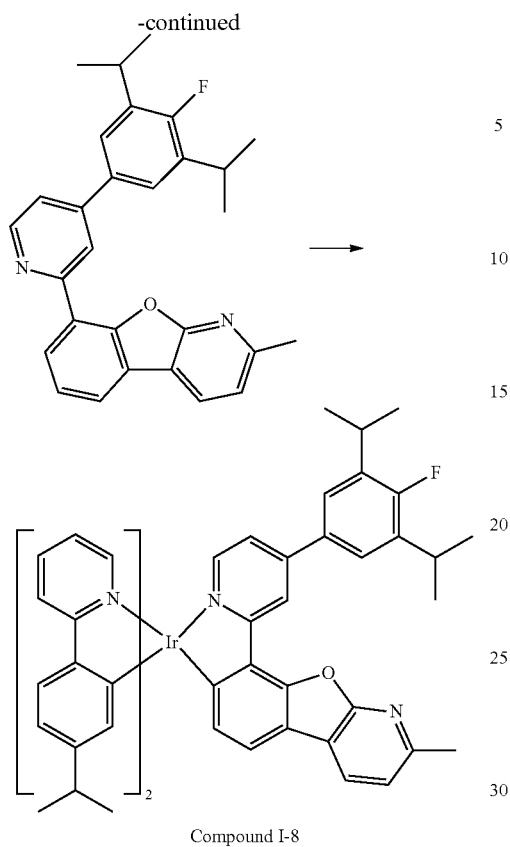

Compound I-8

8-(4-(4-fluoro-3,5-diisopropylphenyl)pyridin-2-yl)-2-methylbenzofuro[2,3-b]pyridine (2.325 g, 5.30 mmol) and the iridium precursor (2.35 g, 2.95 mmol) were charged into the reaction flask with 40 mL of DMF and 40 mL of 2-ethoxyethanol. This mixture was degassed with nitrogen then was heated in an oil bath set at 130° C. for 18 hours. The solvents were removed under vacuum. The crude residue was passed through a silica gel plug. This crude residue was passed through a silica gel column using DCM/heptanes to elute the column. The clean fractions were combined and concentrated under vacuum yielding Compound I-8 (1.6 g, 53.1% yield) as an orange solid. LC/MS analysis confirmed the mass for the desired product.

Example 9

Synthesis of Compound I-9

Compound I-9

A mixture of iridium precursor (2.5 g, 3.13 mmol), 8-(5-(4-fluorophenyl)pyridin-2-yl)-2-methylbenzofuro[2,3-b]pyridine (1.99 g, 5.64 mmol), 2-ethoxyethanol (30 mL), and DMF (30 mL) was heated at 130° C. overnight. The solvent mixture was evaporated under vacuum. The residue was run through a short silica plug. The mixture obtained was further purified by silica gel column with DCM as eluent to obtain Compound I-9 (1.6 g, 57.5% yield) which was confirmed by LC-MS.

Example 10

Synthesis of Compound I-10

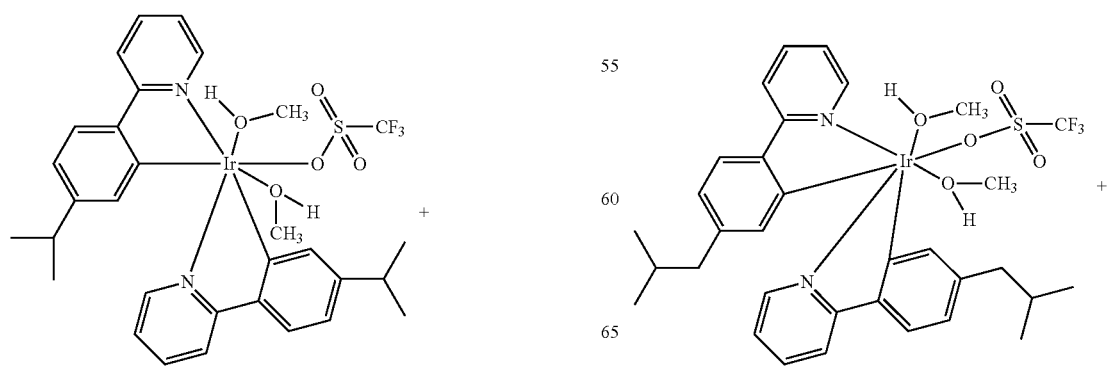

231
-continued

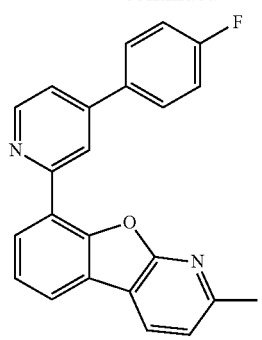

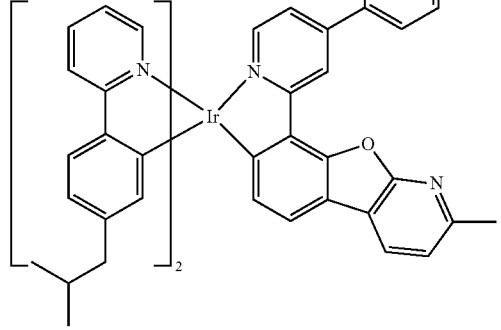

Compound I-10

A mixture of iridium precursor (2.5 g, 3.03 mmol), 8-(4-(4-fluorophenyl)pyridin-2-yl)-2-methylbenzofuro[2,3-b]pyridine (1.931 g, 5.45 mmol), and ethanol (100 mL) was heated at 85° C. for 3 days. The solvent mixture was evaporated under vacuum. The residue was run through a short silica plug. The mixture obtained was further purified by silica gel column with DCM/Heptane as eluent to obtain Compound I-10 (1.3 g, 44.5% yield) which was confirmed by LC-MS.

Example 11

Synthesis of Compound I-11

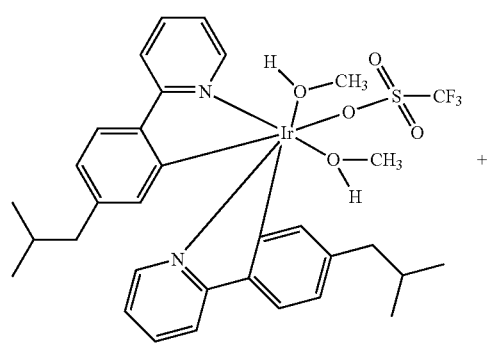

232
-continued

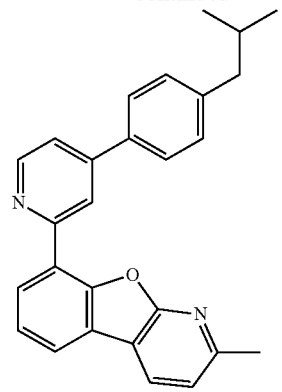

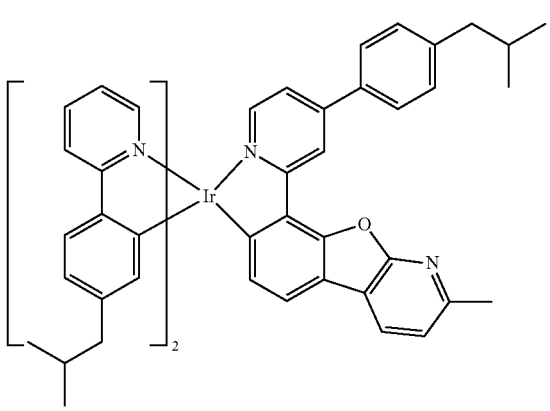

Compound I-11

A mixture of iridium precursor (2.5 g, 3.03 mmol), 8-(4-(4-isobutylphenyl)pyridin-2-yl)-2-methylbenzofuro[2,3-b]pyridine (2.138 g, 5.45 mmol), and ethanol (100 mL) was heated at 85° C. for 3 days. The solvent mixture was evaporated under vacuum. The residue was ran through a short silica plug. The mixture obtained was further purified by silica gel column with DCM/Heptane as eluent to obtain Compound I-11 (2.3 g, 76.0% yield) which was confirmed by LC-MS.

Example 12

Synthesis of Compound I-12

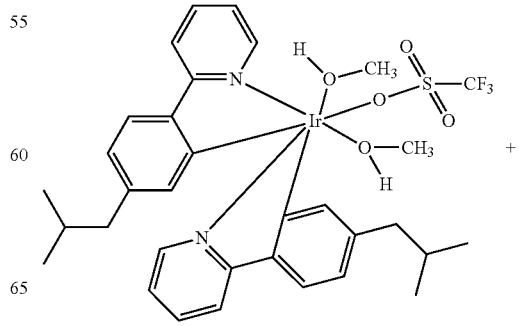

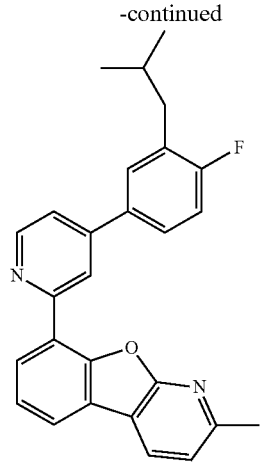

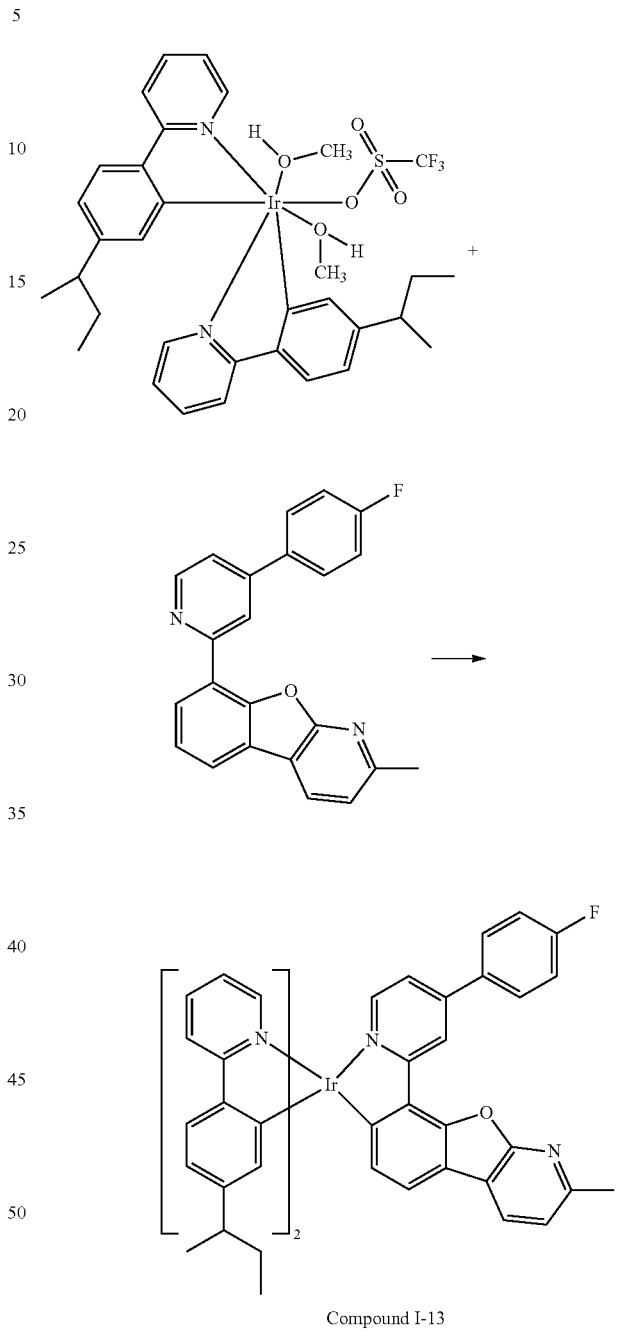

Compound I-12

Example 13

Synthesis of Compound I-13

Compound I-13

A mixture of iridium precursor (1.9 g, 2.30 mmol), 8-(4-(4-fluoro-3-isobutylphenyl)pyridin-2-yl)-2-methylbenzofuro[2,3-b]pyridine (1.51 g, 3.68 mmol), 2-ethoxyethanol (40 mL), and DMF (40 mL) was heated at 130° C. overnight. The solvent mixture was evaporated under vacuum. The residue was run through a short silica plug. The mixture obtained was further purified by silica gel column with DCM/Heptane as eluent to obtain Compound I-12 (1.5 g, 63.8% yield) which was confirmed by LC-MS.

A mixture of iridium precursor (2.5 g, 3.03 mmol), 8-(4-(4-fluorophenyl)pyridin-2-yl)-2-methylbenzofuro[2,3-b]pyridine (1.931 g, 5.45 mmol), and ethanol (120 mL) was heated at 85° C. for 3 days. The solvent mixture was evaporated under vacuum. The residue was run through a short silica plug. The mixture obtained was further purified by silica gel column with DCM/Heptane as eluent to obtain Compound I-13 (0.75 g, 25.7% yield) which was confirmed by LC-MS.

Example 14

Synthesis of Compound I-14

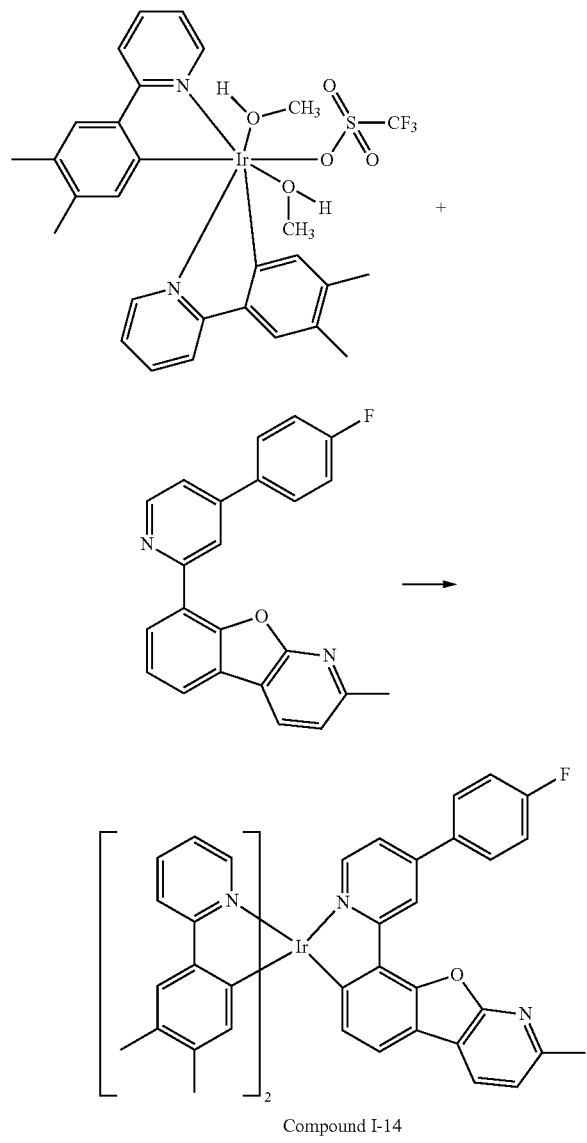

Compound I-14

8-(4-(4-fluorophenyl)pyridin-2-yl)-2-methylbenzofuro[2,3-b]pyridine (1.740 g, 4.91 mmol) and the iridium precursor (2.1 g, 2.73 mmol) were charged into the reaction flask with 100 mL of ethanol. This mixture was degassed with nitrogen then was heated at reflux for 3 days. The solvents were removed under vacuum. The crude residue was passed through a silica gel plug. The filtrate was concentrated under vacuum. This crude residue was passed through a silica gel column using DCM/heptanes to elute the column. The clean fractions were combined and concentrated under vacuum yielding Compound I-14 (0.9 g, 36.3% yield) as an orange solid. LC/MS analysis confirmed the mass for the desired product.

Example 15

Synthesis of Compound I-15

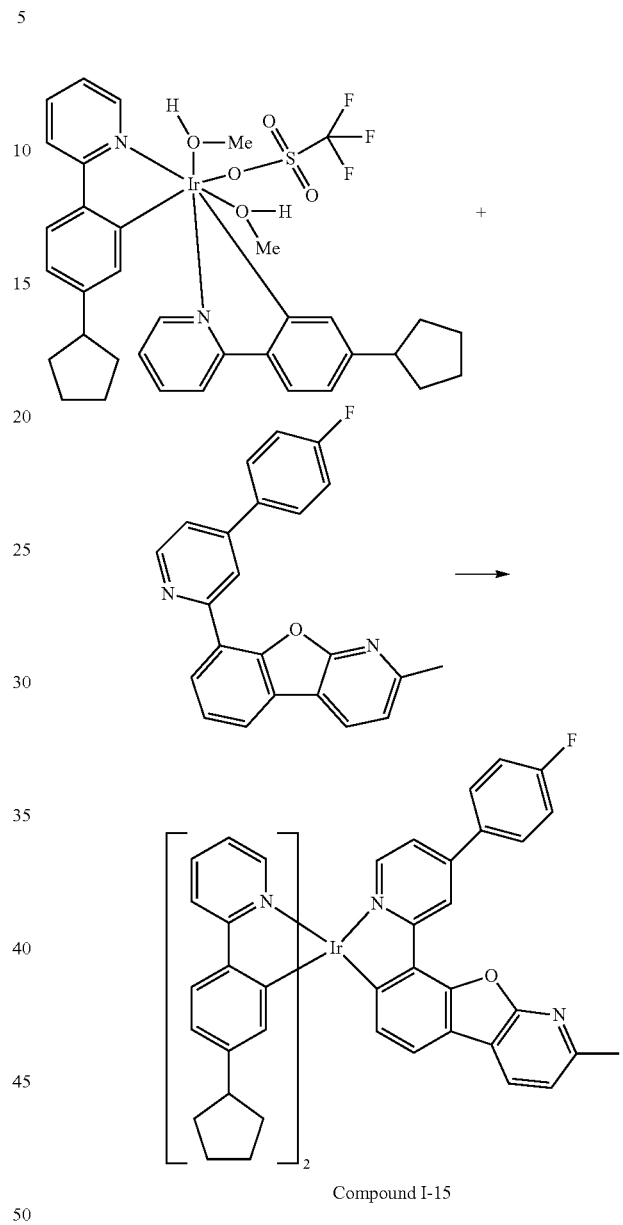

Compound I-15

8-(4-(4-fluorophenyl)pyridin-2-yl)-2-methylbenzofuro[2,3-b]pyridine (1.876 g, 5.29 mmol) and iridium precursor (2.5 g, 2.94 mmol) were charged into the reaction flask with 100 mL of ethanol. This reaction mixture was degassed with nitrogen then was heated in an oil bath set at 85° C. for 3 days. Heating was discontinued. The reaction mixture was concentrated under vacuum. The crude product was dissolved in DCM and was passed through a silica gel plug. This crude product was then passed through 2×300 g silica gel columns eluting with DCM/Heptanes. Clean product fractions were combined and concentrated under vacuum yielding Compound I-15 (1.52 g, 52.2% yield) as an orange solid. LC/MS analysis confirmed the mass for the desired product.

Example 16

Synthesis of Compound I-16

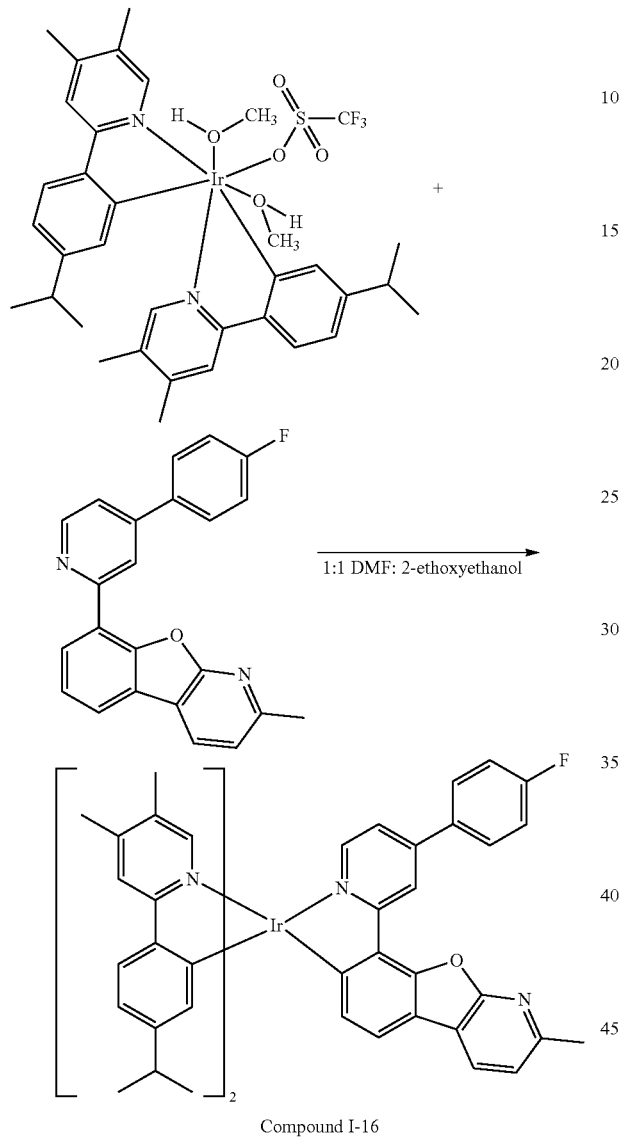

Compound I-16

The iridium precursor (2.0 g, 2.342 mmol), 8-(4-(4-fluorophenyl)pyridin-2-yl)-2-methylbenzofuro[2,3-b]pyridine (1.494 g, 4.22 mmol), DMF 25 mL and 2-ethoxyethanol 25 mL were combined in a 250 mL single neck round bottom flask. A condenser was attached then the system was evacuated and purged with nitrogen three times. The reaction was heated in an oil bath set at 130° C. overnight. The reaction was concentrated down to an orange sludgy solid. The solid was partially dissolved in 200 mL hot DCM and filtered through 200 mg silica gel in fitted Buchner funnel with DCM. The filtrate was concentrated down to 0.84 g of an orange solid. The 0.84 g sample was purified with silica gel using a 75/25 to 25/75 heptane/DCM solvent system to get 0.45 g to an orange-yellow solid for a 19.3% yield. HPLC indicated 99.7% purity and LC/MS indicated it has the correct mass.

Example 17

Synthesis of Compound I-17

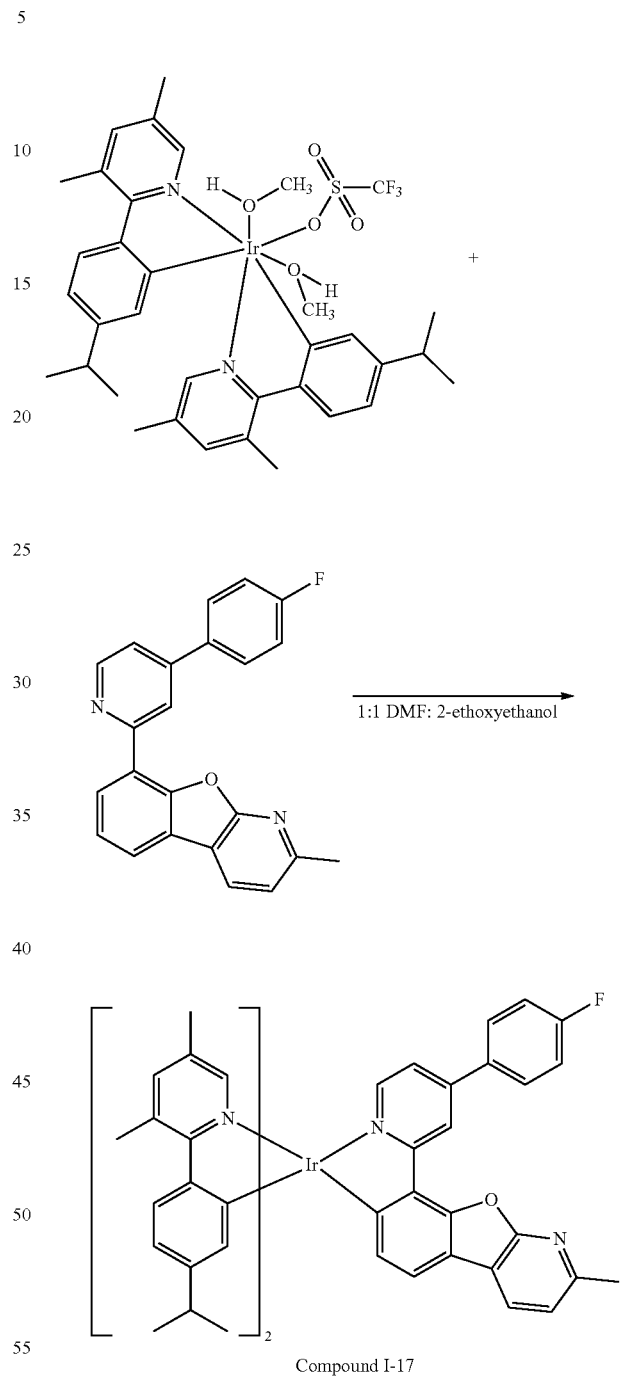

Compound I-17

A mixture of iridium precursor (2.3 g, 2.69 mmol), 8-(4-(4-fluorophenyl)pyridin-2-yl)-2-methylbenzofuro[2,3-b]pyridine (1.72 g, 4.85 mmol), 2-ethoxyethanol (40 mL) and DMF (40 mL) was heated at 130° C. overnight. The reaction mixture was concentrated to remove solvents and filtered through a small plug of silica gel and further chromatographed to give 0.69 g desired product (26% yield).

Example 18

Synthesis of Compound I-18

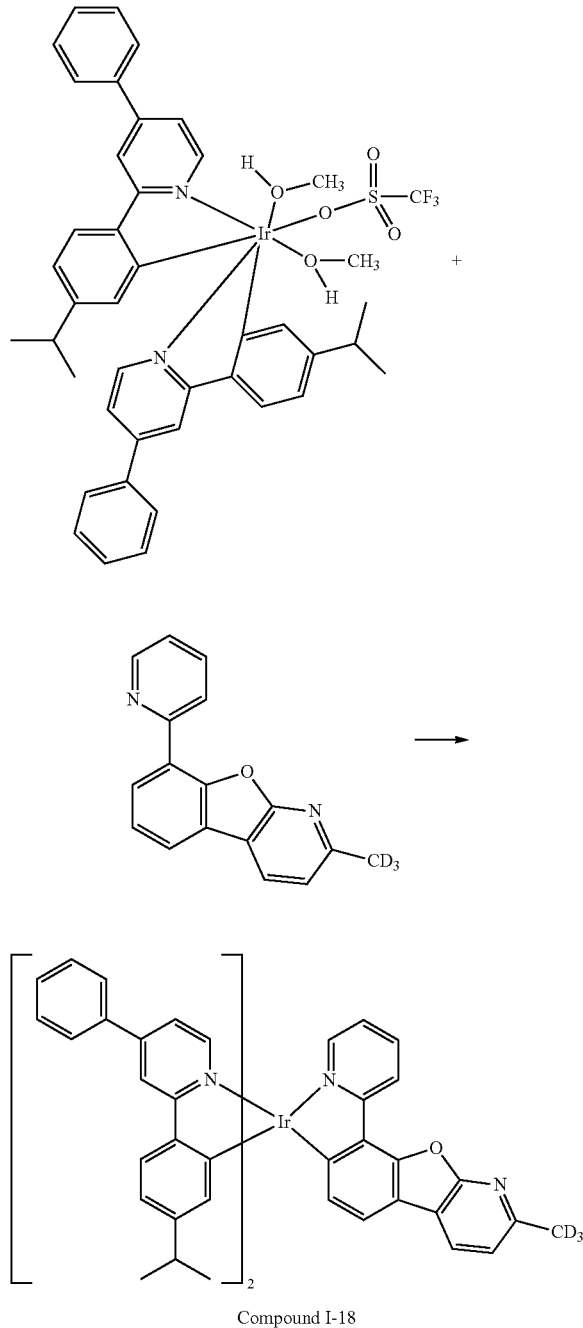

Compound I-18

A mixture of iridium precursor (1.3 g, 1.37 mmol), 2-methyl-8-(pyridin-2-yl)benzofuro[2,3-b]pyridine-d$_6$ (0.65 g, 2.46 mmol), 2-ethoxyethanol (20 mL) and DMF (20 mL) was heated at 130° C. overnight. The reaction mixture was concentrated to remove solvents and filtered through a small plug of silica gel and further chromatographed to give 0.76 g desired product (55% yield). (1.52 g, 52.2% yield) as an orange solid. LC/MS analysis confirmed the mass for the desired product.

Example 19

Synthesis of Compound I-19

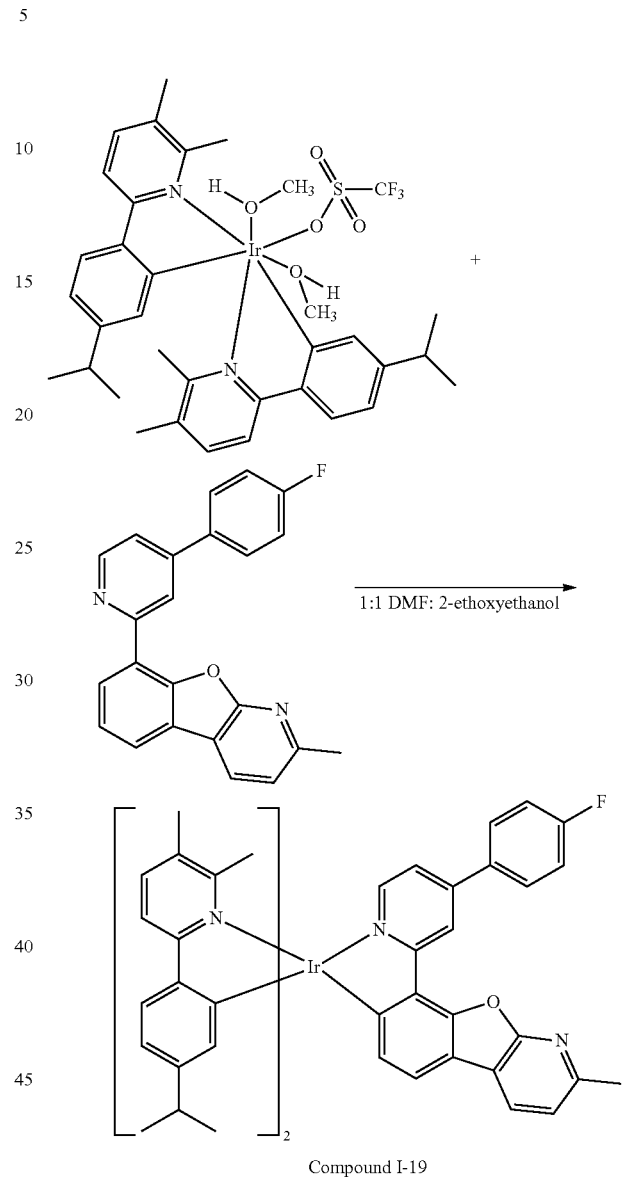

Compound I-19

The iridium precursor (2.5 g, 2.93 mmol), 8-(4-(4-fluorophenyl)pyridin-2-yl)-2-methylbenzofuro[2,3-b]pyridine (1.867 g, 5.27 mmol), DMF 25 mL and 2-ethoxyethanol 25.0 mL were combined in a 250 ml single neck round bottom flask. A condenser was attached then the system was evacuated and purged with nitrogen three times. The reaction was heated in an oil bath set at 130° C. overnight. The reaction was concentrated down to an orange sludgy solid. The solid was dissolved in 100 ml DCM and filtered through 200 g silica gel in fritted Buchner funnel with DCM. The filtrate was concentrated down to 2.3 g of an orange solid. The solid was further purified with silica gel using 25/75 to 15/85 heptane/DCM solvent system to get 0.75 g of an orange-yellow solid (25.8% yield). HPLC indicated 99.5% purity at 254 nm and LC/MS indicated it has the correct mass.

Device Examples

All example devices were fabricated by high vacuum (<10$^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of Compound B as the hole injection layer (HIL), 300 Å of 4,4% bis[N-(1-naphthyl)-N-phenylamino]biphenyl (NPD) as the hole transporting layer (HTL), 300 Å of the invention compound doped in Compound C as host with as the emissive layer (EML), 50 Å of Compound C as blocking layer 450 Å of Alq$_3$ (tris-8-hydroxyquinoline aluminum) as the ETL. Comparative Example with Compound A was fabricated similarly to the Device Examples except that the Compound A was used as the emitter in the EML.

The device results and data are summarized in Tables 1 and 2 from those devices. As used herein, NPD, Alq, Compound A, Compound B, and Compound C have the following structures:

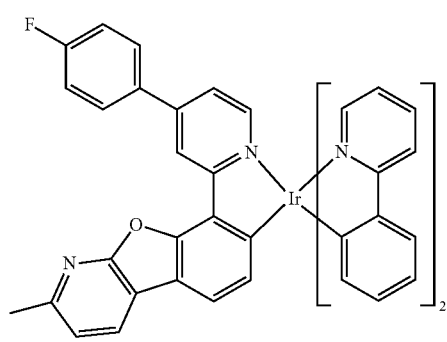

Compound A

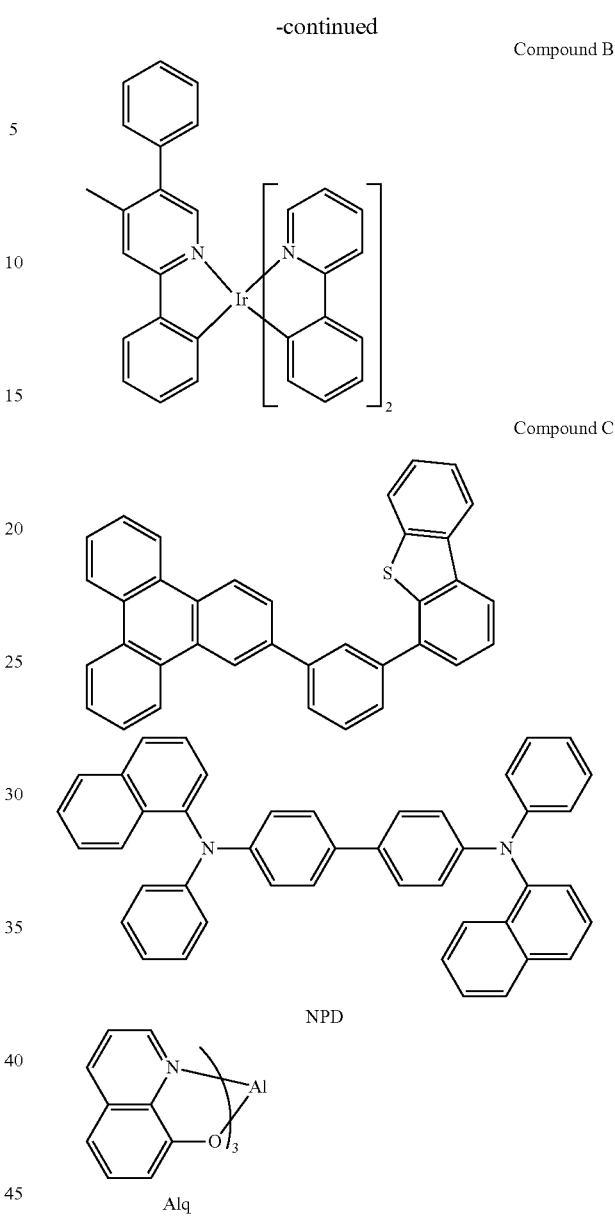

Compound B

Compound C

NPD

Alq

TABLE 2

DEVICE EXAMPLES

| DEVICE EXAMPLE | HIL | HTL | EML (300 Å, doping %) | | BL | ETL |
|---|---|---|---|---|---|---|
| Comparative Example 1 | Compound B 100 Å | NPD 300 Å | Compound C | Compound A 7% | Compound C 50 Å | Alq 450 Å |
| Inventive Example 1 | Compound B 100 Å | NPD 300 Å | Compound C | Compound I-2 7% | Compound C 50 Å | Alq 450 Å |
| Inventive Example 2 | Compound B 100 Å | NPD 300 Å | Compound C | Compound I-4 7% | Compound C 50 Å | Alq 450 Å |

TABLE 3

VACUUM THERMAL EVAPORATION

| Example | CIE x | CIE y | λ max [nm] | FWHM [nm] | EQE |
|---|---|---|---|---|---|
| Comparative Example 1 | 0.42 | 0.57 | 548 | 71 | 20.9 |
| Inventive Example 1 | 0.45 | 0.55 | 555 | 74 | 24.7 |
| Inventive Example 2 | 0.45 | 0.55 | 554 | 74 | 22.3 |

Table 3 summarizes the performance of the devices. External quantum efficiency (EQE) was measured at 1000 nits. As shown in Table 3 the device prepared using Compound I-2 and Compound I-4 of the present invention showed similar color to the device prepared using comparative Compound A. However, the EQE of the devices with Compound I-2 and Compound I-4 was much higher than the device with comparative Compound A. Therefore, devices prepared with compounds containing an alkyl group at the 4-position of the phenyl ring in the phenylpyridine showed much higher EQEs than a compound that contained a hydrogen at this position.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art it is understood that various theories as to why the invention works are not intended to be limiting.

What is claimed is:

1. A compound having the formula

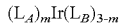

(I);

wherein $L_A$ is

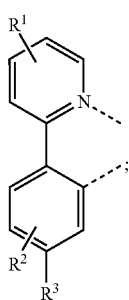

(II)

wherein $L_B$ is

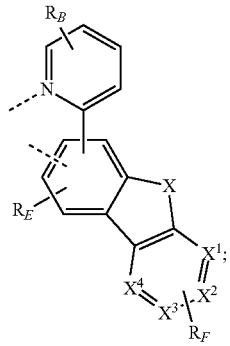

(V)

wherein $R_E$ represents mono or di-substitution, or no substitution;

wherein $R^2$ represents mono, di, or tri-substitution, or no substitution;

wherein $R^1$, $R_B$, and $R_F$ are each independently mono, di, tri, or tetra-substitution, or no substitution;

wherein $X^1$, $X^2$, $X^3$, and $X^4$ are each independently CH or nitrogen, wherein the H in CH can be substituted by $R_F$;

wherein X is selected from the group consisting of O, S, and Se;

wherein $R^1$, $R^2$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxyl, alkoxycarbonyl, cycloalkoxycarbonyl, heteroalkyloxycarbonyl, arylalkyloxycarbonyl, alkenyloxycarbonyl, cycloalkenyloxycarbonyl, heteroalkenyloxycarbonyl, alkynyloxycarbonyl, aryloxycarbonyl, heteroaryloxycarbonyl, cyano, carbylamino, sulfanyl, sulfinyl, sulfonyl, phosphino, and combinations thereof;

wherein $R^3$ is selected from the group consisting of alkyl, cycloalkyl, and combinations thereof;

wherein $R^3$ is optionally partially or fully deuterated; and wherein m is 1 or 2.

2. The compound of claim 1, wherein m is 2.

3. The compound of claim 1, wherein X is O.

4. The compound of claim 1, wherein $R^3$ is an alkyl having at least 2 carbons.

5. The compound of claim 1, wherein $R^3$ is an alkyl having at least 3 carbons.

6. The compound of claim 1, wherein $R^3$ is a cycloalkyl.

7. The compound of claim 1, wherein $R^3$ is selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, and cyclohexyl, wherein each is optionally partially or fully deuterated.

8. The compound of claim 1, wherein $R^1$ is selected from the group consisting of hydrogen, deuterium, alkyl, cycloalkyl, and combinations thereof.

9. The compound of claim 1, wherein $R^2$ represents no substitution.

10. The compound of claim 1, wherein $R_F$ is selected from the group consisting of hydrogen, deuterium, alkyl, cycloalkyl, halogen, and combinations thereof.

11. The compound of claim 1, wherein $R_F$ is fluorine.

12. The compound of claim 1, wherein $R_E$ represents no substitution.

13. The compound of claim 1, wherein $L_B$ is selected from the group consisting of:

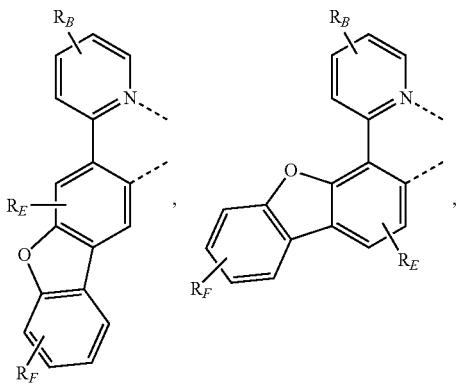

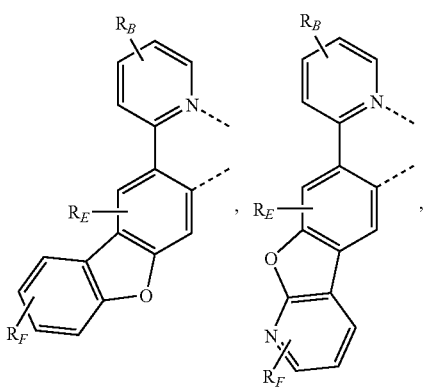

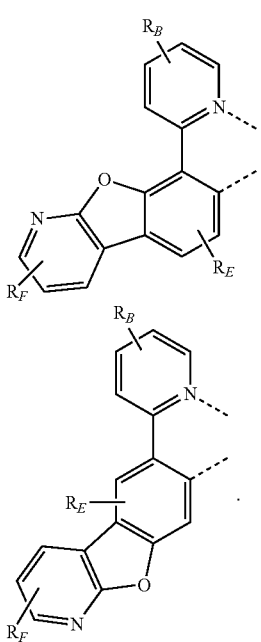

14. The compound of claim 1, wherein $L_B$ is:

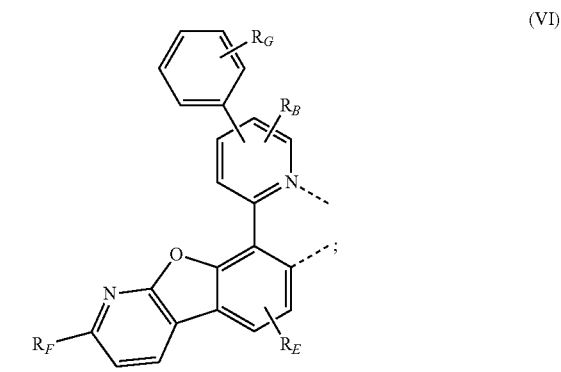

(VI)

wherein $R_G$ represents mono, di, tri, or tetra-substitution, or no substitution; and wherein $R_G$ is selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxyl, alkoxycarbonyl, cycloalkoxycarbonyl, heteroalkyloxycarbonyl, arylalkyloxycarbonyl, alkenyloxycarbonyl, cycloalkenyloxycarbonyl, heteroalkenyloxycarbonyl, alkynyloxycarbonyl, aryloxycarbonyl, heteroaryloxycarbonyl, cyano, carbylamino, sulfanyl, sulfinyl, sulfonyl, phosphino, and combinations thereof.

15. The compound of claim 14, wherein $R_B$ and $R_E$ represent no substitution; and wherein $R_F$ and $R_G$ are each independently selected from the group consisting of hydrogen, deuterium, alkyl, cycloalkyl, halogen, and combinations thereof.

16. The compound of claim 15, wherein $R_G$ is fluorine.

17. The compound of claim 1, wherein $L_A$ is selected from the group consisting of:

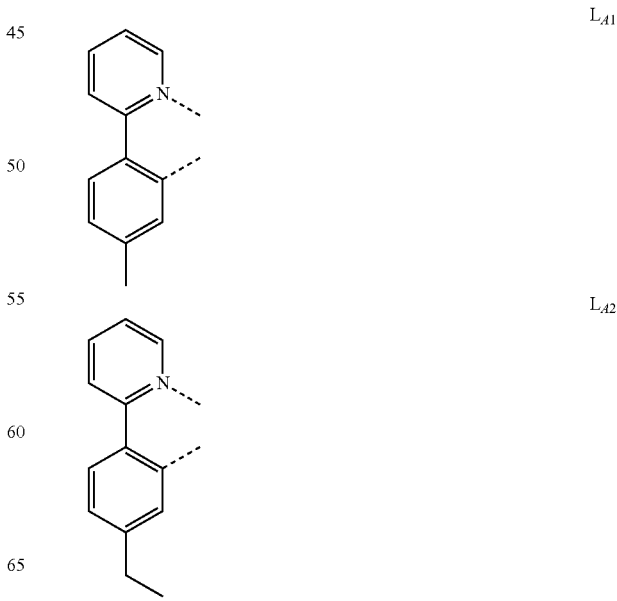

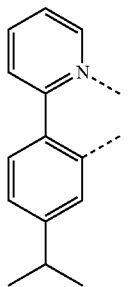
L_{A3}
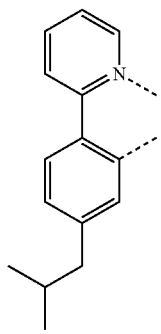
L_{A4}
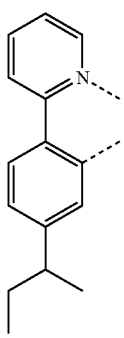
L_{A5}
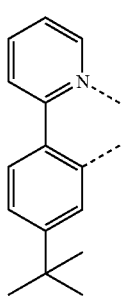
L_{A6}
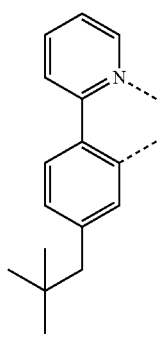
L_{A7}
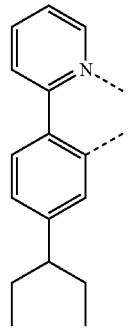
L_{A8}
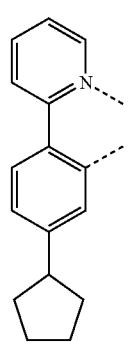
L_{A9}
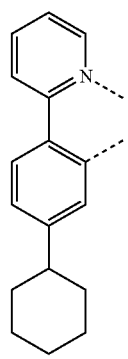
L_{A10}
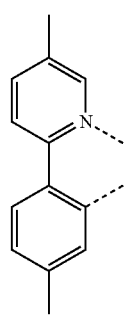
L_{A11}

-continued
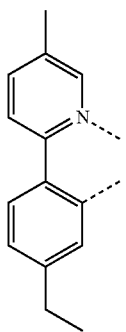
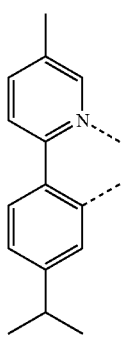
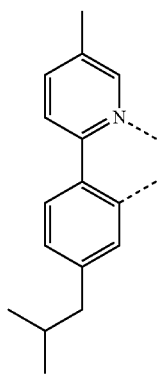
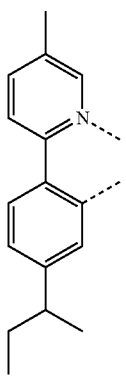
-continued
L_{A12}
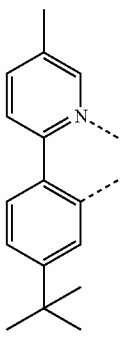
L_{A13}
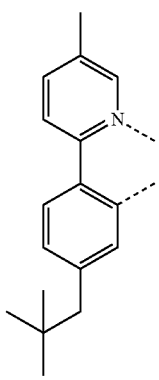
L_{A14}
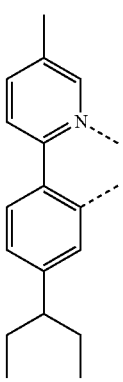
L_{A15}
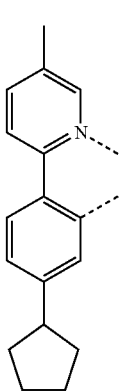
L_{A16}
L_{A17}
L_{A18}
L_{A19}

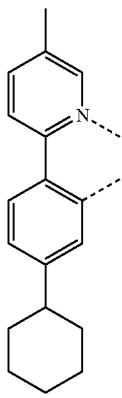
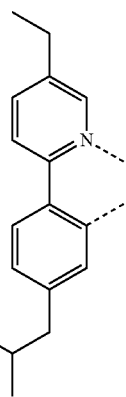
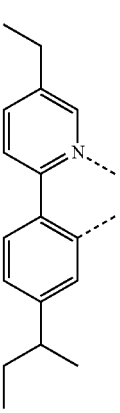
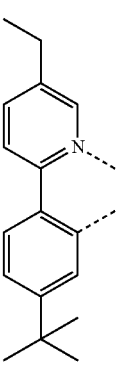
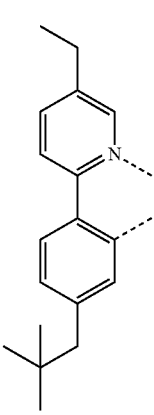

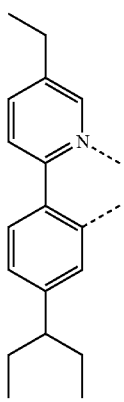
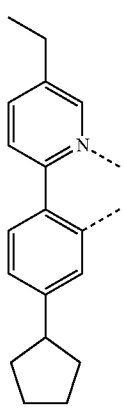
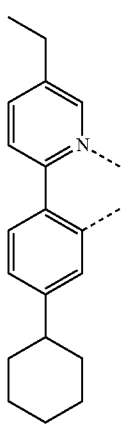
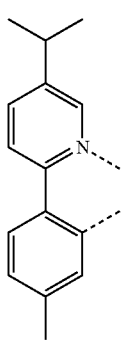
$L_{A28}$
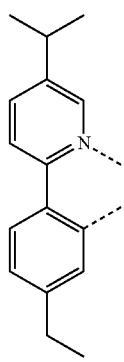
$L_{A29}$
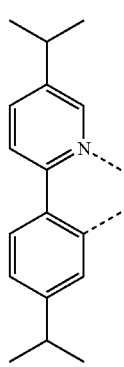
$L_{A30}$
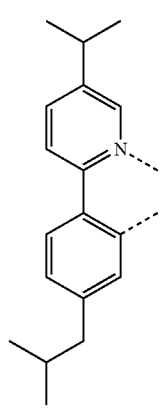
$L_{A31}$
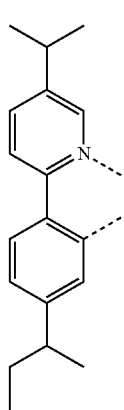
$L_{A32}$
$L_{A33}$
$L_{A34}$
$L_{A35}$ 255
-continued
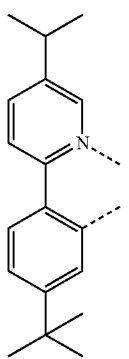
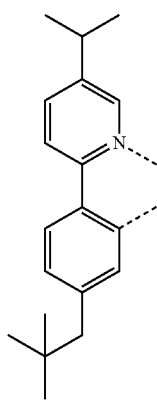
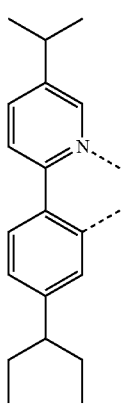
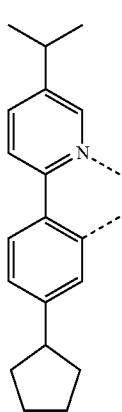
256
-continued
L<sub>A36</sub>
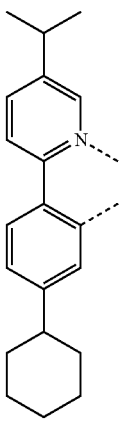
L<sub>A37</sub>
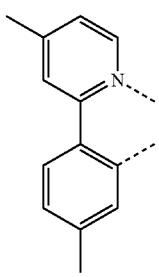
L<sub>A38</sub>
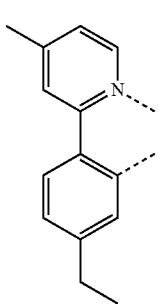
L<sub>A39</sub>
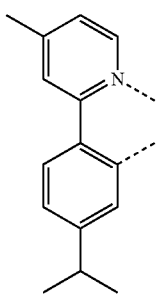
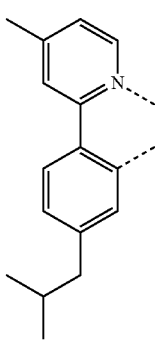
L<sub>A40</sub>
L<sub>A41</sub>
L<sub>A42</sub>
L<sub>A43</sub>
L<sub>A44</sub>

257
-continued
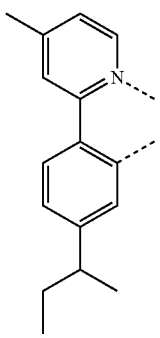
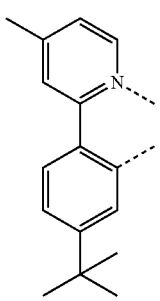
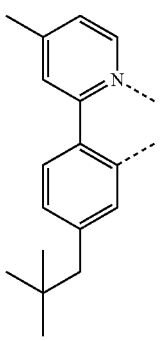
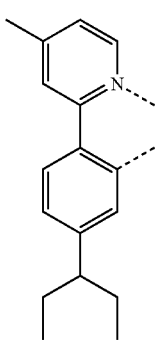
258
-continued
L_{A45}
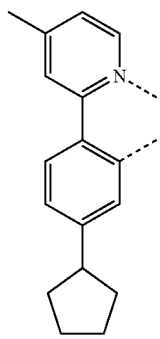
L_{A46}
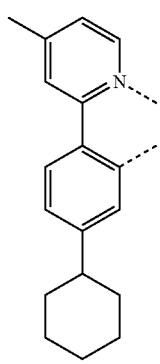
L_{A47}
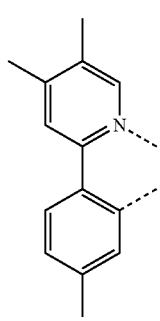
L_{A48}
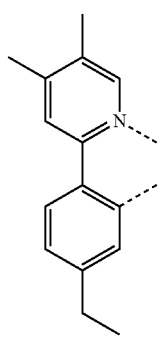
L_{A49}
L_{A50}
L_{A51}
L_{A52}

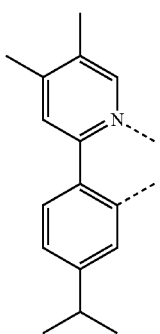
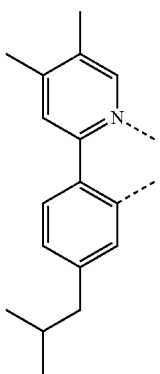
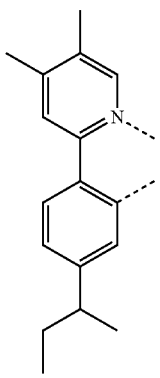
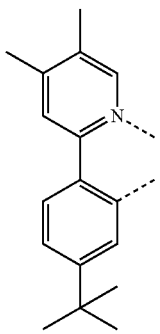
L_{A53}
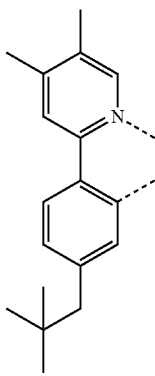
L_{A54}
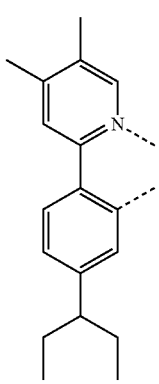
L_{A55}
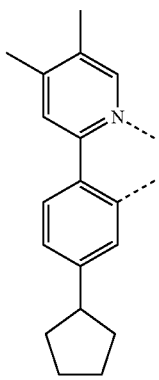
L_{A56}
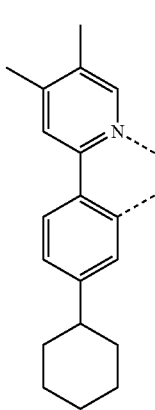
L_{A57}
L_{A58}
L_{A59}
L_{A60}

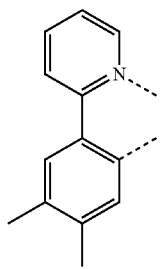
L_{A61}
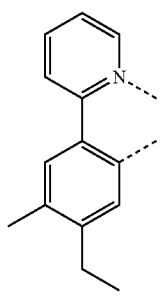
L_{A62}
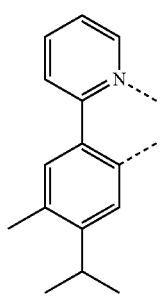
L_{A63}
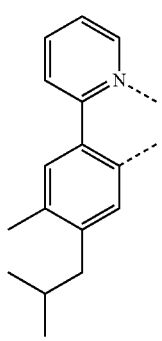
L_{A64}
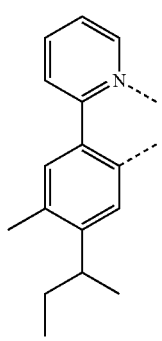
L_{A65}
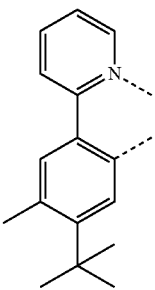
L_{A66}
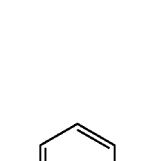
L_{A67}
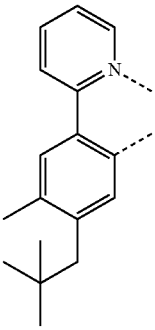
L_{A68}
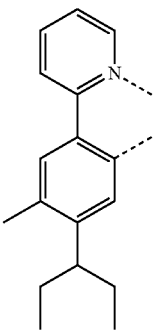
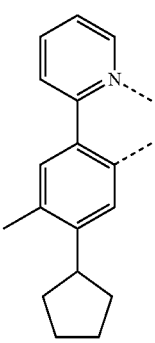
L_{A69}

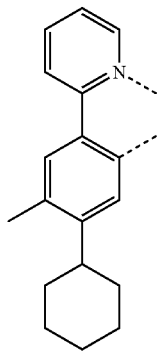
L_A69
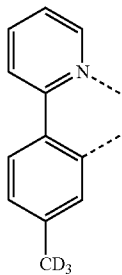
L_A70
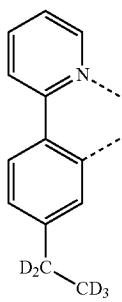
L_A71
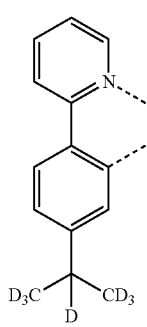
L_A72
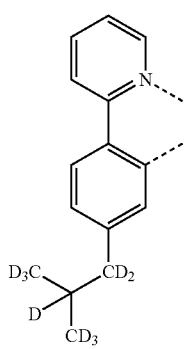
L_A73
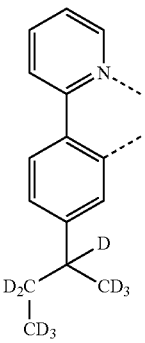
L_A74
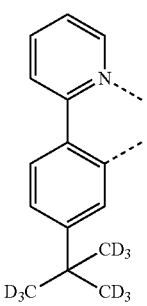
L_A75
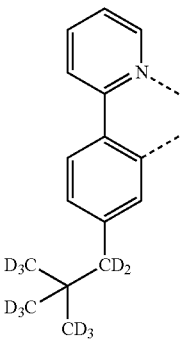
L_A76
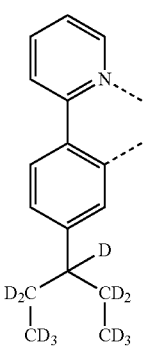
L_A77
L_A78

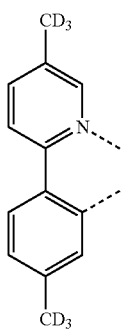
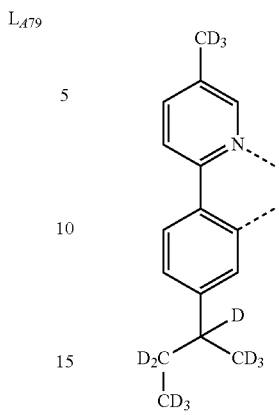
18. The compound of claim 1, wherein $L_A$ is selected from the group consisting of:

L<sub>A87</sub> 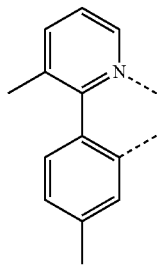
L<sub>A88</sub> 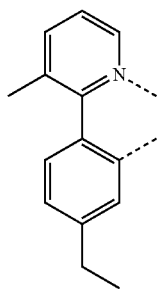
L<sub>A89</sub> 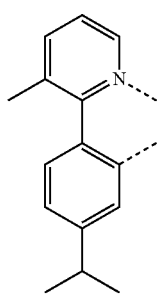
L<sub>A90</sub> 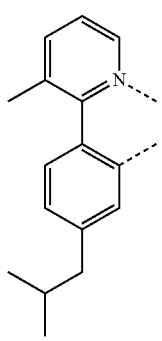
L<sub>A91</sub> 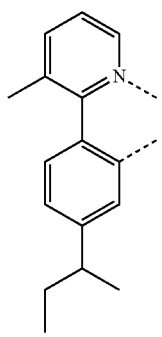
L<sub>A92</sub> 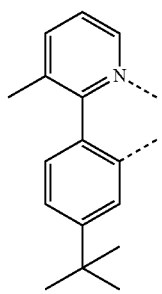
L<sub>A93</sub> 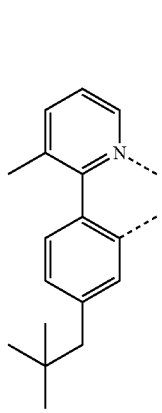
L<sub>A94</sub> 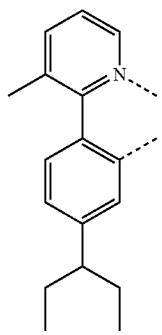
L<sub>A95</sub> 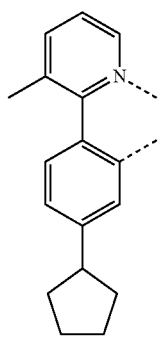

-continued
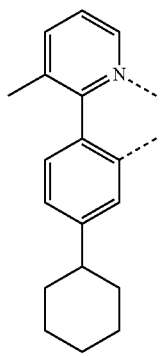
L_{A96}
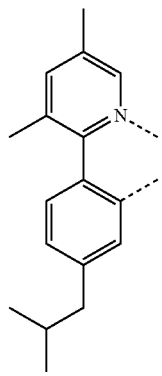
L_{A100}
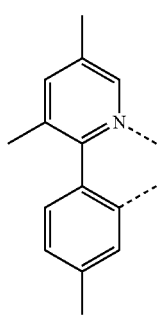
L_{A97}
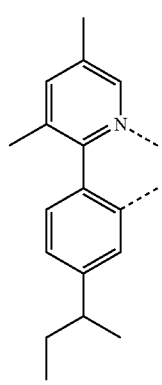
L_{A101}
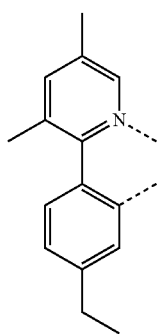
L_{A98}
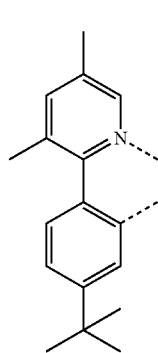
L_{A102}
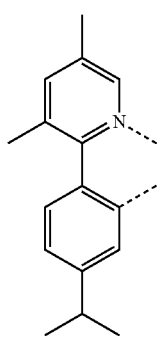
L_{A99}
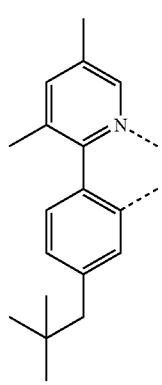
L_{A103}

-continued
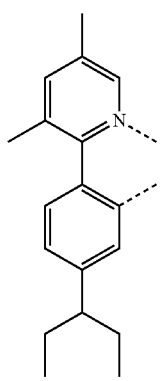
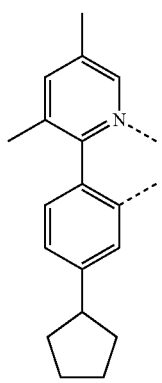
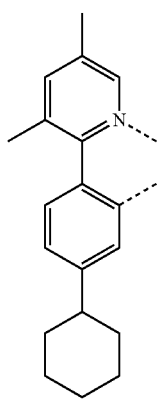
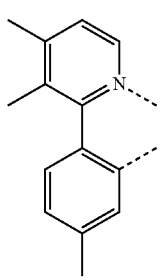
-continued
L_{A104}
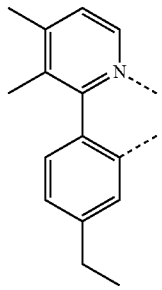
L_{A105}
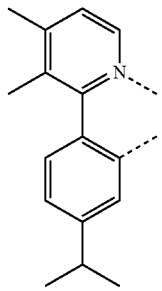
L_{A106}
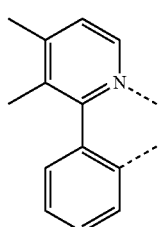
L_{A107}
L_{A108}
L_{A109}
L_{A110}
L_{A111}
L_{A112}

-continued
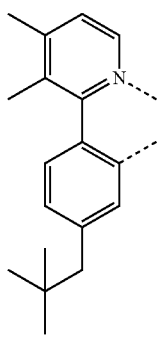
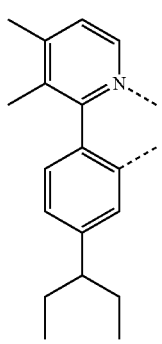
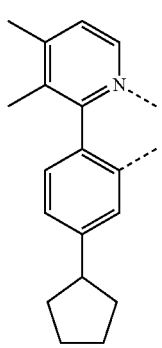
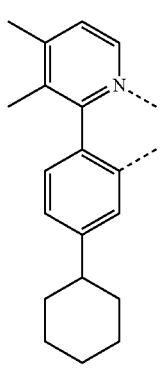
-continued
L$_{A113}$
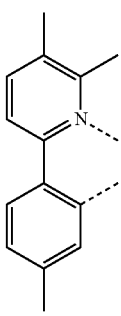
L$_{A114}$
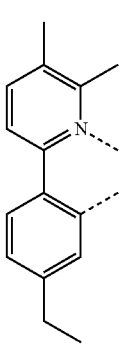
L$_{A115}$
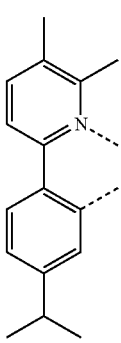
L$_{A116}$
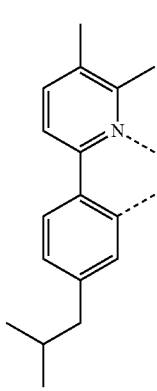
L$_{A117}$
L$_{A118}$
L$_{A119}$
L$_{A120}$ L_{A121}
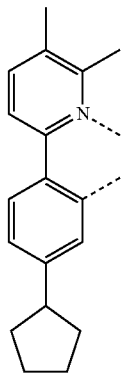
L_{A125}
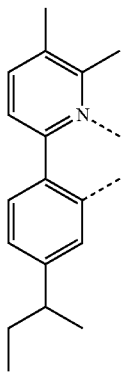
L_{A122}
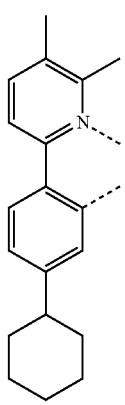
L_{A126}
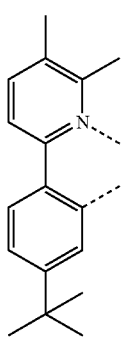
L_{A123}
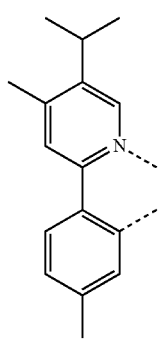
L_{A127}
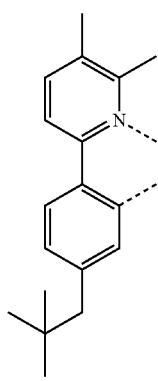
L_{A124}
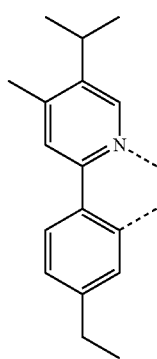
L_{A128}
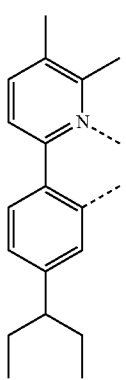

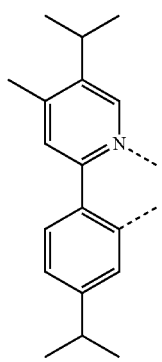
L<sub>A129</sub>
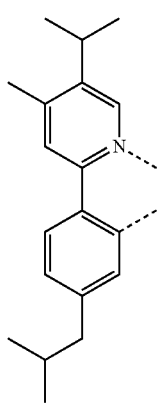
L<sub>A130</sub>
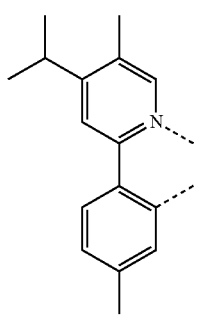
L<sub>A131</sub>
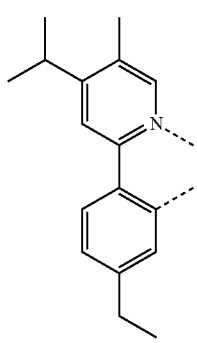
L<sub>A132</sub>
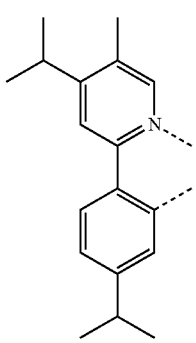
L<sub>A133</sub>

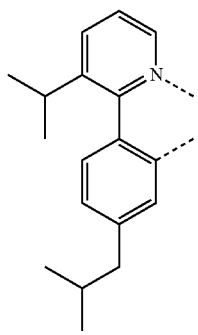
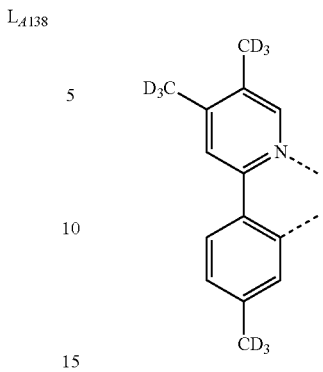
L_{A138}
L_{A139}
L_{A140}
L_{A141}
L_{A142}
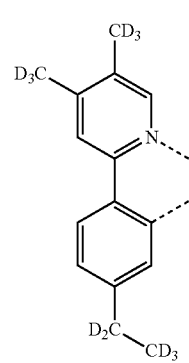
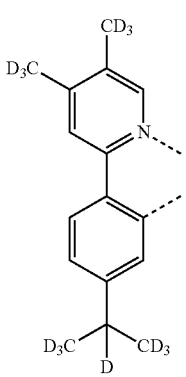
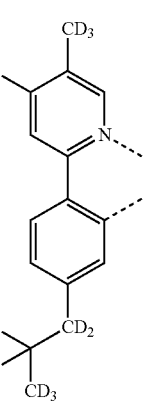
L_{A143}
L_{A144}
L_{A145}
L_{A146}

L<sub>A</sub>147 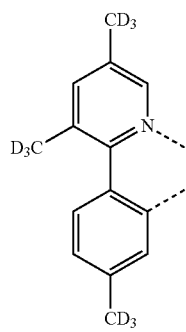
L<sub>A</sub>148 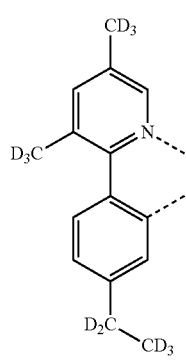
L<sub>A</sub>149 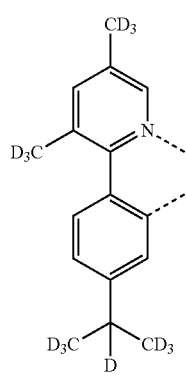
L<sub>A</sub>150 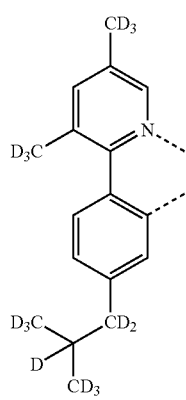
L<sub>A</sub>151 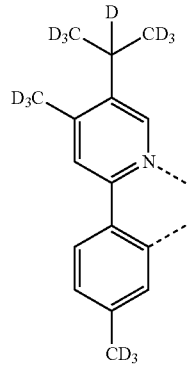
L<sub>A</sub>152 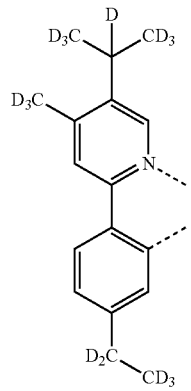
L<sub>A</sub>153 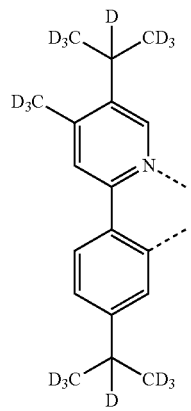
L<sub>A</sub>154 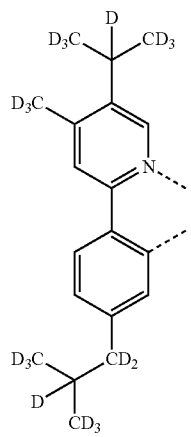

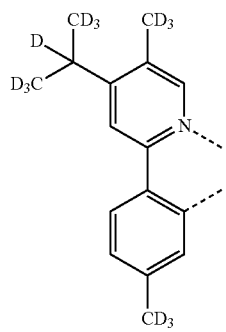
L<sub>A155</sub>
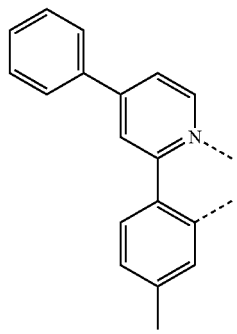
L<sub>A159</sub>
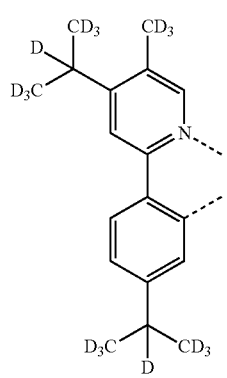
L<sub>A156</sub>
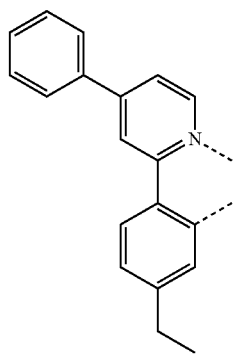
L<sub>A160</sub>
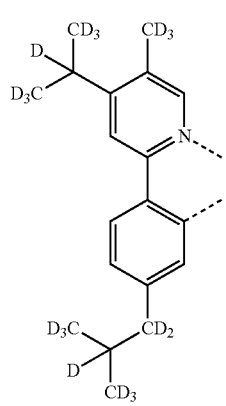
L<sub>A157</sub>
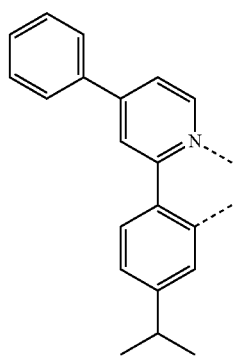
L<sub>A161</sub>
L<sub>A158</sub>
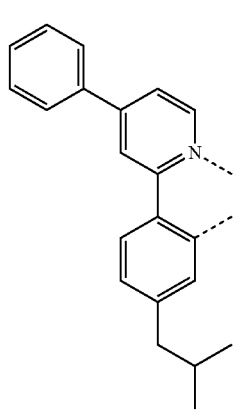
L<sub>A162</sub>

285
-continued
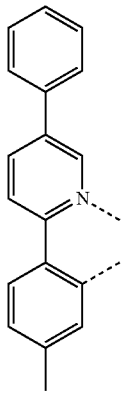
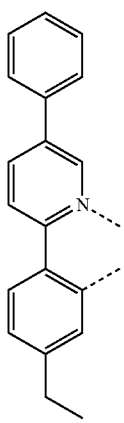
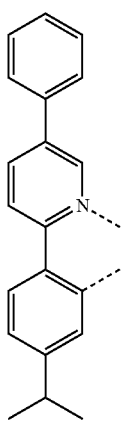
286
-continued
L$_{A163}$
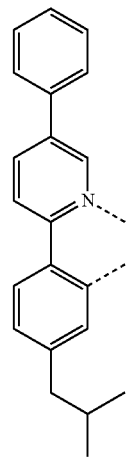
L$_{A64}$
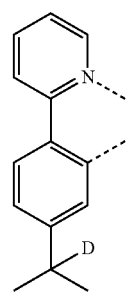
L$_{A165}$
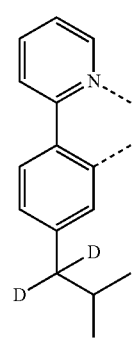
L$_{A166}$
L$_{A167}$
L$_{A168}$
L$_{A169}$
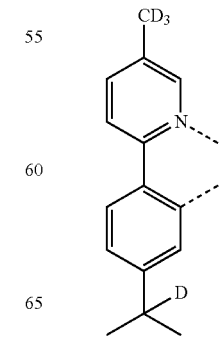

19. The compound of claim 1, wherein $L_B$ is selected from the group consisting of:

L$_{B46}$ 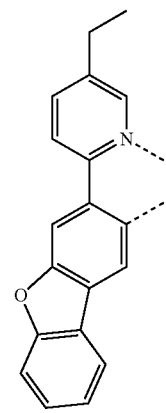
L$_{B47}$ 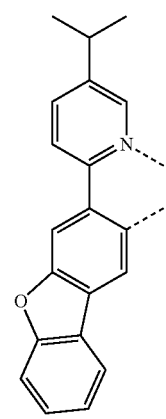
L$_{B48}$ 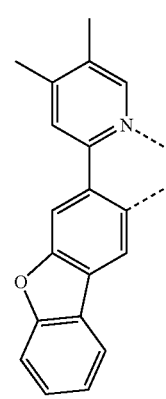
L$_{B49}$ 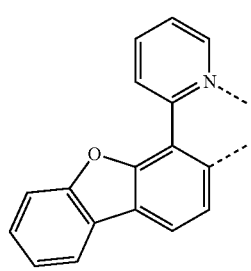
L$_{B50}$ 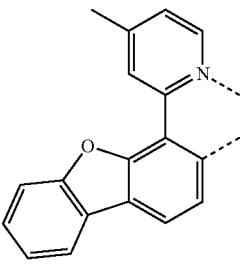
L$_{B51}$ 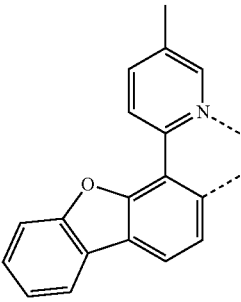
L$_{B52}$ 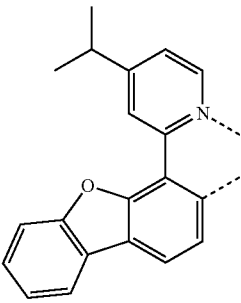
L$_{B53}$ 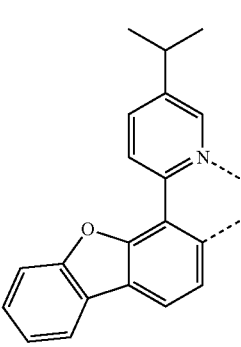
L$_{B54}$ 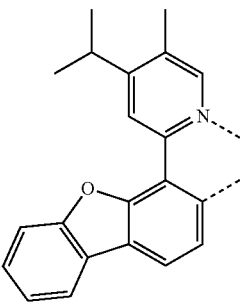

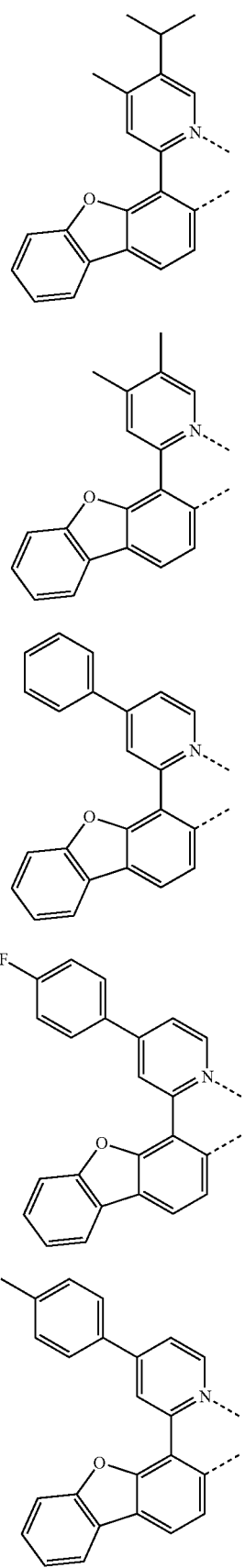
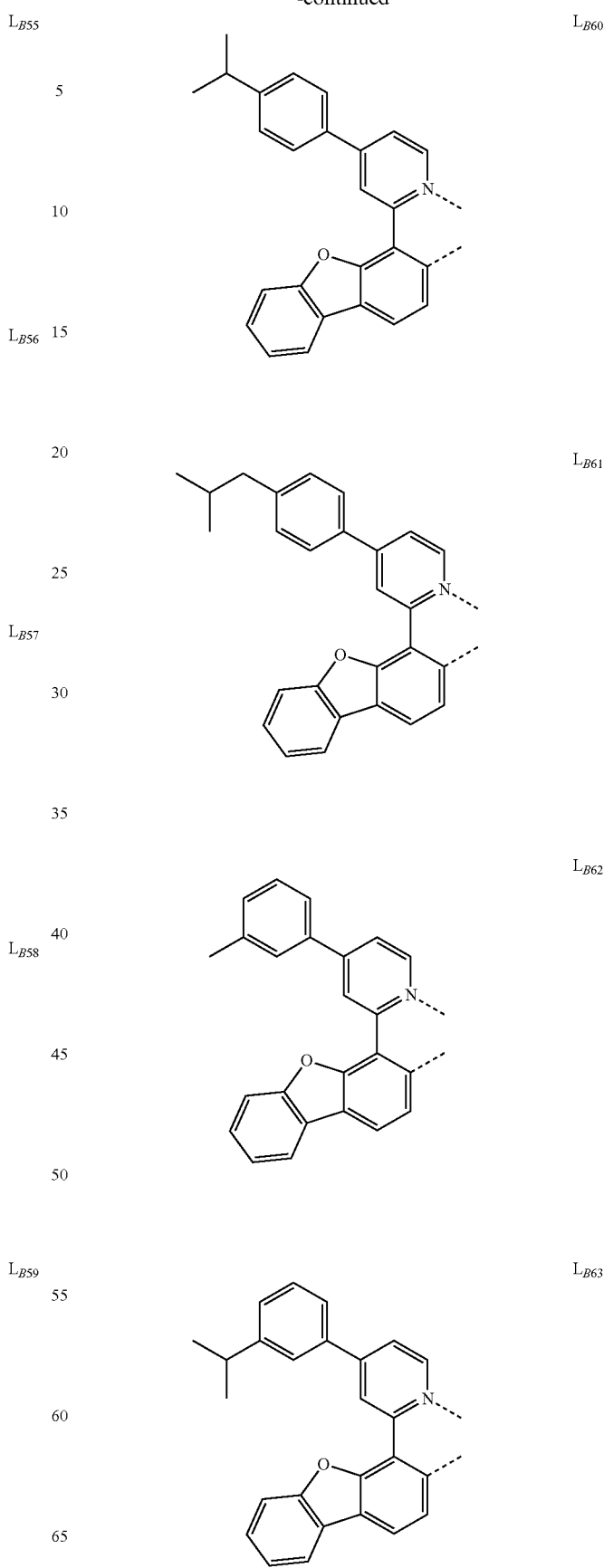

L_{B64}

L_{B65}

L_{B66}

L_{B67}

L_{B68}

L_{B69}

L_{B70}

L_{B71}
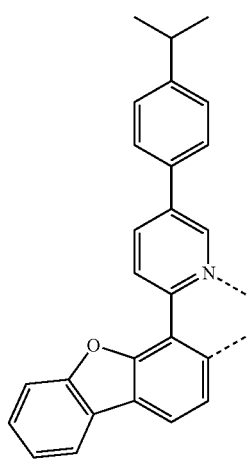
L_{B72}
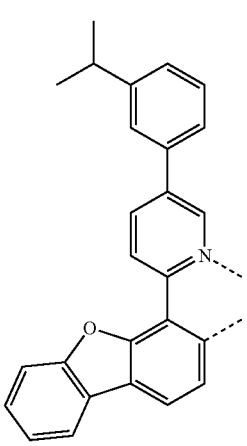
L_{B73}
L_{B74}
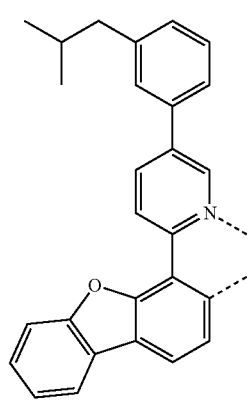
L_{B75}
L_{B76}
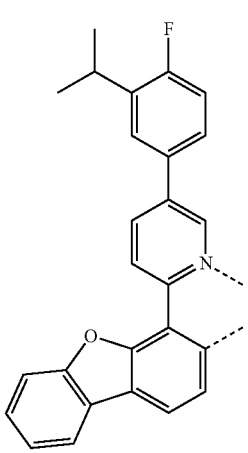

-continued
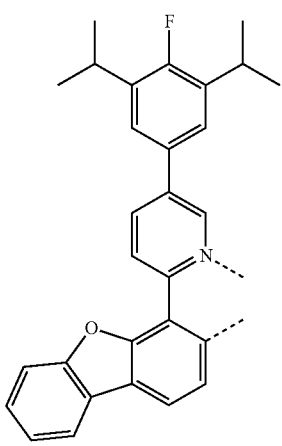
L_{B77}
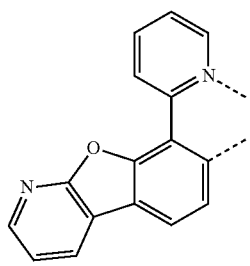
L_{B78}
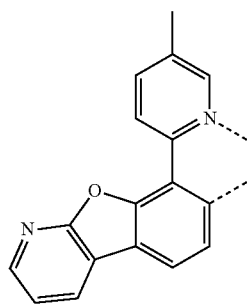
L_{B79}
L_{B80}
-continued
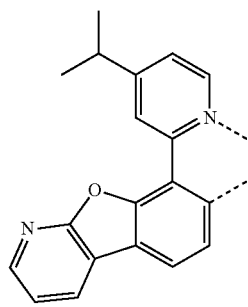
L_{B81}
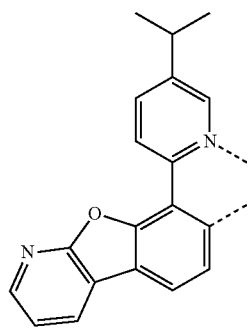
L_{B82}
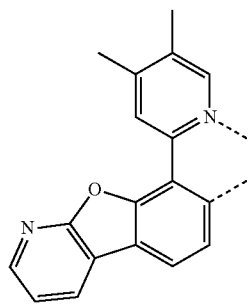
L_{B83}
L_{B84}
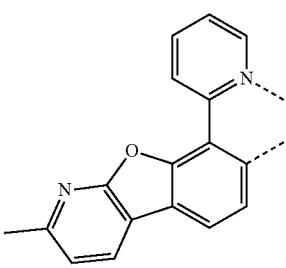
L_{B85}

| | |
|---|---|
| 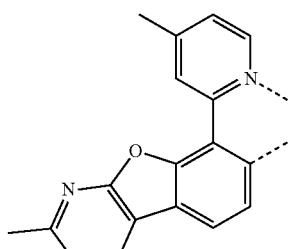 | $L_{B86}$ |
| 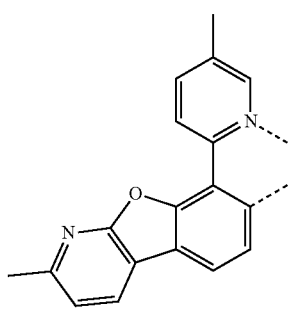 | $L_{B87}$ |
| 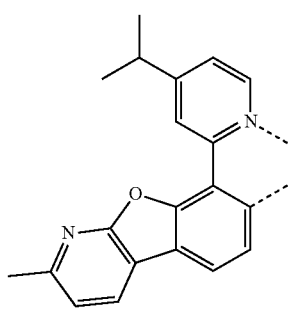 | $L_{B88}$ |
| 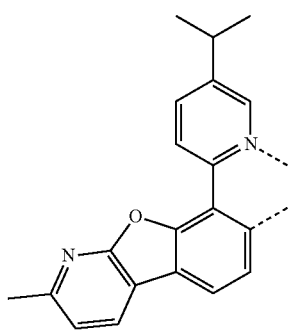 | $L_{B89}$ |
| 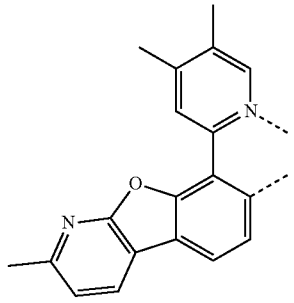 | $L_{B90}$ |
| | |
|---|---|
| 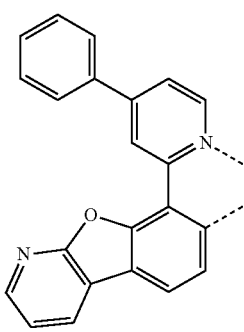 | $L_{B91}$ |
| 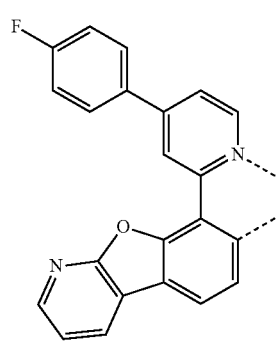 | $L_{B92}$ |
| 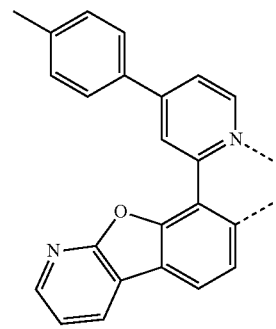 | $L_{B93}$ |
| 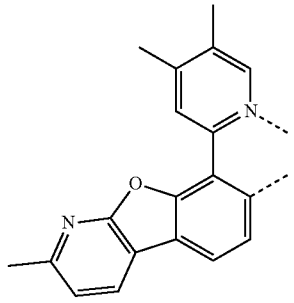 | $L_{B94}$ |

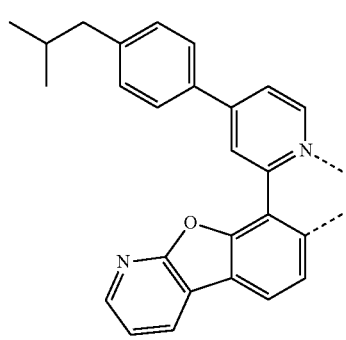 L$_{B95}$
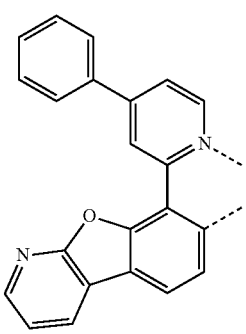 L$_{B96}$
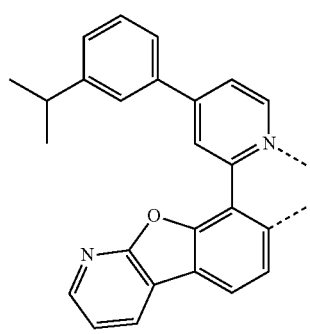 L$_{B97}$
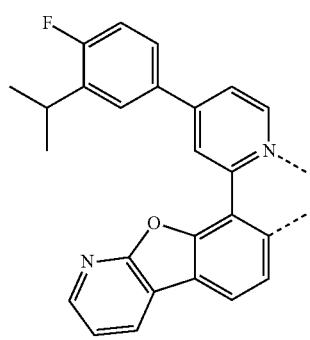 L$_{B98}$
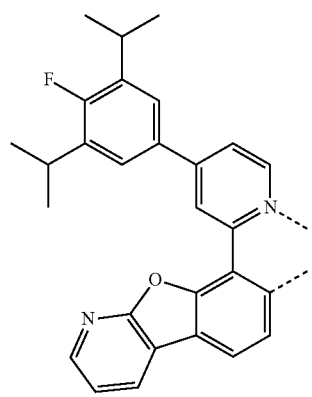 L$_{B99}$
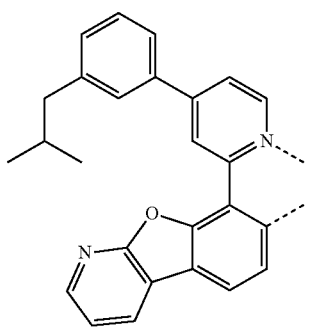 L$_{B100}$
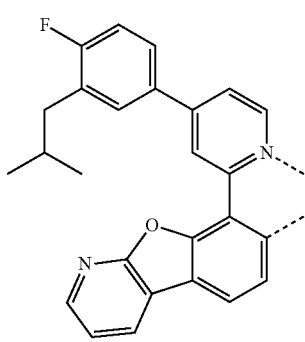 L$_{B101}$
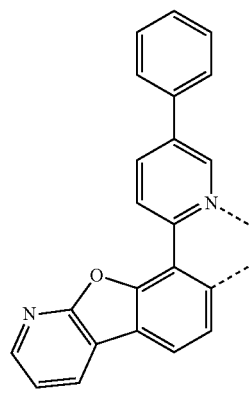 L$_{B102}$ -continued
L_{B103}
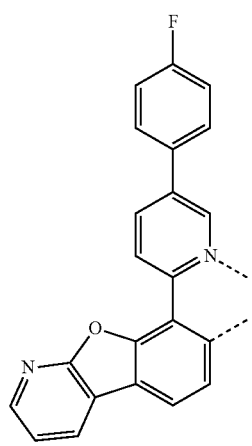
L_{B104}
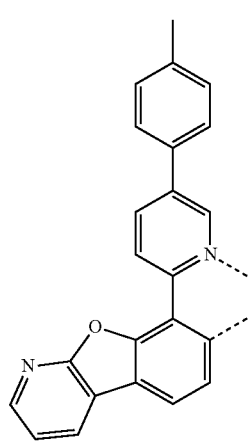
L_{B105}
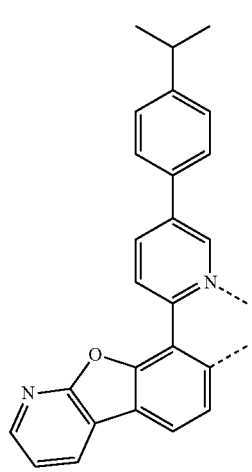
L_{B106}
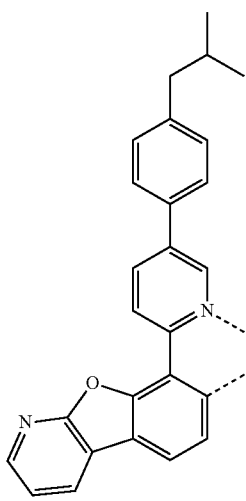
L_{B107}
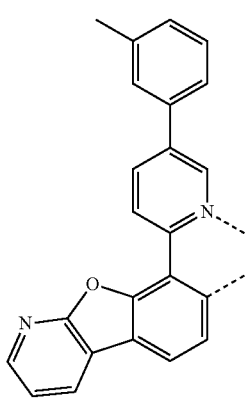
L_{B108}
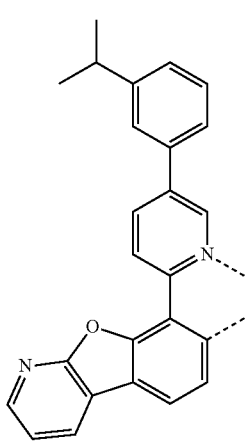

| | |
|---|---|
| 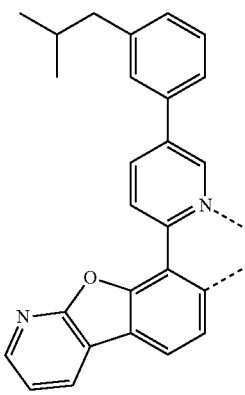 L<sub>B109</sub> | 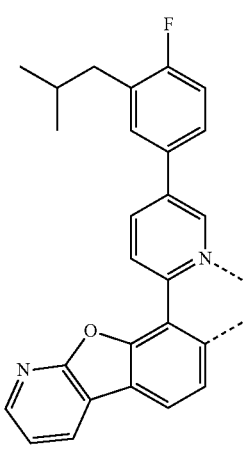 L$_{B112}$ |
| 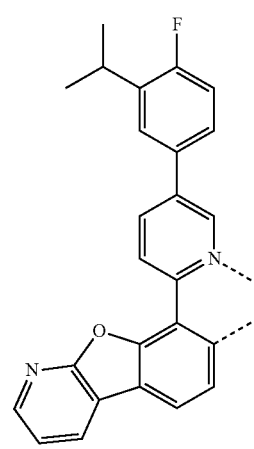 L$_{B110}$ | 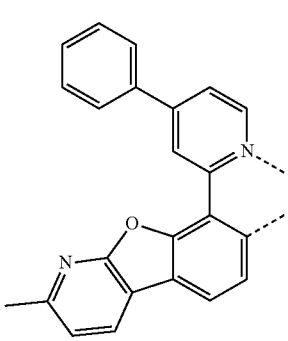 L$_{B113}$ |
| | 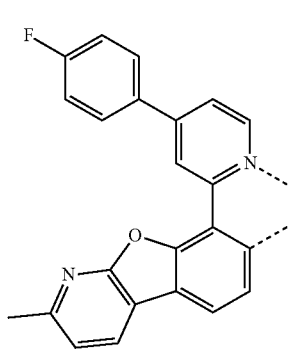 L$_{B114}$ |
| 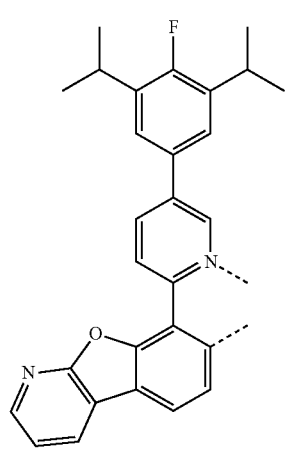 L$_{B111}$ | 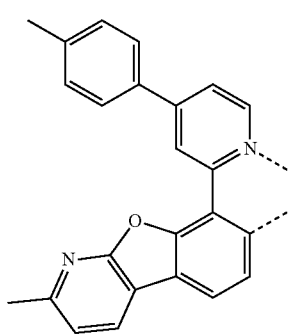 L$_{B115}$ |

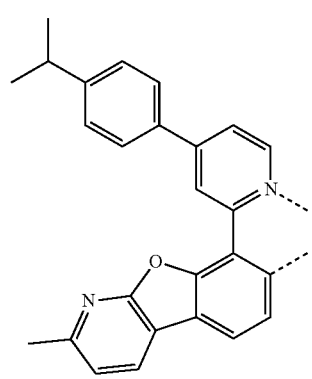 L_B116
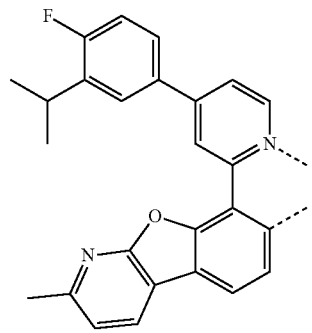 L_B120
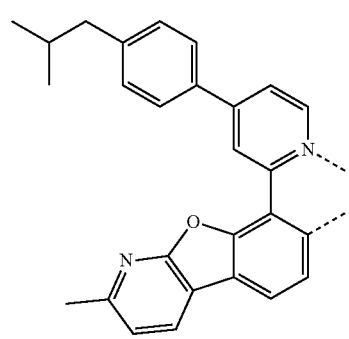 L_B117
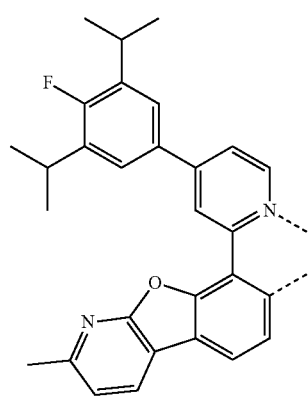 L_B121
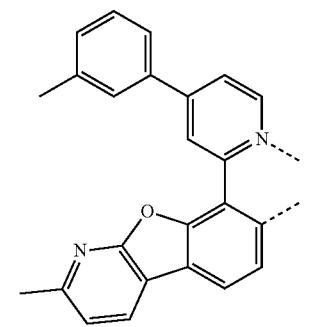 L_B118
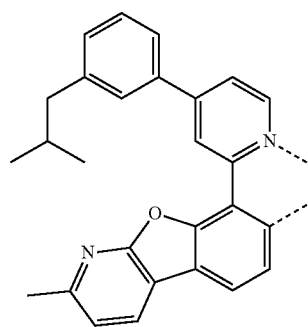 L_B122
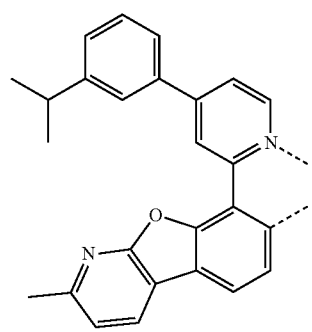 L_B119
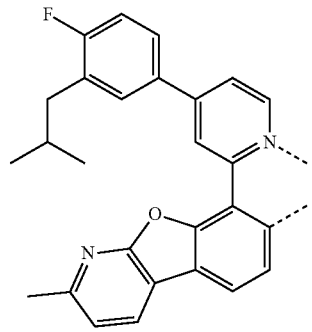 L_B123

309
-continued
L<sub>B124</sub>
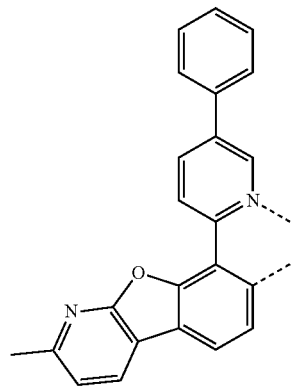
L<sub>B125</sub>
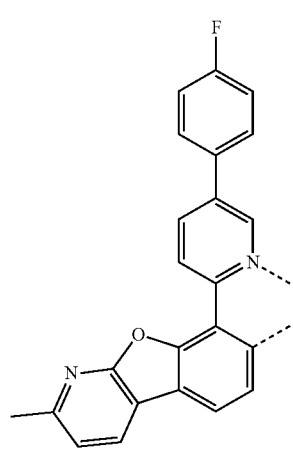
L<sub>B126</sub>
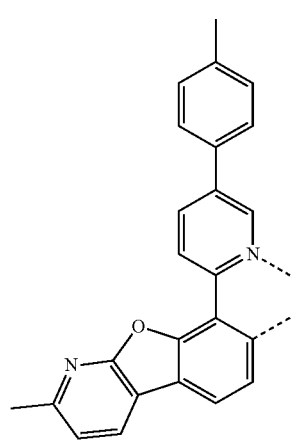
310
-continued
L<sub>B127</sub>
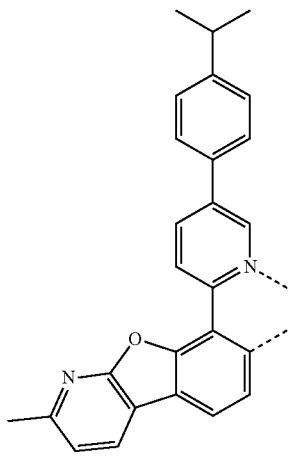
L<sub>B128</sub>
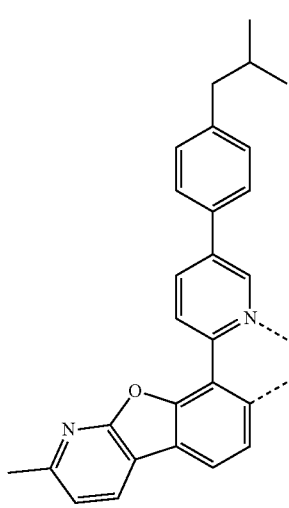
L<sub>B129</sub>
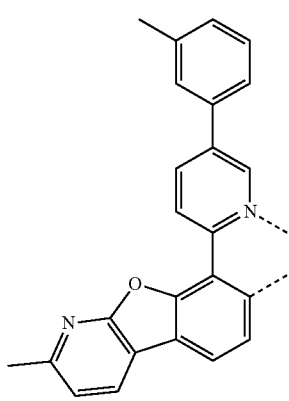

-continued
L<sub>B130</sub>
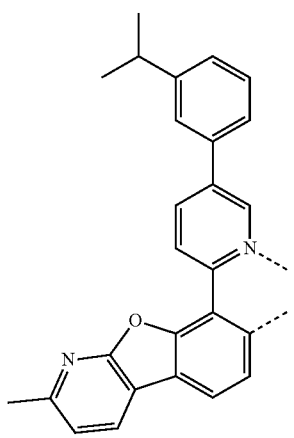
L<sub>B131</sub>
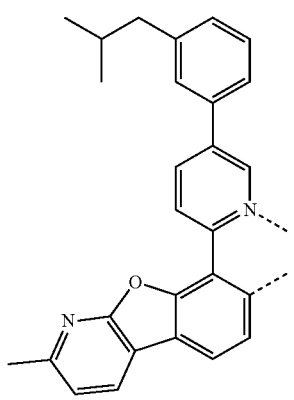
L<sub>B132</sub>
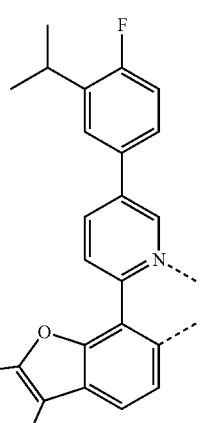
L<sub>B133</sub>
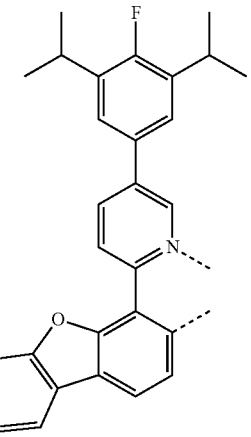
L<sub>B134</sub>
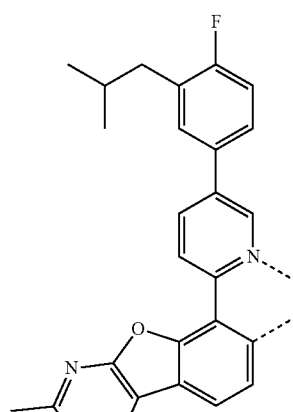
L<sub>B175</sub>
L<sub>B176</sub>
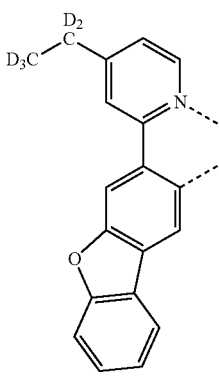

313
-continued
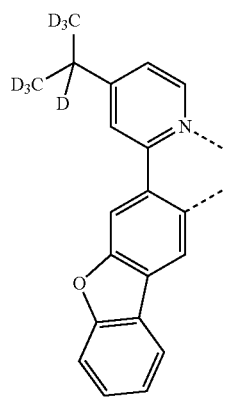  L<sub>B177</sub>
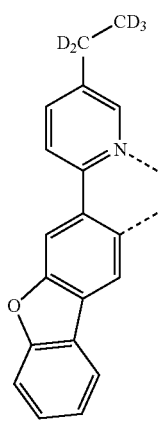  L<sub>B178</sub>
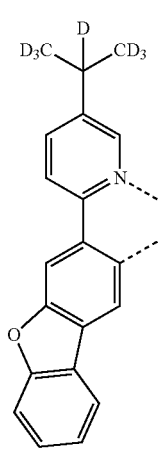  L<sub>B179</sub>
L<sub>B180</sub>
314
-continued
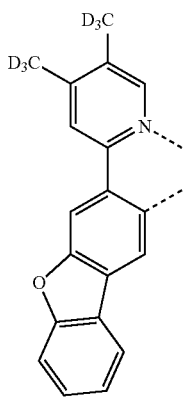  L<sub>B181</sub>
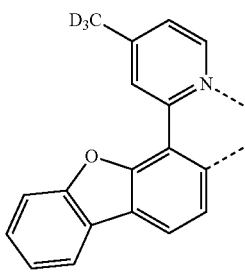  L<sub>B182</sub>
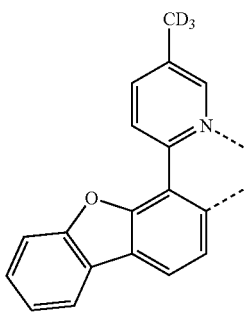  L<sub>B183</sub>
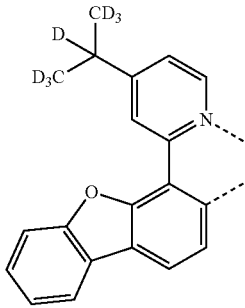  L<sub>B184</sub>

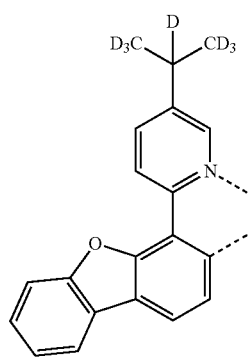
L<sub>B185</sub>
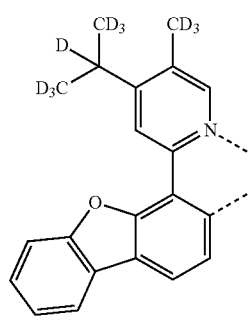
L<sub>B186</sub>
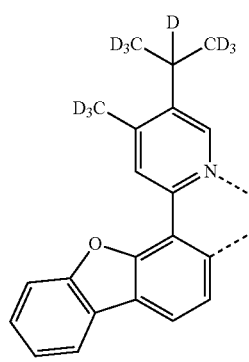
L<sub>B187</sub>
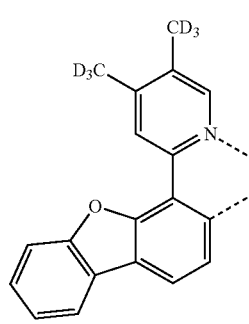
L<sub>B188</sub>
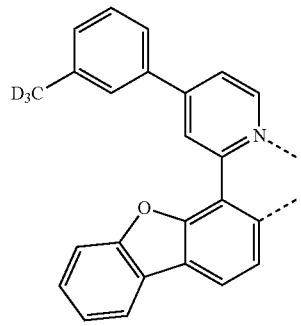
L<sub>B189</sub>
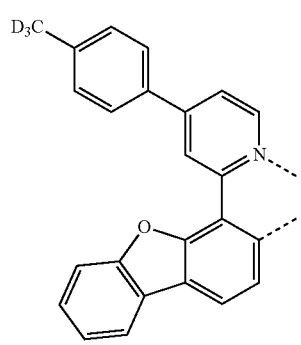
L<sub>B190</sub>
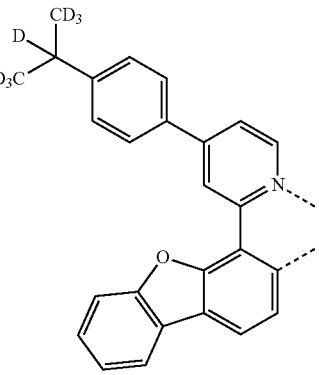
L<sub>B191</sub>
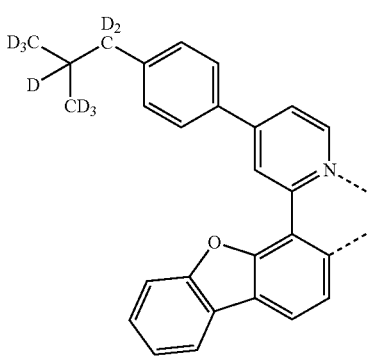
L<sub>B192</sub>

| | |
|---|---|
| L_{B193} 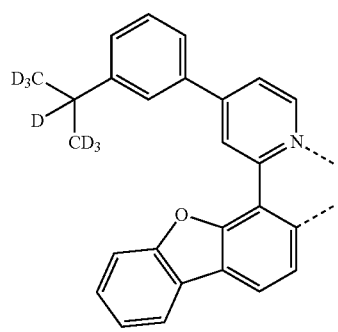 | L_{B197} 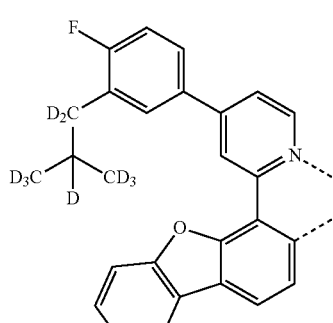 |
| L_{B194} | L_{B198} |
| L_{B195} | |
| L_{B196} | L_{B199} |

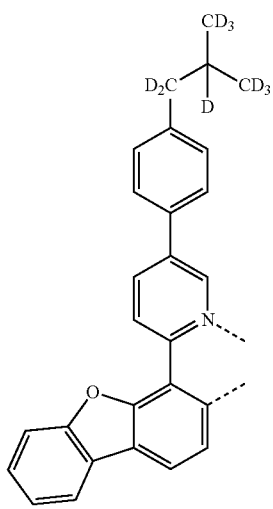 L_{B200}
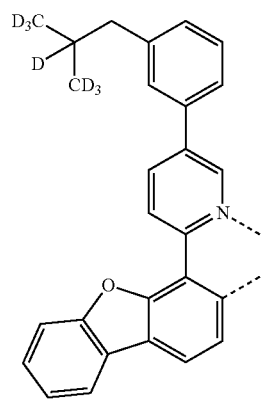 L_{B203}
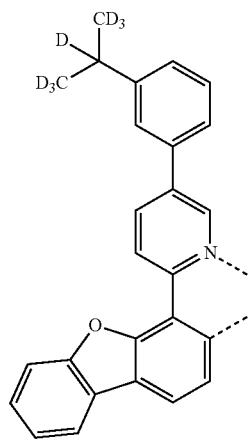 L_{B201}
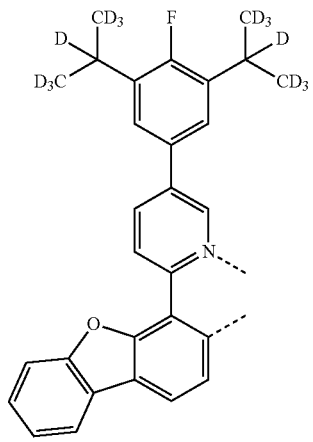 L_{B204}
L_{B202}
L_{B205}

321
-continued
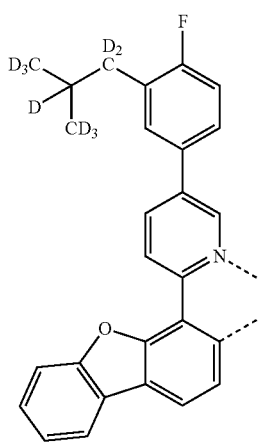
L_{B207}
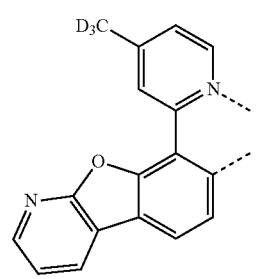
L_{B208}
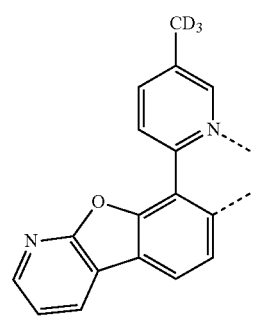
L_{B209}
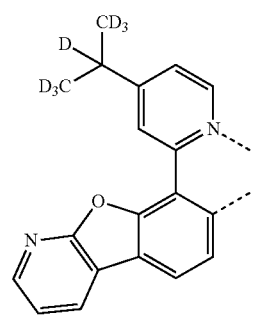
322
-continued
L_{B206}
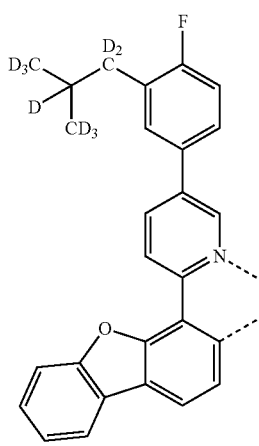
L_{B210}
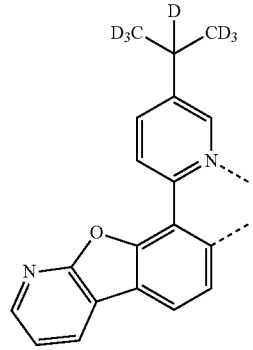
L_{B211}
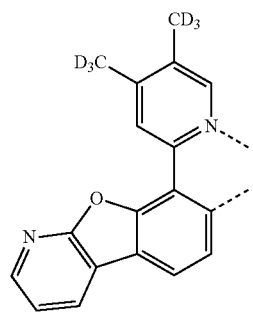
L_{B212}
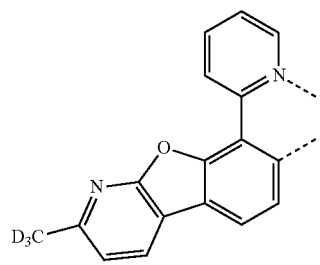
L_{B213}
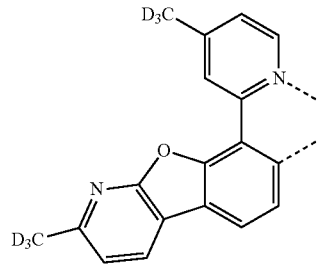
L_{B214}
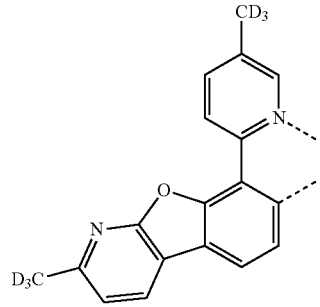

-continued
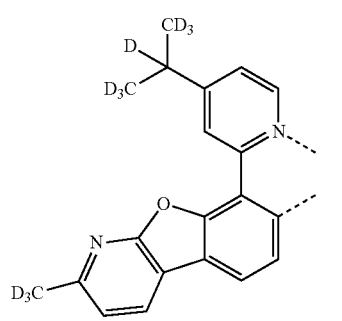 L<sub>B215</sub>
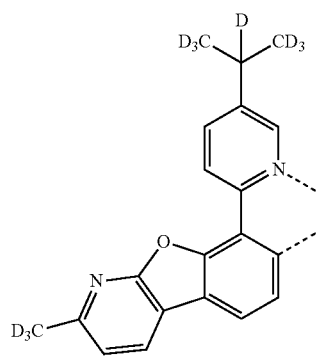 L<sub>B216</sub>
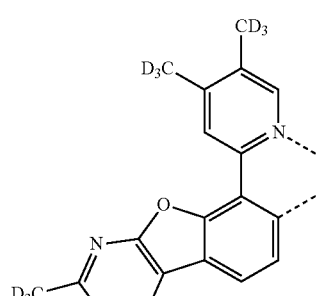 L<sub>B217</sub>
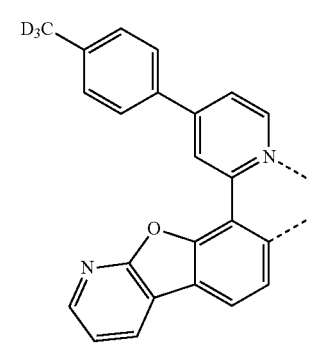 L<sub>B218</sub>
-continued
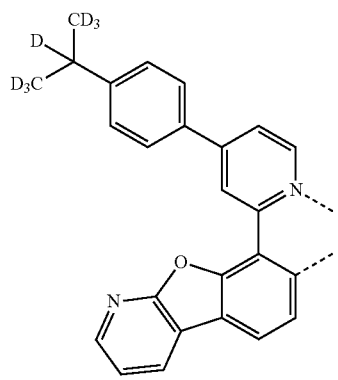 L<sub>B219</sub>
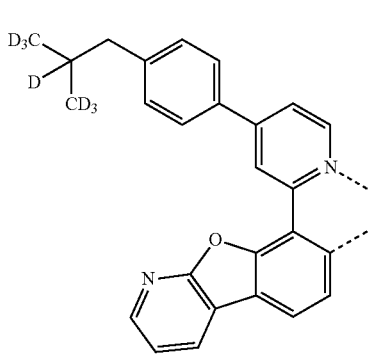 L<sub>B220</sub>
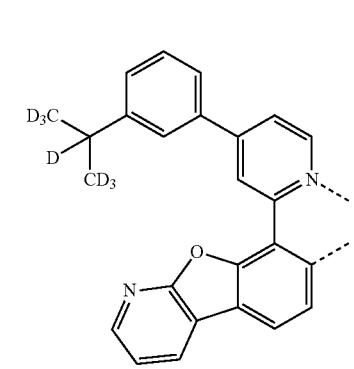 L<sub>B221</sub>
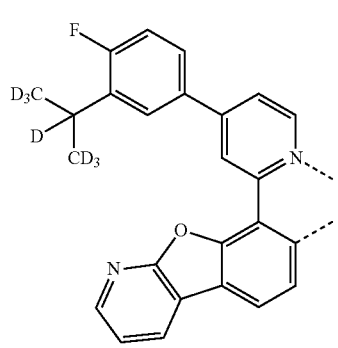 L<sub>B222</sub>

L<sub>B223</sub>
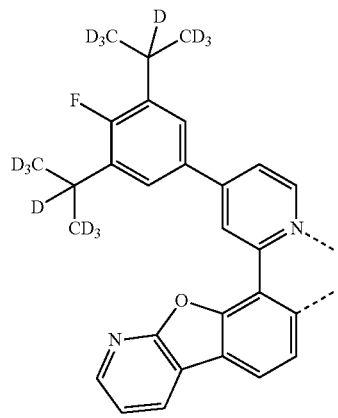
L<sub>B224</sub>
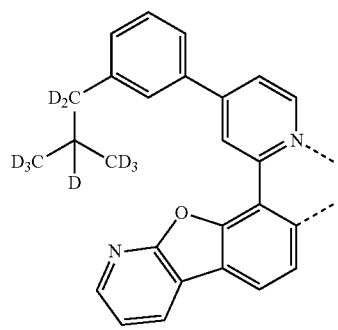
L<sub>B225</sub>
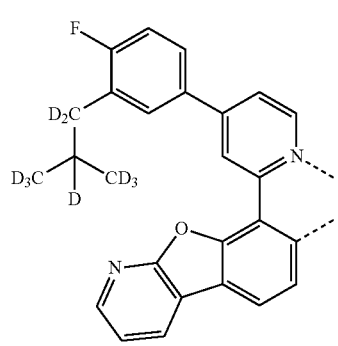
L<sub>B226</sub>
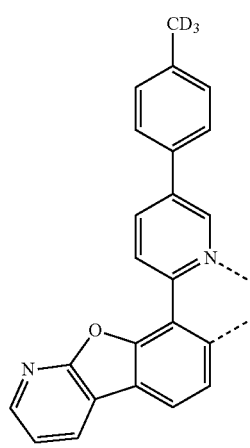
L<sub>B227</sub>
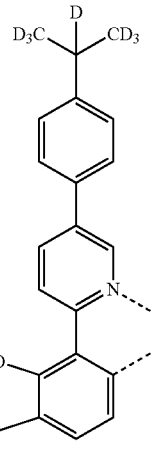
L<sub>B228</sub>
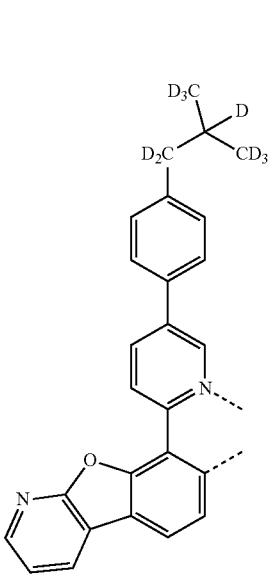
L<sub>B229</sub>
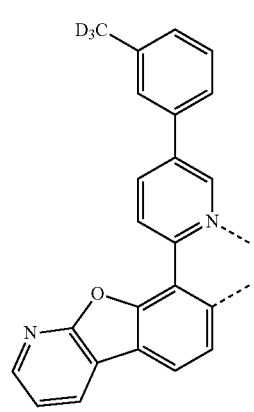

327
-continued
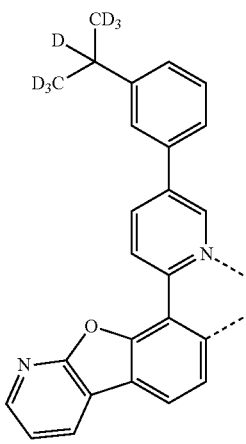
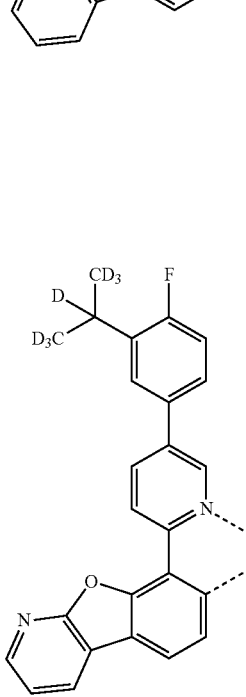
328
-continued
L_{B230}
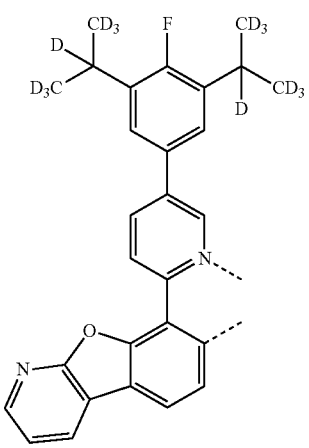
L_{B231}
L_{B232}
L_{B233}
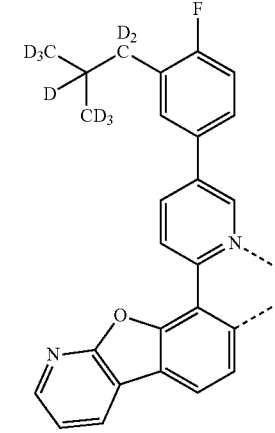
L_{B234}
L_{B235}
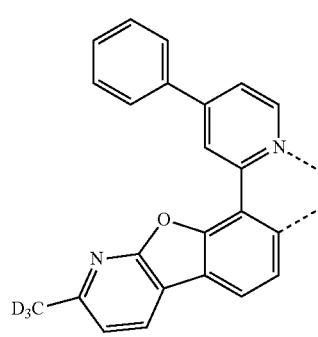
L_{B236}
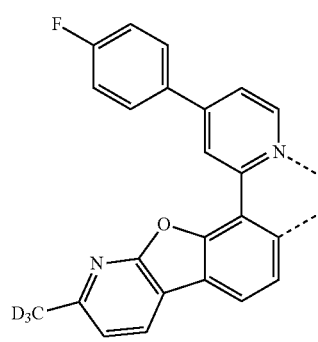

329
-continued
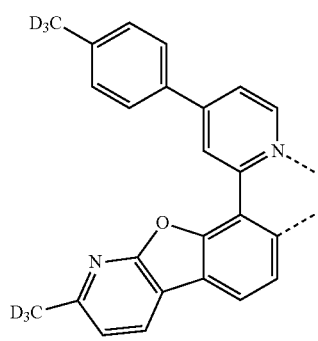
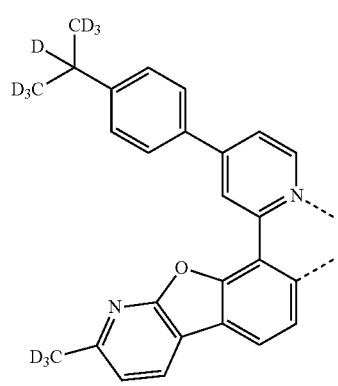
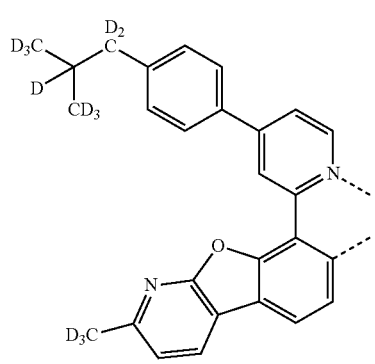
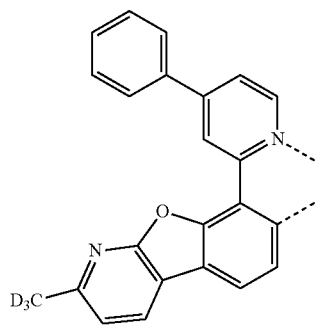
330
-continued
L_{B237}
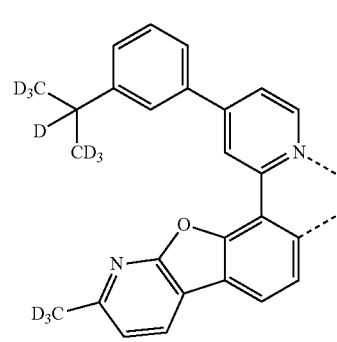
L_{B238}
L_{B242}
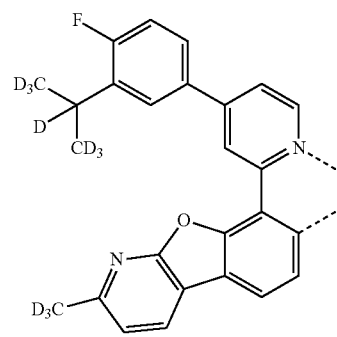
L_{B239}
L_{B243}
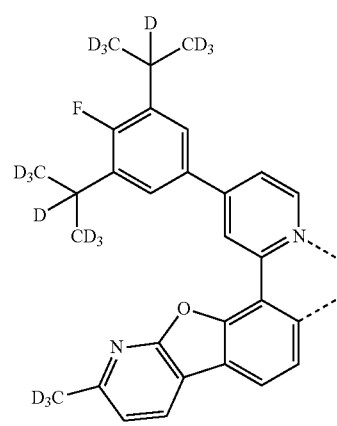
L_{B240}
L_{B244}
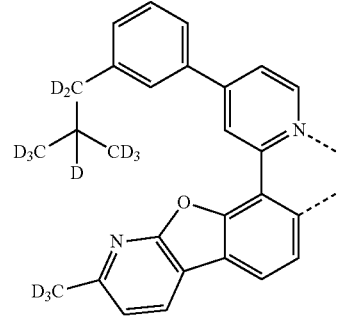

331
-continued
L_{B245}
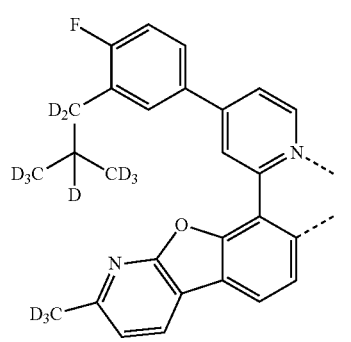
L_{B246}
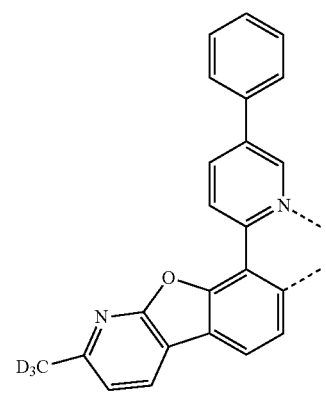
L_{B247}
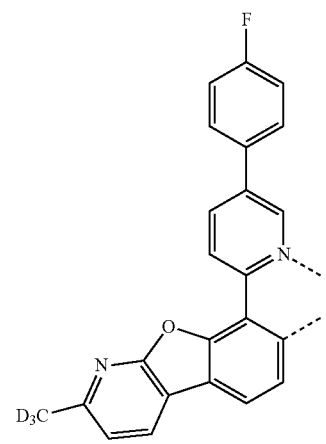
L_{B248}
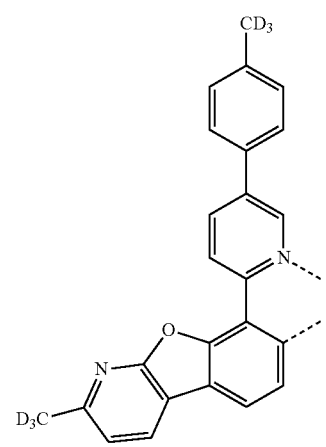
332
-continued
L_{B249}
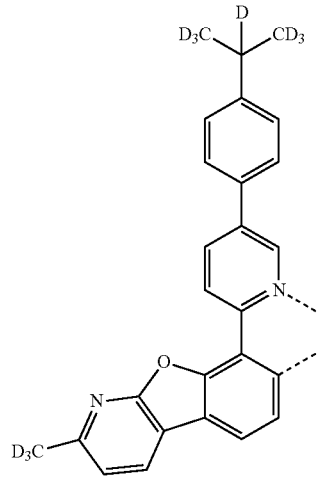
L_{B250}
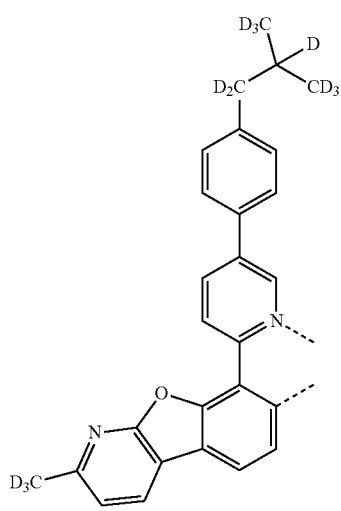
L_{B251}

333
-continued
L<sub>B252</sub>
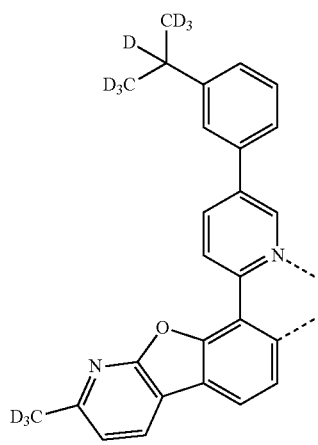
L<sub>B253</sub>
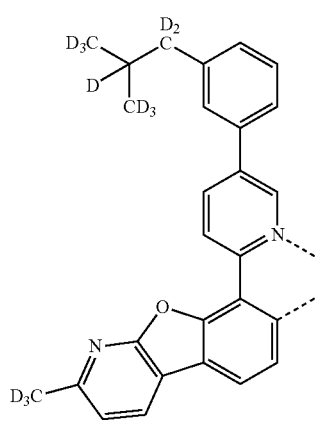
L<sub>B254</sub>
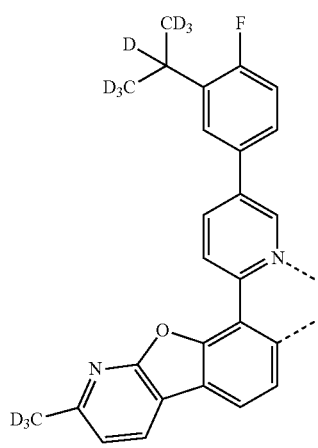
334
-continued
L<sub>B255</sub>
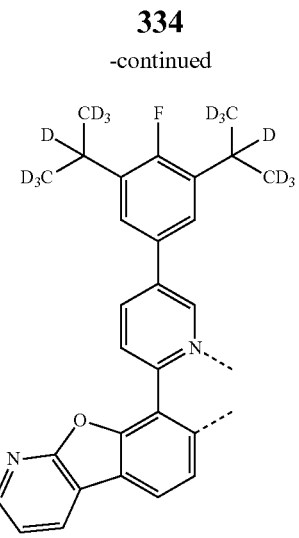
and
L<sub>B256</sub>
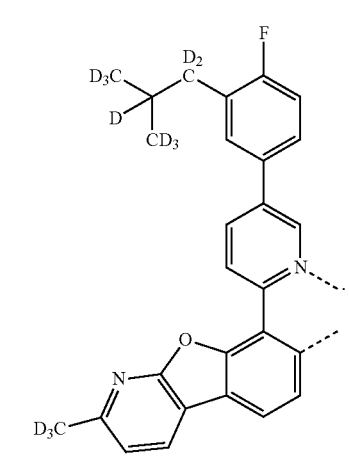
20. The compound of claim 1, wherein the compound is selected from the group consisting of:
Compound I-1
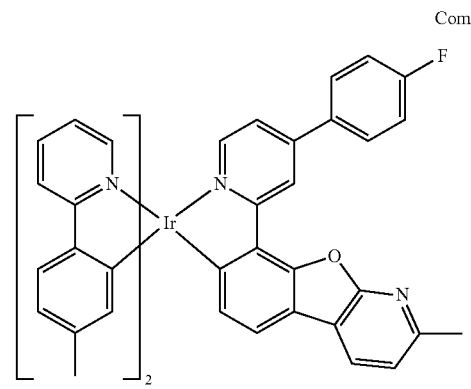

Compound I-2
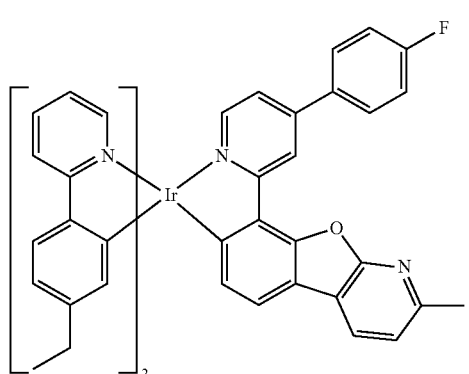
Compound I-3
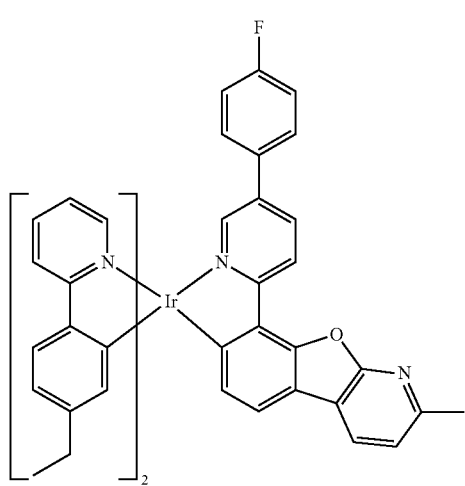
Compound I-4
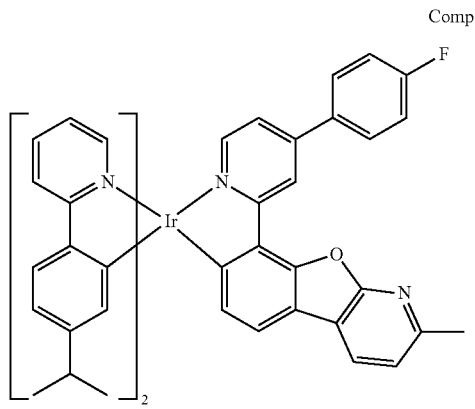
Compound I-5
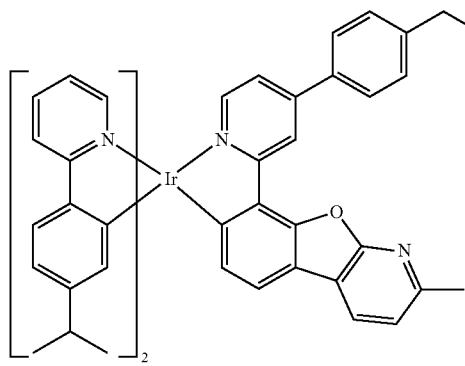
Compound I-6
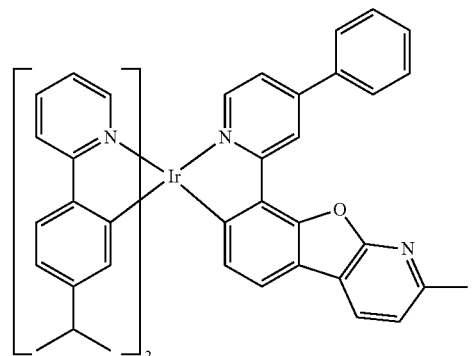
Compound I-7
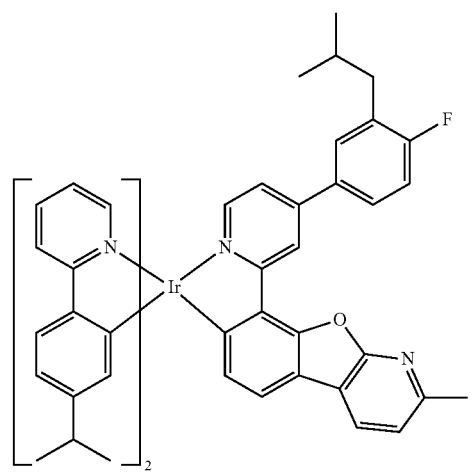
Compound I-8
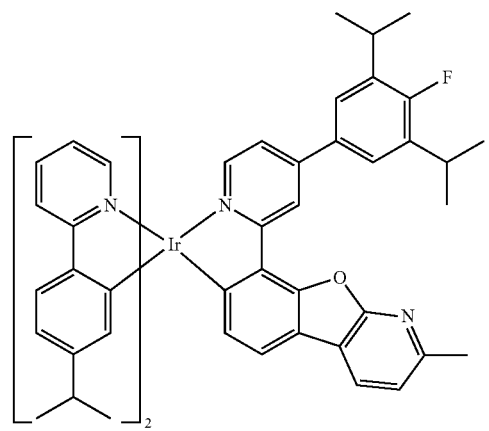

Compound I-9
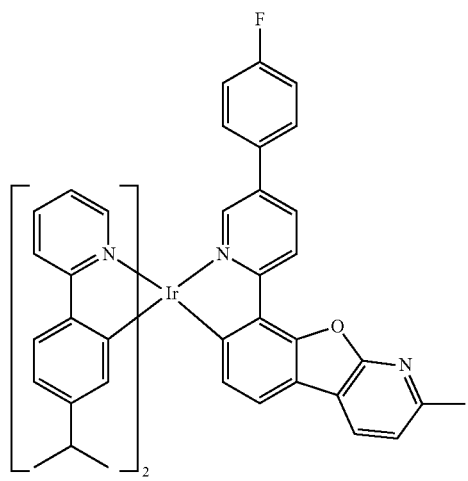
Compound I-10
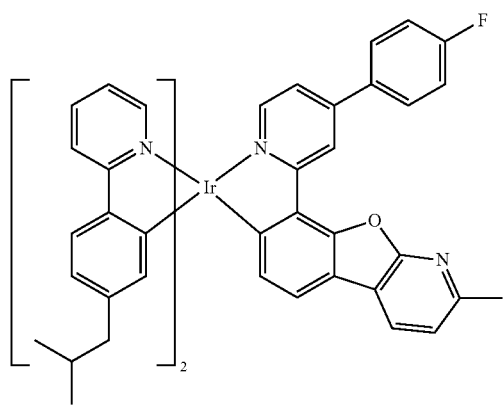
Compound I-11
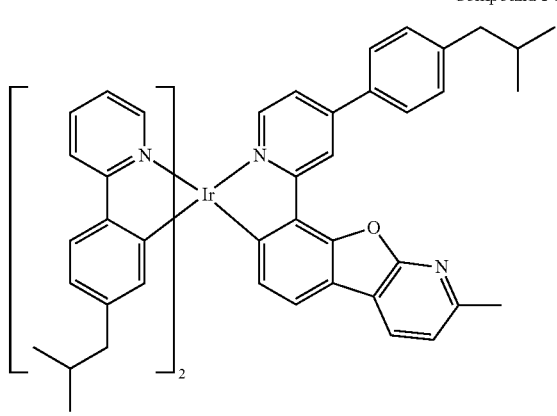
Compound I-12
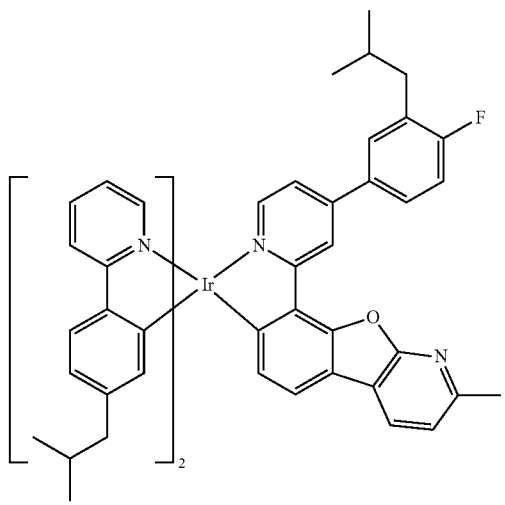
Compound I-13
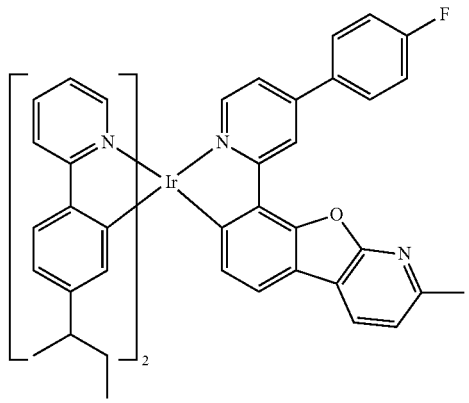
Compoun I-14
and
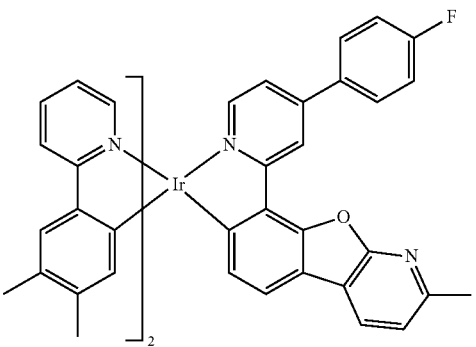

-continued

Compound I-15

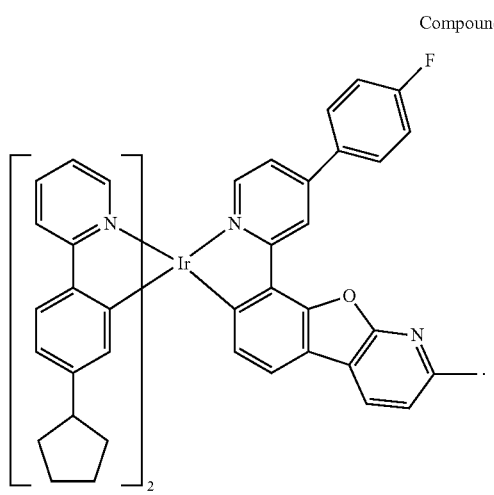

21. The compound of claim 1, wherein the compound is selected from the group consisting of:

Compound I-16

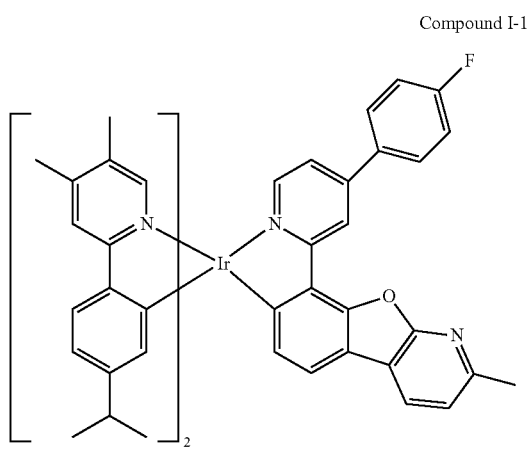

Compound I-17

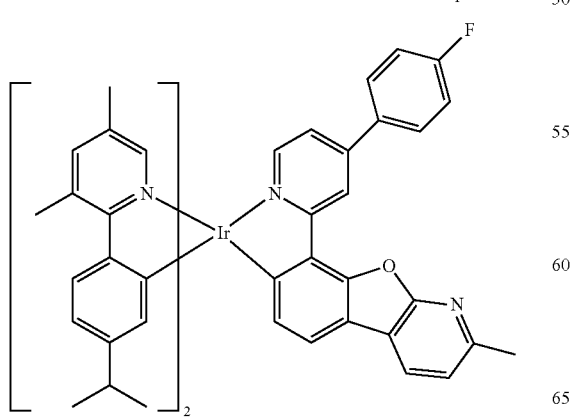

-continued

Compound I-18

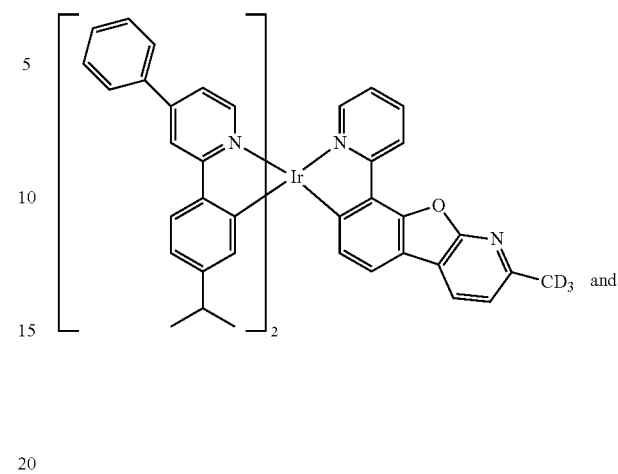

and

Compound I-19

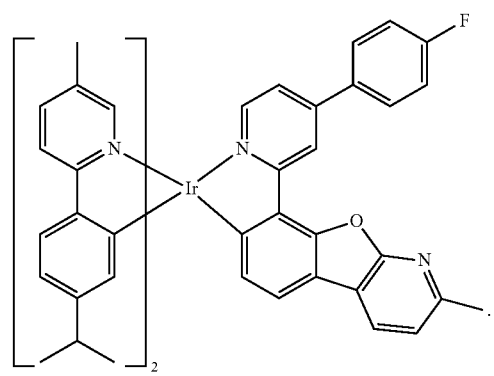

22. A first device comprising a first organic light emitting device, the first organic light emitting device comprising:
   an anode;
   a cathode; and
   an organic layer, disposed between the anode and the cathode, comprising a compound having the formula:

$$(L_A)_m Ir(L_B)_{3-m} \qquad (I);$$

wherein $L_A$ is

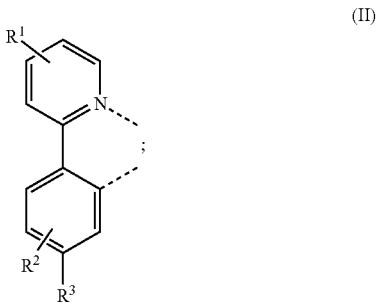

(II)

wherein $L_B$ is

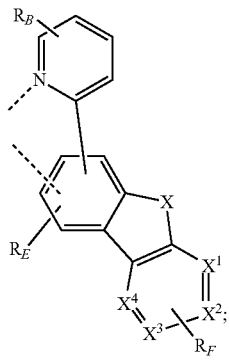

(V)

wherein $R_E$ represents mono or di-substitution, or no substitution;

$R^2$ represents mono, di, or tri-substitution, or no substitution;

wherein $R^1$, $R_B$, and $R_F$ are each independently mono, di, tri, or tetra-substitution, or no substitution;

wherein $X^1$, $X^2$, $X^3$, and $X^4$ are each independently CH or nitrogen, wherein the H in CH can be substituted by $R_F$;

wherein X is selected from the group consisting of O, S, and Se;

wherein $R^1$, $R^2$, $R_B$, $R_E$, and $R_F$ are each independently selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carboxyl, alkoxycarbonyl, cycloalkoxycarbonyl, heteroalkyloxycarbonyl, arylalkyloxycarbonyl, alkenyloxycarbonyl, cycloalkenyloxycarbonyl, heteroalkenyloxycarbonyl, alkynyloxycarbonyl, aryloxycarbonyl, heteroaryloxycarbonyl, cyano, carbylamino, sulfanyl, sulfinyl, sulfonyl, phosphino, and combinations thereof;

wherein $R^3$ is selected from the group consisting of alkyl, cycloalkyl, and combinations thereof;

wherein $R^3$ is optionally partially or fully deuterated; and wherein m is 1 or 2.

23. The first device of claim 22, wherein the organic layer is an emissive layer and the compound is an emissive dopant.

24. A formulation comprising a compound of claim 1.

* * * * *